United States Patent [19]

Cunningham et al.

[11] Patent Number: 5,534,617

[45] Date of Patent: Jul. 9, 1996

[54] HUMAN GROWTH HORMONE VARIANTS HAVING GREATER AFFINITY FOR HUMAN GROWTH HORMONE RECEPTOR AT SITE 1

[75] Inventors: Brian C. Cunningham, Piedmont; Henry Lowman, Hercules; James A. Wells, Burlingame, all of Calif.

[73] Assignee: Genentech, Inc., South San Francisco, Calif.

[21] Appl. No.: 67,160

[22] Filed: May 25, 1993

Related U.S. Application Data

[63] Continuation-in-part of Ser. No. 960,227, Oct. 13, 1992, abandoned, and Ser. No. 50,058, Apr. 30, 1993, abandoned, which is a continuation-in-part of Ser. No. 743,614, Aug. 9, 1991, abandoned, which is a continuation-in-part of Ser. No. 715,300, Jun. 14, 1991, abandoned, which is a continuation-in-part of Ser. No. 683,400, Apr. 10, 1991, abandoned, which is a continuation-in-part of Ser. No. 621,667, Dec. 3, 1990, abandoned, said Ser. No. 960,227, is a continuation of Ser. No. 875,204, Apr. 27, 1992, abandoned, which is a continuation of Ser. No. 428,066, Oct. 26, 1989, abandoned, which is a continuation-in-part of Ser. No. 264,611, Oct. 28, 1988, abandoned.

[51] Int. Cl.$^6$ .......................... C07K 14/61; A61K 38/25; C12P 21/06
[52] U.S. Cl. ............................................ 530/399; 435/69.4
[58] Field of Search ................................ 530/399; 314/2; 435/69.4

[56] References Cited

U.S. PATENT DOCUMENTS

| | | | |
|---|---|---|---|
| 4,446,235 | 5/1984 | Seeburg | 435/91 |
| 4,655,160 | 5/1987 | Seeburg | 530/399 |
| 4,670,393 | 6/1987 | Seeburg | 435/240 |
| 4,699,897 | 10/1987 | Jones et al. | 514/4 |
| 4,888,286 | 12/1989 | Crea | 435/172.3 |
| 5,350,836 | 9/1994 | Kopchick et al. | 530/399 |

FOREIGN PATENT DOCUMENTS

| | | |
|---|---|---|
| 0089666 | 9/1983 | European Pat. Off. |
| WO88/07578 | 6/1988 | WIPO |
| WO88/07084 | 9/1988 | WIPO |
| WO90/04788 | 3/1990 | WIPO |
| WO90/02809 | 3/1990 | WIPO |
| WO90/05185 | 5/1990 | WIPO |
| WO90/08823 | 8/1990 | WIPO |
| WO92/09690 | 6/1992 | WIPO |
| WO92/21029 | 11/1992 | WIPO |
| WO93/00109 | 1/1993 | WIPO |

OTHER PUBLICATIONS

Cunningham, B. et al., "Rational design of receptor-specific variants of human growth hormone", *Proc. Natl. Acad. Sci. USA* 88:3407–3411 (1991).

Roberts, B. et al., "Directed evolution of a protein: Selection of potent neutrophil elastase inhibitors displayed on M13 fusion phage", *Proc. Natl. Acad. Sci. USA* 89:2429–2433 (1992).

Rutter, W. et al., "Redesigning Proteins via Genetic Engineering", *Protein Engineering* 257–267 (Oxender & Fox, eds., A. R. Liss, Inc. 1987).

Lowman, H. et al., "Selection of High–Affinity Variants of Human Growth Hormone By Monovalent Phage Display", *Discussion of Mutations at American Society of Cell Biology Meeting* (1992).

Wharton et al., "Changing the Binding Specificity of a Repressor by Redesigning an α–Helix," *Nature* 316: 601–605 (1985).

Wharton et al., "Substituting an α–Helix Switches the Sequence–Specific DNA Interactions of a Repressor," *Cell* 38: 361–369 (1984).

Jones et al., "Replacing the Complementarity–Determining Regions in a Human Antibody with Those From a Mouse," *Nature* 321: 522–525 (1986).

Laskowski et al., "Positive Darwinian Selection in Evolution of Protein Inhibitors of Serine Proteinases," *Cold Spring Harbor Symp. Quant. Biol.* 52: 545–553 (1987).

Lewis, "Variants of Growth Hormone and Prolactin and Their Posttranslational Modifications," *Ann. Rev. Physiol.* 46: 33–42 (1984).

Leung et al., "Growth Hormone Receptor and Serum Binding Protein: Purification, Cloning and Expression," *Nature* 330: 537–543 (1987).

Boutin et al., "Cloning and Expression of the Rat Prolactin Receptor, a Member of the Growth Hormone/Prolactin Receptor Gene Family," *Cell* 53: 697–77 (1988).

Goeddel et al., "Direct Expression in *Escherichia coli* of a DNA Sequence Coding for Human Growth Hormone," *Nature* 281: 544–548 (1979).

Gray et al., "Periplasmic Production of Correctly Processed Human Growth in *Escherichia coli*: Natural and Bacterial Signal Sequences are Interchangeable," *Gene* 39: 247–254 (1985).

Li, "Human Growth Hormone: 1974–1981," *Mol. Cell. Biochem,* 46: 31–41 (1982).

Mills et al., "Fragments of Human Growth Hormone Produced by Digestion with Thrombin: Chemistry and Biological Properties," *Endocrinology* 107: 391–399 (1980).

Krivi et al., "Immunohistochemical Expression of Insulin––Like Growth Factor I During Skeletal Muscle Regeneration in Normal . . . ," Intl. Symp. on Growth Hormone, Abstract I–18, Serono Symposia, USA, Jun. 14–18, 1987.

Barlow et al., "Continuous and Discontinuous Protein Antigenic Determinants," *Nature* 322: 747–748 (1986).

Burstein et al., "Immunoreactivity and Receptor Binding of Mixed Recombinants of Human Growth Hormone and Chorionic Somatomammotropin," *PNAS USA* 75: 5391–5394 (1978).

(List continued on next page.)

Primary Examiner—Robert A. Wax
Assistant Examiner—K. Cochrane Carlson
Attorney, Agent, or Firm—Skjerven, Morrill, MacPherson, Franklin & Friel; Laura Terlizzi; Emily M. Haliday

[57] ABSTRACT

Human growth hormone variants are disclosed wherein the lysine at position 41 and/or the leucine at position 45 of native human growth hormone, numbered from the mature N–terminus of native human growth hormone, has been replaced with another amino acid. Also claimed are combination variants that have a higher binding affinity to the growth hormone receptor than wild-type human growth hormone.

4 Claims, 11 Drawing Sheets

OTHER PUBLICATIONS

Seeburg, "The Human Growth Hormone Gene Family: Nucleotide Sequences Show Recent Divergence and Predict a New Polypeptide Hormone," *DNA 1*: 239–249 (1982).

Kostyo et al., "Biological Characterization of Purified Native 20–kDA Human Growth Hormone," *Biochemica et Biophysica Acta 925*: 314 (1987).

Lewis et al., "A Naturally–Occurring Structural Variant of Human Growth Hormone," *J. Biol. Chem. 253*: 2679–2687 (1987).

Tokunaga et al., "Synthesis and Expression of a Human Growth Hormone (Somatotropin) gene Mutated to Change Cysteine –165 to Alanine," *Eur. J. Biochem. 153*: 445–449 (1985).

Camble et al., "Properties of Interferon α2 Analogues Produced from Synthetic Genes," in Peptides: Structure and Function, Proc. of the 9th Amer. Peptide Symp. (1985) eds. Deber et al., Pierce Chem. Co., Chic., IL pp. 375–384.

Kobilka et al., "Chimeric α2–, β2–Adrenergic Receptors: Delineation of Domains Involved in Effector Coupling and Ligand Binding Specificity," *Science 240*: 1310–1316 (1988).

Clayton et al., "Substitution of Murine for Human CD4 Residues Identifies Amino Acids Critical for HIV–gp120 Binding," *Nature 335*: 363–366 (1988).

Russell et al., "Recombinant Hormones from Fragments of Human Growth Hormone and Human Placental Lactogen," *J. Biol. Chem. 256*(1): 296–300 (1981).

Bajt et al., "Characterization of a Gain of Function Mutation of Integrin αIIβ3 (Platelet Glycoprotein IIb–IIIa)," *J. Biol. Chem. 267*(31): 22211–22216 (1992).

Bennett et al., "High Resolution Analysis of Functional Determinants on Human Tissue–Type Plasminogen Activator," *J. Biol. Chem. 266*(8): 5191–5201 (1991).

Berlot et al., "Identification of Effector–Activating Residues of G sa," *Cell 68*: 911–922 (1992).

Cunningham et al., "Receptor and Antibody Epitopes in Human Growth Hormone Identified by Homolog–Scanning Mutagenesis," *Science 243*: 1330–1336 (1990).

Cunningham et al., "High–Resolution Epitope Mapping of hGH–Receptor Interaction by Alanine–Scanning Mutagenesis," *Science 244*: 1081–1085 (1989).

Berendt et al., "The Binding Site on ICAM–1 for *Plasmodium calciparum*–Infected Erythrocytes Overlaps, but is Distinct LFA–1–Binding Site," *Cell 68*: 71–81 (1992).

Bettler et al., "Immunoglobulin E–binding site in Fc Receptor (FcRII/CD23) Identified by Homolog–Scanning Mutagenesis," *J. Biol. Chem. 267*(1): 185–191 (1992).

Ge et al., "Functional Domains of *Bacillus thuringiensis* Insecticidal Crystal Proteins," *J. Biol. Chem. 266*(27):17954–17958 (1991).

Nagashima et al., "Alanine–Scanning Mutagenesis of the Epidermal Growth Factor–Like Domains of Human Thrombomodul in Identifies Critical Residues for Its Cofactor Activity," *J. Biol. Chem. 268*(4): 2888–2892 (1993).

Venuti et al., Chapter 3: The Impact of Biotechnology on Drug Discovery, *Ann. Reports in Medicinal Chem.* pp. 289–298 Vinick ed., Academic Press, Inc. (1989).

Wertman et al., "Systematic Mutational Analysis of the Yeast ACT1 Gene," *Genetics 132*: 337–350 (1992).

Wells, J., "Systematic Mutational Analyses of Protein–Protein Interfaces," *Methods in Enzymology 202*: 390–411 Academic Press, Inc. (1991).

Zoller et al., "New Molecular Biology Methods for Protein Engineering," *Current Opinion in Structural Biology 1*: 605–610 (1991).

Zhang et al., "Toward a Simplification of the Protein Folding Problem: A Stabilizing Polyalanine α–Helix Engineered in T4 Lysozyme," *Biochem. 30*(8): 2012–2017 (1991).

Hotta et al., "Synthesis and *In Vitro* Bioactivity of Human Growth Hormone–Releasing Factor Analogs Substituted with a Single D–Amino Acid," *Biochem. Biophys. Res. Comm. 149*(2): 531–537 (1987).

Marseigne et al., "Synthesis and Biological Activity of $CCK_{26-33}$–Related Analogues Modified in Position 31," *J. Med. Chem. 31*(5): 96–970 (1988).

Paladini et al., "Molecular Biology of Growth Hormone," *CRC Crit. Rev. Biochem. 15*(1): 25–56 (1983).

Thorner and Vance, "Growth Hormone, 1988," *J. Clin. Invest. 82*: 745–747 (1988).

Nicoll et al., "Structural Features of Prolactins and Growth Hormones That Can Be Related to Their Biological Properties," *Endocrine Review 7*(2): 169–203 (1986).

Aston and Ivanyi, "Monoclonal Antibodies to Growth Hormone and Prolactin," *Pharmac. Ther. 27*: 403–424 (1985).

Chawla et al., "Structural Variants of Human Growth Hormone: Biochemical, Genetic, and Clinical Aspects," *Ann. Rev. Med. 34*: 519–547 (1983).

Creighton, T. E. *The Proteins*, Freeman & Co., eds. N.Y.

Chothia, C., *J. Mol. Biol. 150*: 1 (1976).

Harrington, A. C. et al., *J. Clin. Invest. 77*: 1817 (1986).

Braumann, G. et al., *J. Clin. Endocrin. Metab. 62*: 137 (1986).

Mandel, M. et al., *J. Mol. Biol. 53*: 154 (1970).

*Tissue Culture*, Academic Press, Kruse & Patterson, eds. (1973).

Carter, P. et al., *Nucl. Acids Res. 13*: 4331 (1986).

Zoller, M. J. et al., *Nuc. Ac. Res. 10*: 6487 (1982).

Wells, J. A. et al., *Philos. Trans. R. Soc. London Ser. A 317*: 415 (1986).

Barany, G. et al., *The Peptides* ((eds. Gross & Meienhofer) (1979) Acad. Press, N.Y. 2: 3–254.

Geysen et al., "Use of Peptide Synthesis to Probe Viral Antigens for Epitopes to a Resolution of a Single Amino Acid," *PNAS USA 81:* 3998–4002 (1984).

Edwards et al., *Science 239:* 769 (1988).

Isaksson et al., *Ann. Rev. Physiol. 47:* 483 (1985).

Hughes and Friesen, *Ann. Rev. Physiol. 47:* 469 (1985).

Argos, *Protein Eng. 2:* 101–113 (1988).

Janin et al., *J. Mol. Biol. 204:* 155–164 (1988).

Miller, *Protein Eng. 3:* 77–83 (1989).

Davies et al., *Ann. Rev. Biochem. 59:* 439–473 (1990).

Wells and De Vos, *Ann. Rev. Biophys. Biomol. Struct. 22:* 329–351 (1993).

Cunningham et al., *Science 254:* 821–825 (1991).

De Vos et al., *Science 255:* 306–312 (1992).

Li et al., *J. Am. Chem. Soc. 88:* 2050 (1966).

Bass et al., *Proteins 8:* 309–314 (1990).

Lowman et al., *Biochem. 30:* 10832–10838 (1991).

Fuh et al., *Science 256:* 1677–1680 (1992).

Lowman and Wells, *Methods: Companion Methods Enzymol. 3:* 205–216 (1991).

Wells, *Biochem. 29:* 8509–8517 (1990).

Martals et al., *FEBS Lett. 180:* 295–299 (1985).

Abdel–Maeguid, et al., "Three–Dimensional Structure of a Genetically Engineered Variant of Porcine Growth Hormone", *Proc. Natl. Acad. Sci. USA* 84:6434–6437 (1987).

Armstrong, et al., "Domain Structure of Bacteriophage fd Adsorption Protein", *FEBS Letters* 135:167–172 (1981).

Bowie, et al., "Deciphering the Message in Protein Sequences: Tolerance to Amino Acid Substitutions", *Science* 247:1306–1310 (1990).

Chang, et al., "High–Level Secretion of Human Growth Hormone by *Escherichia coli*", *Gene* 55:189–196 (1987).

Crissman and Smith, "Gene–III Protein of Filamentous Phages: Evidence for a Carboxy;–Terminal Domain with a Role in Morphogenesis", *Virology* 132:445–455 (1984).

Cunningham, et al., "Engineering Human Prolactin to Bind to the Human Growth Hormone Receptor", *Science* 24:1461–1465 (1990).

Cwirla, et al., "Peptides on Phage: A Vast Library of Peptides for Identifying Ligands", *Proc. Natl. Acad. Sci. USA* 87:6378–6382 (1990).

de la Cruz, et al., "Immunogenicity and Epitope Mapping of Foreign Sequences via Genetically Engineered Filamentous Phage", *J. Biol. Chem.* 263:4318–4322 (1988).

Devlin, et al., "Random Peptide Libraries: A Source of Specific Protein Binding Molecules", *Science* 249:404–406 (1990).

Fuh, et al., "The Human Growth Hormone Receptor", *J. Biol. Chem.* 265:3111–3115 (1990).

Geysen, et al., "A Priori Delineation of a Peptide which Mimics a Discontinuous Antigenic Determinant", *Mol. Immunology* 23:709–715 (1986).

Geysen, et al., "Antigen–Antibody Interactions at the Molecular Level: Adventures in Peptide Synthesis", *Immunology Today* 6:364–369 (1985).

Gussow, et al., "Generating Binding Activities from *Escherichia coli* by Expression of a Repertoire of Immunoglobulin Variable Domains", *Cold Spring Harbor Symposia on Quantitative Biology* LIV:265–272 (1989).

McFarland, et al., "Lutropin–Choriogonadotropin Receptor: An Unusual Member of the G Protein–Coupled Receptor Family", *Science* 245:494–499 (1989).

Parmley and Smith, "Antibody–Selectable Filamentous fd Phage Vectors: Affinity Purification of Target Genes", *Gene* 73:305–318 (1988).

Rasched and Oberer, "Ff Coliphages: Structure and Functional Relationships", *Microbiological Reviews* 50:401–427 (1986).

Rutter, et al., "Redesigning Proteins via Genetic Engineering", *Protein Engineering* 103–108, Oxender & Fox, eds., A. R. Liss, Inc., New York (1985).

Scott and Smith, "Searching for Peptide Ligands with an Epitope Library", *Science* 249:386–390 (1990).

Shortle, "Genetic Strategies for Analyzing Proteins", *Protein Engineering,* 103–108, Oxender & Fox, eds., A. R. Liss, Inc. New York (1987).

Smith "Filamentous Fusion Phage: Novel Expression Vectors That Display Cloned Antigens on the Virion Surface", *Science* 228:1315–1317 (1985).

Wells, et al., "Cassette Mutagenesis: An Efficient Method for Generation of Multiple Mutations at Defined Sites", *Gene* 34:315–323 (1985).

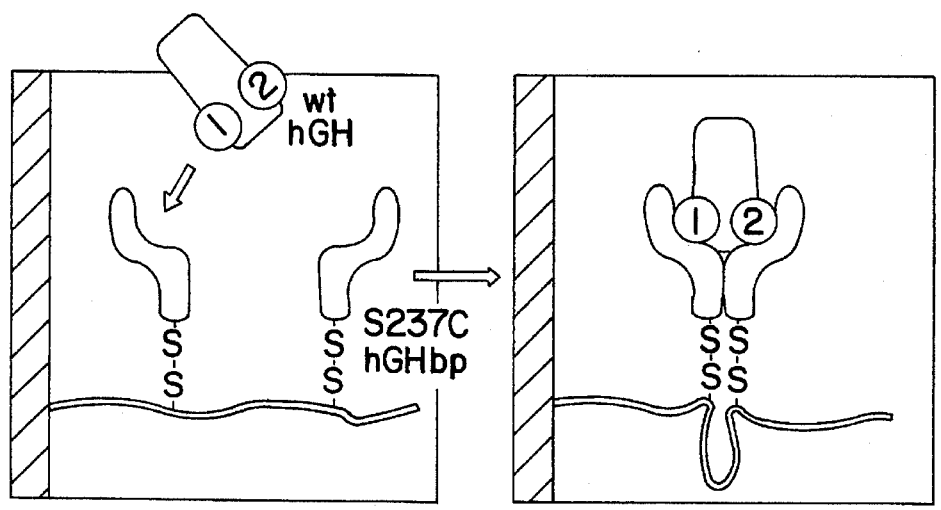
FIG. IA
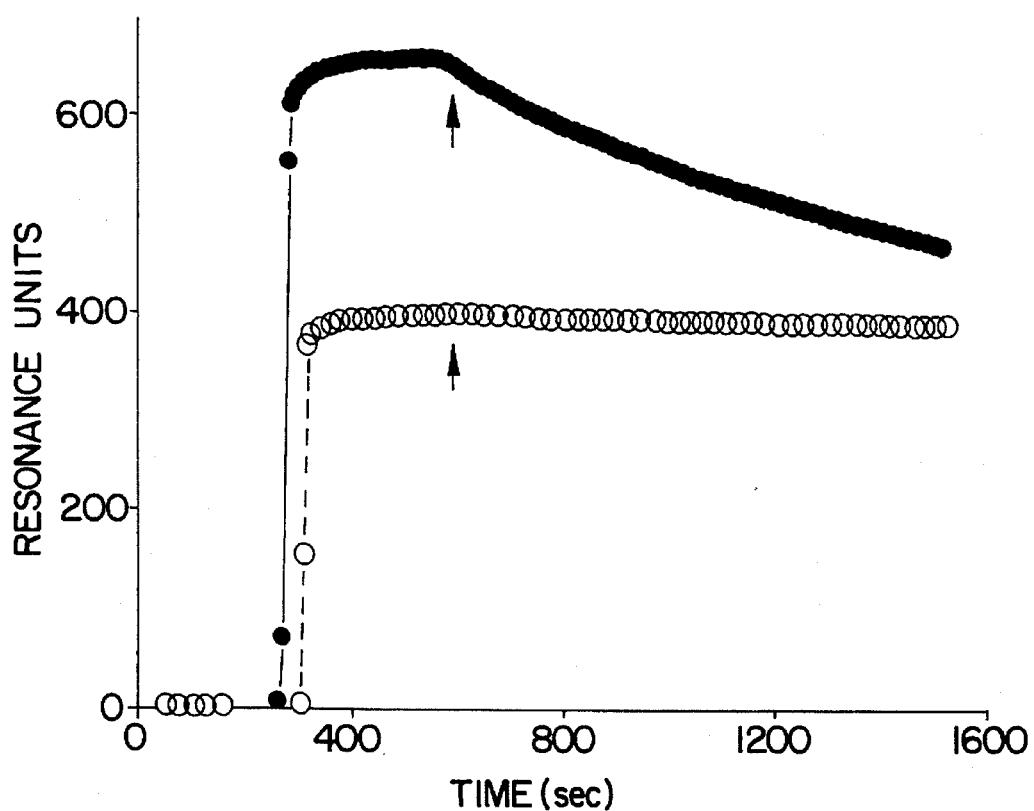
FIG. IB ically important for the rational protein and drug design.
HUMAN GROWTH HORMONE VARIANTS HAVING GREATER AFFINITY FOR HUMAN GROWTH HORMONE RECEPTOR AT SITE 1

This application is a continuation-in-part application of (a) U.S. Ser. No. 07/960,227 filed Oct. 13, 1992, now abandoned, which is a continuation of U.S. Ser. No. 07/875,204 filed Apr. 27, 1992, now abandoned, which is a continuation of U.S. Ser. No. 07/428,066 filed Oct. 26, 1989, now abandoned, which is a continuation-in-part of U.S. Ser. No. 07/264,611 filed Oct. 28, 1988, now abandoned, and (b) U.S. Ser. No. 08/050,058 filed Apr. 30, 1993, now abandoned, which is a continuation-in-part of U.S. Ser. No. 07/743,614 filed Aug. 9, 1991, now abandoned, which is a continuation-in-part of U.S. Ser. No. 07/715,300 filed Jun. 14, 1991, now abandoned, which is a continuation in part of U.S. Ser. No. 07/683,400 filed Apr. 10, 1991, now abandoned, which is a continuation-in-part of U.S. Ser. No. 07/621,667 filed Dec. 3, 1990 now abandoned.

BACKGROUND OF THE INVENTION

1. Field of the Invention

This invention relates to certain growth hormone variants with the variation being within an active domain.

2. Description of Background and Related Art

Human growth hormone (hGH) participates in much of the regulation of normal human growth and development. This 22,000-dalton pituitary hormone exhibits a multitude of biological effects, including linear growth (somatogenesis), lactation, activation of macrophages, and insulin-like and diabetogenic effects, among others. Chawla, *Annu. Rev. Med.*, 34: 519 (1983); Edwards et al., *Science*, 39: 769 (1988); Isaksson et al., *Annu. Rev. Physiol.*, 47: 483 (1985); Thorner and Vance, *J. Clin. Invest.*, 82: 745 (1988); Hughes and Friesen, *Annu. Rev. Physiol.*, 47: 469 (1985). These biological effects derive from the interaction between hGH and specific cellular receptors. Growth hormone deficiency in children leads to dwarfism, which has been successfully treated for more than a decade by exogenous administration of hGH. There is also interest in the antigenicity of hGH to distinguish among genetic and post-translationally modified forms of hGH (Lewis, *Ann. Rev. Physiol.*, 46: 33 [1984]), to characterize any immunological response to hGH when it is administered clinically, and to quantify circulating levels of the hormone.

hGH is a member of a family of homologous hormones that include placental lactogens, prolactins, and other genetic and species variants of growth hormone. Nichol et al., *Endocrine Reviews*, 7: 169 (1986). hGH is unusual among these in that it exhibits broad species specificity and binds to either the cloned somatogenic (Leung et al., *Nature*, 330: 537 [1987]) or prolactin (Boutin et al., *Cell*, 53: 69 [1988]) receptor. The cloned gene for hGH has been expressed in a secreted form in *E. coli* (Chang et al., *Gene*, 55: 189 [1987]) and its DNA and amino acid sequences have been reported. Goeddel et al., *Nature*, 281: 544 (1979); Gray et al., *Gene*, 39: 247 (1985). The three-dimensional folding pattern for porcine growth hormone (pGH) has been reported at moderate resolution and refinement. Abdel-Meguid et al., *Proc. Natl. Acad. Sci. USA*, 84: 6434 (1987). The receptor and antibody epitopes of hGH have been identified by homolog-scanning mutagenesis and alanine-scanning mutagenesis as described in the parent to this application and in Cunningham et al., *Science*, 243: 1330–1336 (1989) and Cunningham and Wells, *Science*, 244: 1081–1085 (1989).

There are a large number of high-resolution structures that show the molecular details of protein-protein interfaces (for reviews, see Argos, *Protein Eng.*, 2: 101–113 [1988]; Janin et al., *J. Mol. Biol.*, 204: 155–164 [1988]; Miller, *Protein Eng.*, 3: 77–83 [1989]; Davies et al., *Annu. Rev. Biochem.*, 59: 439–473 [1990]). These define contact residues, but not the energetics for them nor do they show how docking occurs. A comprehensive understanding of the role of contact residues in affecting association and dissociation is fundamental to molecular recognition processes, and is practically important for the rational protein and drug design.

Perhaps the best characterized hormone-receptor complex is that between hGH and the extracellular domain of its receptor (hGHbp). For a review, see Wells and De Vos, *Annu. Rev. Biophys. Biomol. Struct.*, 22: 329–351 (1993). High-resolution structural and mutational analysis (Cunningham and Wells, supra; Cunningham et al., *Science*, 254: 821–825 [1991]) and structural analysis (De Vos et al., *Science*, 255: 306–312 [1992]) has shown that one molecule of hGH binds two receptor molecules sequentially using distinct sites on the hormone, called Sites 1 and 2.

A number of naturally occurring mutants of hGH have been identified. These include hGH-V [Seeberg, *DNA*, 1: 239 (1982); U.S. Pat. Nos. 4,446,235, 4,670,393, and 4,665,180] and 20K hGH containing a deletion of residues 32–46 of hGH. Kostyo et al., *Biochem. Biophys. Acta*, 925: 314 (1987); Lewis et al., *J. Biol. Chem.*, 253: 2679 (1978).

One investigator has reported the substitution of cysteine at position 165 in hGH with alanine to disrupt the disulfide bond which normally exists between Cys-53 and Cys-165. Tokunaga et al., *Eur. J. Biochem.*, 153: 445 (1985). This single substitution produced a mutant that apparently retained the tertiary structure of hGH and was recognized by receptors for hGH.

Another investigator has reported the in vitro synthesis of hGH on a solid resin support. The first report by this investigator disclosed an incorrect 188 amino acid sequence for hGH. Li et al., *J. Am. Chem. Soc.*, 88: 2050 (1966); U.S. Pat. No. 3,853,832. A second report disclosed a 190-amino-acid sequence. U.S. Pat. No. 3,853,833. This latter sequence is also incorrect. In particular, hGH has an additional glutamine after position 68, a glutamic acid rather than glutamine at position 73, an aspartic acid rather than asparagine at position 106, and an asparagine rather than aspartic acid at position 108.

In addition to the foregoing, hybrid interferons have been reported that have altered binding to a particular monoclonal antibody. Camble et al., "Properties of Interferon-α2 Analogues Produced from Synthetic Genes" in *Peptides: Structure and Function, Proceedings of the Ninth American Peptide Symposium*, Deber et al., eds. (Pierce Chemical Co., Chicago, Ill., 1985), pp. 375–384. As disclosed therein, amino acid residues 101–114 from α-1 interferon or residues 98–114 from γ-interferon were substituted into α-2 interferon. α-2 interferon binds NK-2 monoclonal antibody, whereas α-1 interferon does not. This particular region in α-2 interferon apparently was chosen because 7 of the 27 amino acid differences between α-1 and α-2 interferon were located in this region. The hybrids so obtained reportedly had substantially reduced activity with NK-2 monoclonal antibody. When tested for antiviral activity, such hybrids demonstrated antiviral activity on a par with the activity of wild-type α-2 interferon. Substitutions of smaller sections within these regions were also reported. Sequential substitution of clusters of 3 to 7 alanine residues was also proposed. However, only one analog [Ala-30,32,33] IFN-α2 was disclosed.

Alanine substitution within a small peptide fragment of hen egg-while lysozyme and the effect of such substitutions on the stimulation of 2A11 or 3A9 cells has also been reported. Allen et al., *Nature,* 327: 713–715 (1987).

Others have reported that binding properties can be engineered by replacement of entire units of secondary structure including antigen binding loops (Jones et al., *Nature,* 321: 522–525 [1986]) or DNA recognition helices. Wharton et al., *Nature,* 316: 601–605 (1985).

The structure of amino-terminal methionyl bovine growth hormone (bGH) containing a spliced-in sequence of hGH including histidine 18 and histidine 21 has been shown. U.S. Pat. No. 4,880,910. Additional hGH variants are described in the parent applications to this application and in copending U.S. Ser. Nos. 07/715,300 filed Jun. 14, 1991 and 07/743,614 filed Aug. 9, 1991, and WO 92/09690 published Jun. 11, 1992. hGH variants are also disclosed (WO 93/00109 published 7 Jan. 1993) having the GH moiety covalently attached to polyethylene glycol (PEG) at one or more amino acids, including those wherein the PEG molecule is attached to the lysine at position 41.

hGH variants are also reported in WO 92/21029 published 26 Nov. 1992, which discloses the 1:2 complex dimer between GH and two receptor molecules. The variant is a monomeric polypeptide ligand which comprises in its native conformation four amphipathic alpha helices and which binds to its receptor through two sites in sequential order. This variant comprises a mutation introduced into site 1 or site 2, provided that when the ligand is GH, at least two residues are mutated, one each in the N-terminal about 15 residues of the native hormone and in helix C, or site 1 is mutated so as to increase the affinity of the ligand for its receptor at site 1.

It has previously been shown that monovalent phage display (Bass et al., *Proteins,* 8: 309–314 [1990]) can be used to improve the affinity of Site 1 in hGH for the hGHbp. Lowman et al., *Biochemistry,* 30: 10832–10838 (1991). Modest improvements in binding affinity (3 to 8-fold tighter than wild-type hGH) were produced by sorting three independent libraries each mutated at four different codons in Site 1. An hGH mutant slightly enhanced in binding affinity for Site 1 and blocked in its ability to bind Site 2 was a better antagonist of the hGH receptor than the Site 2 mutant alone. Fuh et al., *Science,* 256: 1677–1680 (1992). It would be desirable to improve Site 1 affinity further to obtain an even better antagonist that may have utility in treating conditions of GH excess such as acromegaly.

Additional improvements in Site 1 affinity might be obtained by mutating more residues per library. However, it was not feasible to generate enough transformants to ensure that all possible residue combinations were represented when more than about five codons were randomized simultaneously. Lowman and Wells, *Methods: Companion Methods Enzymol.,* 3: 205–216 (1991). Mutations at protein-protein interfaces usually exhibit additive effects upon binding. Wells, *Biochemistry,* 29: 8509–8517 (1990).

It is desired to obtain much larger improvements in affinity. It has been disclosed that the lysine residues of hGH and bGH are involved in the interaction of hGH and bGH with somatotropic receptors, with the structure-function relationship particularly implicating the lysine or arginine residues at positions 41, 64, 70, and 115. Martal et al., *FEBS Lett.,* 180: 295–299 (1985). Lysine residues were chemically modified by methylation, ethylation, guanidination, and acetimidination, resulting in reduced activity by radioreceptor assay.

It is an object of the present invention to provide hGH variants having desirable biological, biochemical, and immunogenic properties that are different as compared to the same properties of the hormone from which such variants are derived.

It is another object to provide human growth hormone variants having modified binding and/or biological activity with the somatogenic receptor of hGH and increased therapeutic value.

It is a further object to provide DNA sequences, vectors, and expression hosts containing such vectors for the cloning and expression of nucleic acid encoding such hGH variants.

It is yet another object to provide better antagonists to the hGH receptor that have utility in treating conditions of GH excess such as acromegaly.

SUMMARY OF THE INVENTION

Accordingly, the present invention provides specific hGH variants wherein the lysine at position 41 or the leucine at position 45 of native hGH, numbered from the mature N-terminus of native hGH, has been replaced with another amino acid. Preferably in the variant the amino acid used for replacement is an isoleucine or arginine residue if the position is 41 or is a tryptophan residue if the position is 45.

In another aspect, the invention provides a hGH variant having the sequence K41R,Y42R,L45W,Q46W; K41R, Y42Q,L45W,Q46W; or K41I,Y42H,L45W,Q46W, alone or wherein further the residues at positions 174 and 176 are replaced with serine and tyrosine residues, respectively.

In yet another aspect, the invention supplies a hGH variant having the sequence F54P,E56D,I58T,R64K; F54P, E56W,I58T,R64K; or F54P,R64K, alone or in combination with a sequence described above where K41 is replaced.

In a further aspect, the invention supplies a hGH variant above having the sequence K41I,Y42H,L45W,Q46W,F54P, R64K.

In a still further aspect, the invention provides a hGH variant having the sequence F10A,M14W,H18D,H21N alone or in combination with one of the sequences R167D, D171S,E174S,F176Y,I179T; R167N,D171S,E174S,F176Y, I179T; R167E,D171S,E174S,F176Y; or R167N,D171N, E174S,F176Y,I179T. Of these, the preferred variants have the sequence F10A,M14W,H18D,H21N,R167N,D171S, E174S,F176Y,I179T or F10A,M14W,H18D,H21N,R167N, D171A,E174S,F176Y,I179T.

The most preferred hGH variants herein have the sequence F10A,M14W,H18D,H21N,K41I,Y42H,L45W, Q46W,F54P,R64K,R167N, D171S,E174S,F176Y,I179T or the sequences H18A,Q22A,F25A,D26A,Q29A,E65A, K168A,E174A; H18D,Q22A,F25A,D26A,Q29A,E65A, K168A,E174S; H18A,Q22A,F25A,D26A,Q29A,E65A, K168A,E174 S; or H18D,Q22A,F25A,D26A,Q29A,E65A, K168A,E174A.

In other aspects, the invention provides a composition comprising the hGH variants described above in a pharmaceutically acceptable carrier, as well as a nucleic acid sequence encoding the above-described hGH variants, a vector comprising this nucleic acid sequence, a host cell comprising this vector, preferably a bacterial host cell, and a process for preparing the hGH variants comprising culturing the host cells and recovering the variants from the culture, including the culture medium.

The hGH variants claimed in accordance with this invention were discovered in one of two ways. The first was by means of a comprehensive analysis of the energetic importance of 30 side-chains buried at the interface between hGH and hGHbp to assess the roles of contact side-chains in modulating the affinity and kinetics of binding. This was carried out by converting each side-chain in hGH to alanine and measuring the kinetics and affinity using a biosensor device. This device detects binding of the mutated hormones to the immobilized hGHbp by changes induced in refractive index. The data generated on the biosensor match affinities obtained by radioimmune assay in solution. The study shows that only one-quarter of the side-chains buried at the interface can account for the majority of the binding energy. One of these mutants is at position 45 of hGH. Another mutant discovered by this technique is the combination mutant: H18A,Q22A,F25A,D26A,Q29A,E65A,K168A,E174A, which in theory will bind about 200-fold more tightly to the GH receptor than wild-type hGH.

The second method by which the variants herein were discovered, in particular those at positions 41 and 45, is a selection procedure for constructing variants of hGH with very high affinity for hGHbp. Affinity-enhanced variants were combined from libraries in which other residues at the interface were mutated independently.

Specifically, five libraries of mutated hGH genes (each containing about $2 \times 10^5$ protein variants) were created by randomly mutating four different codons at residues that were shown to be important for receptor binding by structural or functional criteria. Mutated proteins from the libraries were displayed as single copies from their respective filamentous phagemid particles and sorted for binding to immobilized receptor in vitro. Phagemid particles that bound the immobilized receptor were eluted and propagated. After three to seven rounds of such binding enrichments, the highest affinity variants isolated from each library had modest improvements in binding affinity (from 3- to 6-fold). Combining these affinity-enhanced mutants created a hGH variant with 15 substitutions that bound about 400-fold more tightly to the receptor than wild-type hGH.

The fact that the free-energy effects of these mutations acted additively offered a solution to the limitation that no more than about five codons could be sampled exhaustively and simultaneously because of the limits of DNA transfection efficiency in creating the library. The affinity enhancements occurred predominantly through slowing the off-rate of the hormone (>60-fold), and partly through increasing the on-rate (up to 4-fold). The residues where the greatest improvements in affinity occurred were those that modulated binding affinity as identified by alanine-scanning mutagenesis. The sites that were most highly conserved as a wild-type residue after binding selection tended to be those found to be important by alanine-scanning mutagenesis, and not necessarily those which were most highly buried at the interface. These studies show that hormone receptor interfaces can be dramatically improved by randomization and phage display, and suggest that good residues to target are those shown to be functionally important by alanine-scanning mutagenesis.

BRIEF DESCRIPTION OF THE DRAWINGS

FIGS. 1A and 1B show the reaction (FIG. 1A) and kinetics (FIG. 1B) for binding of hGH or (G120R)hGH to the (S237C)hGHbp coupled to the BIAcore™ biosensor. The (S237C)hGHbp was immobilized on the thiol-dextran matrix (FIG. 1A) at a level of 1220 RU's, which corresponds to 1.2 ng/mm². In the binding-profile example (FIG. 1B), hGH (open symbols) or (G120R)hGH (filled symbols) was injected at saturating concentrations (>200 nM) to follow association and establish the limiting amount of bound hormone from which a stoichiometry was calculated. After saturation, the injector loop was switched to buffer to follow dissociation (indicated by the arrow).

FIG. 6A shows the hGH site-1 functional epitope. Residues involved in receptor binding, according to alanine-scanning mutagenesis, are shown on a cartoon model of hGH, derived from the hGH(hGHbp)₂ crystal structure. de Vos et al., supra. The effects of alanine substitutions (or Gln substitution in the case of K41) are shown based on BIAcore™ kinetics measurements, except for sites M14, H21, F54, E56, I58, S62, N63, and Y164. At these sites, BIAcore™ data were either not available or indicated a negligible effect on binding, and so the effect shown is based on RIA data. The change in binding free energy ($\Delta\Delta G$) was calculated as $-RT \ln[K_d(\text{Ala mutant})/K_d(\text{hGH})]$. Dark spheres show alanine substitutions that improved binding ($\Delta\Delta G = -1$ to $-0.5$ kcal/mol). The four white spheres of increasing size denote alanine substitutions that reduced binding energy by +0.5 to 1.0 kcal/mol, +1.0 to 1.5 kcal/mol, +1.5 to 2.0 kcal/mol, or +2.0 to 2.5 kcal/mol, respectively.

FIG. 6B is the hGH site-1 structural epitope. The four white spheres of increasing size represent a change in solvent-accessible area of $-20$ to $0$ Å², $0$ to $20$ Å², $20$ to $40$ Å², or $40$ to $60$ Å², respectively, at each residue upon alanine substitution, as calculated from the hGH(hGHbp)₂ X-ray crystal structure.

FIG. 6C denotes the conservation of hGH residues in randomized phagemid libraries. Residues that were randomized, four positions at a time, in phage-displayed hGH libraries are shown: helix-1 [F10, M14, H18, H21]; mini-helix-1 [K41, Y42, L45, Q46]; Loop-A [F54, E56, I58, R64]; helix-4A [K172, E174, F176, R178]; helix-4B [R167, D171, T175, I179]. The fraction of wild-type hGH residues found at each position after sorting for hGHbp binding [data reported herein and in Lowman et al., supra] is indicated by the size of black spheres: The smallest black sphere is 0–10% conserved, the next larger is 10–25% conserved, the next larger is 25–50% conserved, and the largest is >50% conserved.

FIG. 8A depicts a comparison with x-ray structure of hGH-(hGHbp)$_2$. The side-chain area of hGH residues buried by receptor-1 binding (solvent accessible area of: [free hGH]-[hGH-hGHbp complex] is plotted.

FIG. 8B depicts the results of phage display and alanine-scanning mutagenesis. The functional effect of Ala substitutions in hGH is plotted as in [$K_d$ (Ala mutant)/$K_d$(hGH)]. Binding data were taken from BIAcore™ biosensor measurements, except where kinetics data were not available. For these non-contact residues (F10, F54, I58), values for $K_d$ obtained from radio-immunoprecipitation assays were used. Cunningham et al., 1989, supra.

FIG. 8C denotes conservation of residues among evolutionary variants. The amino acid sequences (Genbank, vol. 75, February, 1993) of growth hormones from monkey, pig, elephant, hamster, whale, alpaca, fox, horse, sheep, rat, turtle, chicken, mink, cow, salmon, frog, and trout, as well as human placental lactogen, hGH(20K), and hGH-V were compared with that of "wild-type" hGH. Prolactin evolutionary variants were not included. The natural logarithm of the frequency with which the wild-type hGH residues appear among these variants is plotted.

DESCRIPTION OF THE PREFERRED EMBODIMENTS

Variants

Figure 2A:
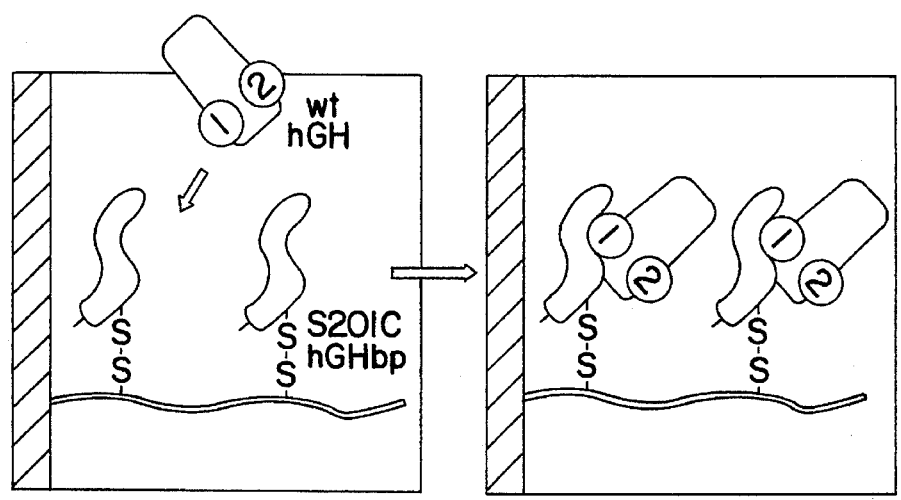
FIGS. 2A and 2B show the reaction (FIG. 2A) and kinetics (FIG. 2B) for binding of hGH (open symbols) or (G120R)hGH (closed symbols) to the (s201C)hGHbp coupled on the BIAcore™ biosensor. The (S201C)hGHbp was immobilized at a level of 1480 RU's (1.48 ng/mm²) on the biosensor. Binding conditions and profiles are analogous to those in FIGS. 1A and 1B.

The DNA and amino acid sequences of hGH have been reported. Goeddel et al., supra; Gray et al., supra. The present invention describes novel hGH variants produced using either the alanine-scanning methodology or phagemid selection methods. The hGH variants of the present invention may be expressed in any recombinant system that is capable of expressing native or met hGH.

Variant hGH sequence notation defines the actual amino acid substitutions in the hGH variants of the present invention. For a variant, substitutions are indicated by a letter representing the wild-type residue (in single-letter code), a number indicating the amino acid position in the wild-type sequence, and a second letter indicating the substituted amino acid residue. For example, R64K indicates a mutation in which Arg 64 is converted to Lys. Multiple mutants are indicated by a series of single mutants separated by commas.

In one embodiment, these hGH variants contain substitutions at position(s) 41 and/or 45, optionally with other substitutions, e.g., at positions 10, 14, 18, 21, 167, 171, 172, 174, 176, 178, and 179. Also preferred are those having the sequence K41R,Y42R,L45W,Q46W; K41R,Y42Q,L45W, Q46W; or K41I,Y42H,L45W,Q46W, alone or wherein further the residues at positions 174 and 176 are replaced with serine and tyrosine residues, respectively. Additionally preferred is an hGH variant having the sequence K41I,Y42H, L45W,Q46W,F54P,R64K. The most preferred hGH variant in this category has the sequence:
F10A,M14W,H18D,H21N,K41I,Y42H,L45W,Q46W,F54P, R64K,R167N, D171S,E174S,F176Y,I179T.

In another embodiment, the hGH variants discovered herein have the sequence F54P,E56D,I58T,R64K; F54P, E56W,I58T,R64K; or F54P,R64K, alone or in combination with a sequence described above where K41 is replaced.

In a third embodiment, the hGH variants discovered herein have one of the sequences:
H18A,Q22A,F25A,D26A,Q29A,E65A,K168A,E174A;
H18D,Q22A,F25A,D26A,Q29A,E65A,K168A,E174S;
H18A,Q22A,F25A,D26A,Q29A,E65A,K168A,E174S; or
H18D,Q22A,F25A,D26A,Q29A,E65A,K168A,E174A.

Alanine-Scanning Mutagenesis

In one embodiment, the invention herein utilizes a systematic analysis of hGH to determine one or more active sites in the polypeptide that are involved in the interaction of the polypeptide with its receptor. Such analysis is conveniently performed using recombinant DNA technology. In general, the DNA sequence encoding hGH is cloned and manipulated so that it may be expressed in a convenient host. DNA encoding hGH can be obtained from a genomic library, from cDNA derived from mRNA in cells expressing the hGH, or by synthetically constructing the DNA sequence. Maniatis et al., *Molecular Cloning: A Laboratory Manual*, Cold Spring Harbor Laboratory, N.Y. (1982).

The wild-type hGH DNA is then inserted into an appropriate plasmid or vector that is used to transform a host cell. Prokaryotes are preferred for cloning and expressing DNA sequences to produce the hGH variants. For example, *E. coli* K12 strain 294 (ATCC No. 31446) may be used, as well as *E. coli* B, *E. coli* X1776 (ATCC No. 31537), and *E. coli* c600 and c600hfl, and *E. coli* W3110 (F⁻, γ⁻, prototrophic, ATCC No. 27325), bacilli such as *Bacillus subtilis*, and other enterobacteriaceae such as *Salmonella typhimurium* or *Serratia marcescens*, and various *Pseudomonas* species. The preferred prokaryote is *E. coli* W3110 (ATCC 27325). When expressed intracellularly in prokaryotes, the hGH typically contains an N-terminal methionine or a formyl methionine and is not glycosylated. When expressed extracellularly into the medium, the hGH does not contain an N-terminal methionine. These examples are, of course, intended to be illustrative rather than limiting.

In addition to prokaryotes, eukaryotic organisms, such as yeast cultures, or cells derived from multicellular organisms, may be used. In principle, any such cell culture is workable. However, interest has been greatest in vertebrate cells, and propagation of vertebrate cells in culture (tissue culture) has become a repeatable procedure. *Tissue Culture,* Academic Press, Kruse and Patterson, editors (1973). Examples of such useful host cell lines are VERO and HeLa, Chinese hamster ovary (CHO), W138, BHK, COS-7, and MDCK cell lines.

In general, plasmid vectors containing replication and control sequences that are derived from species compatible with the host cell are used in connection with these hosts. The vector ordinarily carries a replication site, as well as sequences that encode proteins that are capable of providing phenotypic selection in transformed cells. For example, *E. coli* may be transformed using pBR322, a plasmid derived from an *E. coli* species. Mandel et al., *J. Mol. Biol.,* 53: 154 (1970). Plasmid pBR322 contains genes for ampicillin and tetracycline resistance and thus provides easy means for selection. One preferred vector is pBO475, described in Example 1 of a great grandparent to this application (U.S. Ser. No. 07/428,066 filed Oct. 26, 1989). This vector contains origins of replication for phage and *E. coli* that allow it to be shuttled between such hosts, thereby facilitating mutagenesis and expression. "Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

"Operably linked" when describing the relationship between two DNA or polypeptide regions simply means that they are functionally related to each other. For example, a presequence is operably linked to a peptide if it functions as a signal sequence, participating in the secretion of the mature form of the protein, most probably involving cleavage of the signal sequence. A promoter is operably linked to a coding sequence if it controls the transcription of the sequence; a ribosome binding site is operably linked to a coding sequence if it is positioned so as to permit translation.

Once the hGH is cloned, site-specific mutagenesis (Carter et al., *Nucl. Acids. Res.,* 13: 4331 [1986]; Zoller et al., *Nucl. Acids Res.,* 10: 6487 [1987]), cassette mutagenesis (Wells et al., *Gene,* 34, 315 [1985]), restriction selection mutagenesis (Wells et al., *Philos. Trans. R. Soc. London SerA,* 317: 415 [1986]), or other known techniques may be performed on the cloned hGH DNA to produce the variant DNA that encodes for the changes in amino acid sequence defined by the residues being substituted. When operably linked to an appropriate expression vector, active-domain-substituted hGH variants are obtained. In some cases, recovery of the hGH variant may be facilitated by expressing and secreting such molecules from the expression host by use of an appropriate signal sequence operably linked to the DNA sequence encoding the hGH parent or variant. Such methods are well known to those skilled in the art. Of course, other methods may be employed to produce such polypeptides such as the in vitro chemical synthesis of the desired hGH variant. Barany et al. in *The Peptides,* eds. E. Gross and J. Meienhofer (Academic Press: N.Y. 1979), Vol. 2, pp. 3–254.

Once the different GH variants are produced, they are contacted with the receptor and the interaction, if any, between the receptor and each variant is determined. These activities are compared to the activity of the wild-type hGH with the same receptor to determine which of the amino acid residues in the active domain are involved in the interaction with the receptor. The scanning amino acid used in such an analysis may be any different amino acid from that substituted, i.e., any of the 19 other naturally occurring amino acids.

The target receptor may be isolated from natural sources or prepared by recombinant methods by procedures known in the art. By way of illustration, the receptor may be prepared by the technique described by McFarland et al., *Science,* 245: 494–499 (1989).

The interaction between the receptor and parent and variant can be measured by any convenient in vitro or in vivo assay. Thus, in vitro assays may be used to determine any detectable interaction between a receptor and hGH. Such detection may include the measurement of colorimetric changes, changes in radioactivity, changes in solubility, changes in molecular weight as measured by gel electrophoresis, and/or gel exclusion methods, etc. In vivo assays include, but are not limited to, assays to detect physiological effects, e.g., weight gain or change in electrolyte balance. Generally, any in vivo assay may be used so long as a variable parameter exists so as to detect a change in the interaction between the receptor and the hGH of interest.

While any number of analytical measurements may be used to compare activities, a convenient one for binding of receptor is the dissociation constant $K_d$ of the complex formed between the hGH variant and receptor as compared to the $K_d$ for the wild-type hGH. Generally, a two-fold increase or decrease in $K_d$ per analogous residue substituted by the substitution indicates that the substituted residue(s) is active in the interaction of the wild-type hGH with the target.

When a suspected or known active amino acid residue is subjected to scanning amino acid analysis, the amino acid residues immediately adjacent thereto should be scanned. Three residue-substituted polypeptides can be made. One contains a scanning amino acid, preferably alanine, at position N which is the suspected or known active amino acid. The two others contain the scanning amino acid at position N+1 and N−1. If each substituted hGH causes a greater than about two-fold effect on $K_d$ for the receptor, the scanning amino acid is substituted at position N+2 and N−2. This is repeated until at least one, and preferably four, residues are identified in each direction which have less than about a two-fold effect on $K_d$ or either of the ends of the wild-type hGH are reached. In this manner, one or more amino acids along a continuous amino acid sequence which are involved in the interaction with the particular receptor can be identified.

The active amino acid residue identified by amino acid scan is typically one that contacts the receptor target directly. However, active amino acids may also indirectly contact the target through salt bridges formed with other residues or small molecules such as $H_2O$ or ionic species such as $Na^+$, $Ca^{+2}$, $Mg^{+2}$, or $Zn^{+2}$.

In some cases, the substitution of a scanning amino acid at one or more residues results in a residue-substituted polypeptide which is not expressed at levels which allow for the isolation of quantities sufficient to carry out analysis of its activity with the receptor. In such cases, a different scanning amino acid, preferably an isosteric amino acid, can be used.

Among the preferred scanning amino acids are relatively small, neutral amino acids. Such amino acids include alanine, glycine, serine, and cysteine. Alanine is the preferred scanning amino acid among this group because it eliminates the side-chain beyond the beta-carbon and is less likely to alter the main-chain conformation of the variant. Alanine is also preferred because it is the most common amino acid. Further, it is frequently found in both buried and exposed positions. Creighton, *The Proteins* (W. H. Freeman & Co., N.Y.); Chothia, *J. Mol. Biol.*, 150: 1 (1976). If alanine substitution does not yield adequate amounts of hGH variant, an isosteric amino acid can be used. Alternatively, the following amino acids in decreasing order of preference may be used: Ser, Asn, and Leu.

Once the active amino acid residues are identified, isosteric amino acids may be substituted. Such isosteric substitutions need not occur in all instances and may be performed before any active amino acid is identified. Such isosteric amino acid substitution is performed to minimize the potential disruptive effects on conformation that some substitutions can cause. Isosteric amino acids are shown in the table below:

| Polypeptide Amino Acid | Isosteric Scanning Amino Acid |
|---|---|
| Ala (A) | Ser, Gly |
| Glu (E) | Gln, Asp |
| Gln (Q) | Asn, Glu |
| Asp (D) | Asn, Glu |
| Asn (N) | Ala, Asp |
| Leu (L) | Met, Ile |
| Gly (G) | Pro, Ala |
| Lys (K) | Met, Arg |
| Ser (S) | Thr, Ala |
| Val (V) | Ile, Thr |
| Arg (R) | Lys, Met, Asn |
| Thr (T) | Ser, Val |
| Pro (P) | Gly |
| Ile (I) | Met, Leu, Val |
| Met (M) | Ile, Leu |
| Phe (F) | Tyr |
| Tyr (Y) | Phe |
| Cys (C) | Ser, Ala |
| Trp (W) | Phe |
| His (H) | Asn, Gln |

The method herein can be used to detect active amino acid residues within different active domains. Once this identification is made, various modifications to the wild-type hGH may be made to modify the interaction between the parent hGH and one or more of the targets.

For hGH in particular, exemplary of the present invention is a preferred embodiment wherein the active domains and active residues which determine its activity with its somatogenic receptor (hGHbp) are identified. In carrying out this embodiment of the invention, hGH variants, including amino-acid-residue substituted hGH variants, have been made or identified which have different binding interactions with hGHbp as compared to naturally occurring hGH. Some may have a higher affinity for hGHbp and enhanced potency for somatogenesis in rats. Others have a decreased activity with hGHbp. Such hGH variants are useful as hGH agonists or antagonists and may have a higher potency for stimulating other receptors for hGH, if such variants will be freed from substantial interaction with hGHbp. Further, such variants are useful in immunoassays for hGH as an hGH standard or tracer. Some variants may be identified which have a significant decrease in reactivity with human and mouse serum containing anti-hGH polyclonal antibodies. Others have the same binding affinity for hGHbp as hGH but increased potency to stimulate growth.

The method for determining the active domains and residues for hGH that interact with its somatogenic receptor from liver is shown schematically in FIG. 1, and the segments selected are shown in FIG. 2, of a great grandparent to this application (U.S. Ser. No. 07/428,066 filed Oct. 26, 1989).

Phagemid-Display Method

Additionally, the variants may be analyzed by phagemid display. This method involves (a) constructing a replicable expression vector comprising a first gene encoding the hGH, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a hGH receptor molecule (hGHbp) so that at least a portion of the phagemid particles bind to the receptor molecule; and (g) separating the phagemid particles that bind from those that do not. Preferably, the method further comprises transforming suitable host cells with recombinant phagemid particles that bind to the hGHbp and repeating steps (d) through (g) one or more times.

Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%.

Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Also, normally the method will employ a helper phage selected from M13K07, M13R408, M13-VCS, and Phi X 174. The preferred helper phage is M13K07, and the preferred coat protein is the M13 Phage gene III coat protein. The preferred host is *E. coli*, and protease-deficient strains of *E. coli*. Novel hGH variants selected by the method of the present invention have been detected. Phagemid expression vectors were constructed that contain a suppressible termination codon functionally located between the nucleic acids encoding the polypeptide and the phage coat protein.

In detail, repeated cycles of hGH selection are used to select for higher and higher affinity binding by the phagemid selection of multiple amino acid changes which are selected by multiple selection cycles. Following a first round of phagemid selection, involving a first region or selection of amino acids in the ligand polypeptide, additional rounds of phagemid selection in other regions or amino acids of the ligand polypeptide are conducted. The cycles of phagemid selection are repeated until the desired affinity properties of the ligand polypeptide are achieved. To illustrate this process, phagemid selection of hGH was conducted in cycles. In the fist cycle hGH amino acids 172, 174, 176, and 178 can be mutated and phagemid selected. In a second cycle hGH amino acids 167, 171, 175, and 179 can be phagemid selected. In a third cycle hGH amino acids 10, 14, 18, and 21 can be phagemid selected. Optimum amino acid changes from a previous cycle may be incorporated into the polypeptide before the next cycle of selection. For example, hGH amino acids substitutions 174 (serine) and 176 (tyrosine) were incorporated into the hGH before the phagemid selection of hGH amino acids 167, 171, 175, and 179.

From the foregoing it will be appreciated that the amino acid residues that form the binding domain of the hGH will not be sequentially linked and may reside on different subunits of the polypeptide. That is, the binding domain tracks with the particular secondary structure at the binding site and not the primary structure. Thus, generally, mutations will be introduced into codons encoding amino acids within a particular secondary structure at sites directed away from the interior of the polypeptide so that they will have the potential to interact with the receptor. The location of residues in hGH that strongly modulate its binding to the hGH receptor (Cunningham et al., *Science*, 1990, supra) are known. Hence, representative sites suitable for mutagenesis would include residues 172, 174, 176, and 178 on helix-4, as well as residue 64 located in a "non-ordered" secondary structure.

In this phagemid-display method, once the hGH gene has been isolated, it may be inserted into a suitable vector (preferably a plasmid) for amplification, as described generally by Sambrook et al., *Molecular Biology: A Laboratory Manual*, Cold Spring Harbor Press, Cold Spring Harbor, N.Y. 1989. While several types of vectors are available and may be used to practice this invention, plasmid vectors are the preferred vectors for use herein, as they may be constructed with relative ease, and can be readily amplified. Plasmid vectors generally contain a variety of components, including promoters, signal sequences, phenotypic selection genes, origin of replication sites, and other necessary components as are known to those of ordinary skill in the art.

Promoters most commonly used in prokaryotic vectors include the lac Z promoter system, the alkaline phosphatase pho A promoter, the bacteriophage $\lambda_{PL}$ promoter (a temperature-sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al., supra. While these are the most commonly used promoters, other suitable microbial promoters may be used as well.

Preferred promoters for practicing this invention for phagemid display are those that can be tightly regulated such that expression of the fusion gene can be controlled. It is believed that the problem that went unrecognized in the prior art was that display of multiple copies of the fusion protein on the surface of the phagemid particle lead to multipoint attachment of the phagemid with the target. This effect, referred to as the "chelate effect," is believed to result in selection of false "high affinity" polypeptides when multiple copies of the fusion protein are displayed on the phagemid particle in close proximity to one another so that the target was "chelated." When multipoint attachment occurs, the effective or apparent $K_d$ may be as high as the product of the individual $K_d$s for each copy of the displayed fusion protein.

It has been discovered that by tightly regulating expression of the fusion protein so that no more than a minor amount, i.e., fewer than about 1%, of the phagemid particles contain multiple copies of the fusion protein, the "chelate effect" is overcome, allowing proper selection of high-affinity polypeptides. Thus, depending on the promoter, culturing conditions of the host are adjusted to maximize the number of phagemid particles containing a single copy of the fusion protein and minimize the number of phagemid particles containing multiple copies of the fusion protein.

Preferred promoters used to practice this invention are the lac Z promoter and the pho A promoter. The lac Z promoter is regulated by the lac repressor protein lac i, and thus transcription of the fusion gene can be controlled by manipulation of the level of the lac repressor protein. By way of illustration, the phagemid containing the lac Z promoter is grown in a cell strain that contains a copy of the lac i repressor gene, a repressor for the lac Z promoter. Exemplary cell strains containing the lac i gene include JM 101 and XL1-blue. In the alternative, the host cell can be cotransfected with a plasmid containing both the repressor lac i and the lac Z promoter. Occasionally both of the above techniques are used simultaneously, that is, phagemid particles containing the lac Z promoter are grown in cell strains containing the lac i gene and the cell strains are cotransfected with a plasmid containing both the lac Z and lac i genes.

Normally when one wishes to express a gene, to the transfected host above one would add an inducer such as isopropylthiogalactoside (IPTG). In the present invention, however, this step is omitted to (a) minimize the expression of the gene III fusion protein, thereby minimizing the copy number (i.e., the number of gene III fusions per phagemid number) and to (b) prevent poor or improper packaging of the phagemid caused by inducers such as IPTG even at low concentrations. Typically, when no inducer is added, the number of fusion proteins per phagemid particle is about 0.1 (number of bulk fusion proteins/number of phagemid particles). The most preferred promoter used to practice this invention is pho A. This promoter is believed to be regulated by the level of inorganic phosphate in the cell where the phosphate acts to down-regulate the activity of the promoter. Thus, by depleting cells of phosphate, the activity of the promoter can be increased. The desired result is achieved by growing cells in a phosphate-enriched medium such as 2YT or LB, thereby controlling the expression of the gene III fusion.

One other useful component of vectors used to practice this invention is a signal sequence. This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, lamb or ompF (Wong et al., *Gene*, 68: 193 [1983]), MalE, PhoA, and other genes. A preferred prokaryotic signal sequence for practicing this invention is the *E. coli* heat-stable enterotoxin II (STII) signal sequence as described by Chang et al., supra.

Another useful component of the vectors used to practice the phage-display method is phenotypic selection genes. Typical phenotypic selection genes are those encoding proteins that confer antibiotic resistance upon the host cell. By way of illustration, the ampicillin resistance gene (amp) and the tetracycline resistance gene (tet) are readily employed for this purpose.

Construction of suitable vectors comprising the aforementioned components as well as the gene encoding the hGH (gene 1) are prepared using standard recombinant DNA procedures as described in Sambrook et al., supra. Isolated DNA fragments to be combined to form the vector are cleaved, tailored, and ligated together in a specific order and orientation to generate the desired vector.

The DNA is cleaved using the appropriate restriction enzyme or enzymes in a suitable buffer. In general, about 0.2–1 µg of plasmid or DNA fragments is used with about 1–2 units of the appropriate restriction enzyme in about 20 µl of buffer solution. Appropriate buffers, DNA concentrations, and incubation times and temperatures are specified by the manufacturers of the restriction enzymes. Generally, incubation times of about one or two hours at 37° C. are adequate, although several enzymes require higher temperatures. After incubation, the enzymes and other contaminants are removed by extraction of the digestion solution with a mixture of phenol and chloroform, and the DNA is recovered from the aqueous fraction by precipitation with ethanol.

To ligate the DNA fragments together to form a functional vector, the ends of the DNA fragments must be compatible with each other. In some cases, the ends will be directly compatible after endonuclease digestion. However, it may be necessary to first convert the sticky ends commonly produced by endonuclease digestion to blunt ends to make them compatible for ligation. To blunt the ends, the DNA is treated in a suitable buffer for at least 15 minutes at 15° C. with 10 units of the Klenow fragment of DNA polymerase I (Klenow) in the presence of the four deoxynucleotide triphosphates. The DNA is then purified by phenol-chloroform extraction and ethanol precipitation.

The cleaved DNA fragments may be size-separated and selected using DNA gel electrophoresis. The DNA may be electrophoresed through either an agarose or a polyacrylamide matrix. The selection of the matrix will depend on the size of the DNA fragments to be separated. After electrophoresis, the DNA is extracted form the matrix by electroelution, or, if low-melting agarose has been used as the matrix, by melting the agarose and extracting the DNA from it, as described in sections 6.30–6.33 of Sambrook et al., supra.

The DNA fragments that are to be ligated together (previously digested with the appropriate restriction enzymes such that the ends of each fragment to be ligated are compatible) are put in solution in about equimolar amounts. The solution will also contain ATP, ligase buffer, and a ligase such as T4 DNA ligase at about 10 units per 0.5 µg of DNA. If the DNA fragment is to be ligated into a vector, the vector is at first linearized by cutting with the appropriate restriction endonuclease(s). The linearized vector is then treated with alkaline phosphatase or calf intestinal phosphatase. The phosphatasing prevents self-ligation of the vector during the ligation step.

After ligation, the vector with the foreign gene now inserted is transformed into a suitable host cell. Prokaryotes are the preferred host cells for this invention. Suitable prokaryotic host cells include *E. coli* strain JM101, *E. coli* K12 strain 294 (ATCC number 31,446), *E. coli* strain W3110 (ATCC number 27,325), *E. coli* X1776 (ATCC number 31,537), *E. coli* XL-1Blue (Stratagene), and *E. coli* B; however, many other strains of *E. coli*, such as HB101, NM522, NM538, and NM539, and many other species and genera of prokaryotes may be used as well. In addition to the *E. coli* strains listed above, bacilli such as *Bacillus subtilis*, other enterobacteriaceae such as *Salmonella typhimurium* or *Serratia marcescens*, and various *Pseudomonas* species may all be used as hosts.

Transformation of prokaryotic cells is readily accomplished using the calcium chloride method as described in section 1.82 of Sambrook et al., supra. Alternatively, electroporation (Neumann et al., *EMBO J.*, 1: 841 [1982]) may be used to transform these cells. The transformed cells are selected by growth on an antibiotic, commonly tet or amp, to which they are rendered resistant due to the presence of tet and/or amp resistance genes on the vector.

After selection of the transformed cells, these cells are grown in culture and the plasmid DNA (or other vector with the foreign gene inserted) is then isolated. Plasmid DNA can be isolated using methods known in the art. Two suitable methods are the small-scale preparation of DNA and the large-scale preparation of DNA as described in sections 1.25–1.33 of Sambrook et al., supra. The isolated DNA can be purified by methods known in the art such as that described in section 1.40 of Sambrook et al., supra. This purified plasmid DNA is then analyzed by restriction mapping and/or DNA sequencing. DNA sequencing is generally performed by either the method of Messing et al., *Nucleic Acids Res.*, 9: 309 (1981), the method of Maxam et al., *Meth. Enzymol.*, 65: 499 (1980), or the method of Sanger et al., *Proc. Natl. Acad. Sci. USA*, 74: 5463–5467 (1977).

The phagemid-display method herein contemplates fusing the gene encoding the hGH (gene 1) to a second gene (gene 2) such that a fusion protein is generated during transcription. Gene 2 is typically a coat protein gene of a phage, and preferably it is the phage M13 gene III coat protein, or a fragment thereof. Fusion of genes 1 and 2 may be accomplished by inserting gene 2 into a particular site on a plasmid that contains gene 1, or by inserting gene 1 into a particular site on a plasmid that contains gene 2.

Insertion of a gene into a plasmid requires that the plasmid be cut at the precise location that the gene is to be inserted. Thus, there must be a restriction endonuclease site at this location (preferably a unique site such that the plasmid will only be cut at a single location during restriction endonuclease digestion). The plasmid is digested, phosphatased, and purified as described above. The gene is then inserted into this linearized plasmid by ligating the two DNAs together. Ligation can be accomplished if the ends of the plasmid are compatible with the ends of the gene to be inserted. If the restriction enzymes are used to cut the plasmid and isolate the gene to be inserted to create blunt ends or compatible sticky ends, the DNAs can be ligated together directly with a ligase such as bacteriophage T4 DNA ligase by incubating the mixture at 16° C. for 1–4 hours in the presence of ATP and ligase buffer as described in section 1.68 of Sambrook et al., supra. If the ends are not compatible, they must first be made blunt by using the Klenow fragment of DNA polymerase I or bacteriophage T4 DNA polymerase, both of which require the four deoxyribonucleotide triphosphates to fill in overhanging single-stranded ends of the digested DNA.

Alternatively, the ends may be blunted using a nuclease such as nuclease S1 or mung-bean nuclease, both of which function by cutting back the overhanging single strands of DNA. The DNA is then religated using a ligase as described above. In some cases, it may not be possible to blunt the ends of the gene to be inserted, as the reading frame of the coding region will be altered. To overcome this problem, oligonucleotide linkers may be used. The linkers serve as a bridge to connect the plasmid to the gene to be inserted. These linkers can be made synthetically as double-stranded or single-stranded DNA using standard methods. The linkers have one end that is compatible with the ends of the gene to be inserted; the linkers are first ligated to this gene using ligation methods described above. The other end of the linkers is designed to be compatible with the plasmid for ligation. In designing the linkers, care must be taken not to destroy the reading frame of the gene to be inserted or the reading frame of the gene contained on the plasmid. In some cases, it may be necessary to design the linkers such that they code for part of an amino acid, or such that they code for one or more amino acids.

Between gene 1 and gene 2, DNA encoding a termination codon may be inserted, such termination codons being UAG (amber), UAA (ocher), and UGA (opel). Davis et al., *Microbiology* (Harper and Row: New York, 1980), pages 237, 245–247, and 274. The termination codon expressed in a wild-type host cell results in the synthesis of the gene 1 protein product without the gene 2 protein attached. However, growth in a suppressor host cell results in the synthesis of detectable quantities of fused protein. Such suppressor host cells contain a tRNA modified to insert an amino acid in the termination codon position of the mRNA, thereby resulting in production of detectable amounts of the fusion protein. Such suppressor host cells are well known and described, such as *E. coli* suppressor strain. Bullock et al., *BioTechniques*, 5: 376–379 (1987). Any acceptable method may be used to place such a termination codon into the mRNA encoding the fusion polypeptide.

The suppressible codon may be inserted between the hGH gene and a second gene encoding at least a portion of a phage coat protein. Alternatively, the suppressible termination codon may be inserted adjacent to the fusion site by replacing the last amino acid triplet in the polypeptide or the first amino acid in the phage coat protein. When the phagemid containing the suppressible codon is grown in a suppressor host cell, it results in the detectable production of a fusion polypeptide containing the hGH and the coat protein. When the phagemid is grown in a non-suppressor host cell, the hGH is synthesized substantially without fusion to the phage coat protein due to termination at the inserted suppressible triplet encoding UAG, UAA, or UGA. In the non-suppressor cell the polypeptide is synthesized and secreted from the host cell due to the absence of the fused phage coat protein which otherwise anchored it to the host cell.

The hGH gene may be altered at one or more selected codons. An alteration is defined as a substitution, deletion, or insertion of one or more codons in the gene encoding the hGH that results in a change in the amino acid sequence of the hGH as compared with the unaltered or native sequence of the hGH. Preferably, the alterations will be by substitution of at least one amino acid with any other amino acid in one or more regions of the molecule. The alterations may be produced by a variety of methods known in the art. These methods include, but are not limited to, oligonucleotide-mediated mutagenesis and cassette mutagenesis.

Oligonucleotide-mediated mutagenesis is the preferred method for preparing substitution, deletion, or insertion variants of hGH. The technique is well known in the art as described by Zoller et al., supra. Briefly, the hGH gene is altered by hybridizing an oligonucleotide encoding the desired mutation to a DNA template, where the template is the single-stranded form of the plasmid containing the unaltered or native DNA sequence for hGH. After hybridization, a DNA polymerase is used to synthesize an entire second complementary strand of the template, and thus will incorporate the oligonucleotide primer and will code for the selected alteration in the hGH gene.

Generally, oligonucleotides of at least 25 nucleotides in length are used. Although smaller oligonucleotides can be employed, an optimal oligonucleotide will have 12 to 15 nucleotides that are complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA*, 75: 5765 (1978).

The DNA template can only be generated by those vectors that are either derived from bacteriophage M13 vectors (the commercially available M13mp18 and M13mp19 vectors are suitable), or those vectors that contain a single-stranded phage origin of replication as described by Vieira and Messing, *Meth. Enzymol.*, 153: 3–11 (1987). Thus, the DNA that is to be mutated must be inserted into one of these vectors in order to generate single-stranded template. Production of the single-stranded template is described in sections 4.21–4.41 of Sambrook et al., supra.

To alter the native DNA sequence, the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the hGH gene, and the other strand (the original template) encodes the native, unaltered sequence of the hGH gene. This heteroduplex molecule is then transformed into a suitable host cell, usually a prokaryote such as *E. coli* JM101. After the cells are grown, they are plated onto agarose plates and screened using the oligonucleotide primer radiolabeled with 32-Phosphate to identify the bacterial colonies that contain the mutated DNA.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(AS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

Mutants with more than one amino acid to be substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized form the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Cassette mutagenesis is also a preferred method for preparing substitution, deletion, and insertion variants of hGH DNA. The method is based on that described by Wells et al., *Gene,* supra. The starting material is the plasmid (or other vector) comprising the hGH gene to be mutated. The codon(s) in the hGH gene to be mutated are identified. Optimally, there is a unique restriction endonuclease site on each side of the identified mutation site(s); however, this is not a requirement. If no such restriction sites exist, they may be generated using the above-described oligonucleotide-mediated mutagenesis method to introduce them at appropriate locations in the hGH gene. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence of hGH.

For preparing the receptor molecule and binding it with the phagemid, the purified receptor is attached to a suitable matrix such as agarose beads, acrylamide beads, glass beads, cellulose, various acrylic copolymers, hydroxyalkyl methacrylate gels, polyacrylic acid, polymethacrylic copolymers, nylon, neutral and ionic carriers, and the like. Attachment of the receptor to the matrix may be accomplished by methods described in *Meth. Enzymol.*, 44: (1976), or by other means known in the art.

After attachment of the receptor to the matrix, the immobilized target is contacted with the library of phagemid particles under conditions suitable for binding of at least a portion of the phagemid particles with the immobilized target. Normally, the conditions, including pH, ionic strength, temperature, and the like will mimic physiological conditions.

Bound phagemid particles ("binders") having high affinity for the immobilized receptor are separated from those having a low affinity (and thus do not bind to the target) by washing. Binders may be dissociated from the immobilized target by a variety of methods. These methods include competitive dissociation using the wild-type ligand, altering pH and/or ionic strength, and methods known in the art.

Suitable host cells are infected with the binders and helper phage, and the host cells are cultured under conditions suitable for amplification of the phagemid particles. The phagemid particles are then collected and the selection process is repeated one or more times until binders having the desired affinity for the target molecule are selected.

Optionally, the library of phagemid particles may be sequentially contacted with more than one immobilized receptor to improve selectivity for a particular receptor. Thus, hGH has more than one natural receptor: the GH receptor and the prolactin receptor. It may be desirable to improve the selectivity of hGH for the GH receptor over the prolactin receptor. This can be achieved by first contacting the library of phagemid particles with immobilized GH receptor, allowing binding to occur in the presence of a very high concentration of prolactin receptor in solution, and selecting for binders. In this case, an hGH mutant having a lower affinity for the prolactin receptor would have therapeutic utility even if the affinity for the GH receptor were somewhat lower than that of wild-type hGH.

Therapeutic Formulations

Therapeutic formulations of the hGH variants herein for therapeutic administration are prepared for storage by mixing the hGH variants having the desired degree of purity with optional physiologically acceptable carriers, excipients, or stabilizers (*Remington's Pharmaceutical Sciences,* 16th edition, Oslo, A., Ed., [1980]) in the form of lyophilized cake or aqueous solutions. Parenteral formulations can be prepared by mixing the hGH in a unit dosage injectable form (solution, suspension, or emulsion) with a pharmaceutically acceptable carrier. Pharmaceutically acceptable carriers, excipients, or stabilizers are non-toxic to recipients at the dosages and concentrations employed, and are compatible with other ingredients of the formulation. For example, the formulation preferably does not include oxidizing agents and other compounds known to be deleterious to polypeptides.

Suitable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates, including glucose, mannose, or dextrins; chelating agents such as EDTA; divalent metal ions such as zinc, cobalt, or copper; sugar alcohols such as mannitol or sorbitol; salt-forming counterions such as sodium; and/or nonionic surfactants such as Tween, Pluronics, or polyethylene glycol (PEG).

Additionally, the hGH variants herein may be covalently attached to PEG molecules at one or more amino acids, including at lysine residues, as disclosed in WO 93/00109, supra.

Formulations of the present invention may additionally contain a pharmaceutically acceptable buffer, amino acid, bulking agent, and/or non-ionic surfactant. These include, for example, buffers, chelating agents, antioxidants, preservatives, cosolvents, and the like; specific examples of these could include trimethylamine salts (Tris buffer) and disodium edetate. The phagemids of the present invention may be used to produce quantities of the hGH variants free of the phage protein. To express hGH variants free of the phage protein gene, pSO643 and derivatives can simply be grown in a non-suppressor strain such as 16C9. In this case, the amber codon (TAG) leads to termination of translation, which yields free hormone, without the need for an independent DNA construction. The hGH variant is secreted from the host and may be isolated from the culture medium.

Additionally, the GH formulation set forth in WO 89/09614 may be employed wherein the hGH variant is contained in a composition comprising glycine, mannitol and a buffer such as a phosphate buffer, or is contained in a liquid formulation comprising 0.1 to 5% (w/v) of a non-ionic surfactant such as polysorbate or a poloxamer that does not necessarily contain mannitol or glycine.

The hGH variant is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (U. Sidman et al., *Biopolymers*, 22, 547–556 (1983)), poly(2-hydroxyethyl methacrylate) (Langer et al., *J. Biomed. Mater. Res.*, 15: 167–277 [1981]; Langer, *Chem. Tech.*, 12: 98–105 [1982]), ethylene vinyl acetate (Langer et al., supra) or poly-D-(−)-3-hydroxybutyric acid (EP 133,988). Sustained-release hGH variant compositions also include liposomally entrapped hGH variants. Liposomes containing hGH variants are prepared by methods known per se: DE 3,218,121; Epstein et al., *Proc. Natl. Acad. Sci. U.S.A.*, 82: 3688–3692 (1985); Hwang et al., *Proc. Natl. Acad. Sci. U.S.A.*, 77: 4030–4034 (1980); EP 52,322; EP 36,676; EP 88,046; EP 143,949; EP 142,641; Japanese Pat. Appln. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal hGH variant therapy.

The hGH variant to be used for therapeutic administration must be sterile. Sterility is readily accomplished by filtration through sterile filtration membranes (e.g., 0.2 micron membranes).

Therapeutic hGH variant compositions generally are placed into a container having a sterile access port, for example, an intravenous solution bag or vial having a stopper pierceable by a hypodermic injection needle.

hGH variants ordinarily will be stored in unit or multidose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous hGH variant solution, and the resulting mixture is lyophilized. The infusion solution is prepared by reconstituting the lyophilized hGH variant using bacteriostatic Water-for-Injection.

Therapeutic Uses

The hGH variants herein may act as agonists or antagonists of hGH. For example, as antagonists they may be useful in treating conditions of GH excess such as acromegaly. They may be useful as agonists in increasing the anabolism or growth of a mammal. Growth refers to the dynamics of statural growth experienced by an individual during infancy, childhood, and adolescence as depicted by a normal growth curve. Thus, growth herein refers to the growth of linear-producing bone plate driven by chondrocytes, as distinguished from the growth of osteoblast cells, derived from a different part of the bone. Restoration of normal growth patterns would allow the patient to approach a more satisfactory growth curve. Examples of patients that are relatively resistant to GH but require treatment to induce an anabolic effect include those with Turner's Syndrome, GH-deficient children, children who experience a slowing or retardation in their normal growth curve about 2–3 years before their growth plate closes, that is, so-called short normal children, and patients where the IGF-I response to GH has been blocked chemically (i.e., by glucocorticoid treatment) or by a natural condition such as in adult patients where the IGF-I response to GH is naturally reduced.

Another condition that can be treated by agonists is an immune disorder. The GH variant may act to stimulate the immune system of a mammal by increasing its immune function, whether the increase is due to antibody mediation or cell mediation, and whether the immune system is endogenous to the host treated with the hGH variant or is transplanted from a donor to the host recipient given the hGH (such as bone marrow transplants). For example, the stimulation may result from an increased number of splenic cells such as splenic lymphocyte number, splenic T-cell population number (T-cell, $CD_4$ and $CD_8$), or splenic B-cell number, or from an increased number of thymocytes. Other cells involved in the immune system response include natural killer cells, macrophages, and neutrophils. In addition, the stimulation may be due to an increase in antibody production in response to an immunogen.

The expressions "compromised immune system" and "condition in which insufficient immunoglobulin production occurs" signify the immune system of humans as well as animals that have a smaller antibody response to antigens than normal, whether because their spleen size is smaller than it should be, whether the spleen is only partially functional, whether drugs such as chemotherapeutic agents are suppressing the normal immune function, whether the animal is functionally IGF-I- (or GH-) deficient, or due to any other factor. Examples include aged patients, patients undergoing chemotherapy or radiation therapy, recovering from a major illness, or about to undergo surgery, patients with AIDS, patients with congenital and acquired B-cell deficiencies such as hypogammaglobulinemia, common varied agammaglobulinemia, and selective immunoglobulin deficiencies, e.g., IgA deficiency, patients infected with a virus such as rabies with an incubation time shorter than the immune response of the patient, and patients with hereditary disorders such as diGeorge syndrome.

It is also known that hGH has a role in the development and progression of breast cancer in the experimental animal. Tornell et al., *Int. J. Cancer,* 49: 114 (1991). For example, a high serum level of GH was found to induce the formation of breast cancer, while reduction of the circulating level of GH correlated with the regression of breast cancer. Phares et al., *Anticancer Res.,* 6: 845 (1986). Thus, the hGH variants herein may inhibit the growth of cells expressing prolactin receptors, for example breast cancer cells, in a method comprising contacting the cells with an effective amount of the hGH variant, wherein the variant is an antagonist that binds to the prolactin receptor.

For the various purposes of this invention, the hGH variant is directly administered to the mammal by any suitable technique, including parenterally, and can be administered locally or systemically. The specific route of administration will depend, e.g., on the medical history of the patient, including any perceived or anticipated side effects using the hGH variant. Examples of parenteral administration include subcutaneous, intramuscular, intravenous, intraarterial, and intraperitoneal administration.

Most preferably, the administration is by continuous infusion (using, e.g., minipumps such as osmotic pumps), or by injection using, e.g., intravenous or subcutaneous means. Preferably, the administration is subcutaneous for the hGH variant. The administration may also be as a single bolus or by slow-release depot formulation.

The hGH variant composition to be used in the therapy will be formulated and dosed in a fashion consistent with good medical practice, taking into account the specific condition being treated, the clinical condition of the individual patient (especially the side effects of treatment with hGH variant alone), the site of delivery of the hGH variant composition, the method of administration, the scheduling of administration, and other factors known to practitioners. The "effective amount" of hGH variant for purposes herein (including an immune- and growth-stimulating effective amount and an antagonist effective amount to counteract, e.g., acromegaly) is thus determined by such considerations.

As a general proposition, the total pharmaceutically effective amount of the hGH variant administered parenterally per dose will be in the range of about 1 µg/kg/day to 100 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the hGH variant is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The key factor in selecting an appropriate dose is the result obtained, as measured, for example, by reduction in tumor growth and increases in long bone growth, antibody production, splenocyte or thymocyte number, splenic B-cells, reduction in serum GH, etc.

The mammals potentially treatable by the hGH variants herein include mammals of economic importance such as bovine, ovine, and porcine animals. The preferred mammal herein is a human.

The following is presented by way of example and is not to be construed as a limitation to the scope of the invention. All citations used herein are expressly incorporated herein by reference.

EXAMPLE I

The kinetics and affinity of binding for alanine substitutions at 30 contact residues in Site 1 of hGH were evaluated. A biosensor device, called a BIAcore™ biosensor, was used that relies upon surface plasmon resonance to measure changes in refractive index upon hormone binding to an immobilized receptor. In this example it was found that affinity is dominated by less than one-quarter of the 31 contact side-chains, and these cluster in a small patch near the center of the contact epitope. Thus, the "structural epitope" is considerably larger than the "functional binding epitope."

Experimental Protocol

Alanine mutations of residues buried at Site 1 in hGH were available from the work described in Cunningham and Wells, supra, or newly made by site-directed mutagenesis. Kunkel et al., *Methods Enzymol.,* 154: 367–382 (1987). Variant proteins were produced and purified as described in Cunningham and Wells, supra. Yields were improved by extending the duration of the ammonium sulphate precipitations to one hour.

hGHbp (Wells and De Vos, supra) was immobilized on the Pharmacia BIAcore™ biosensor and changes in refractive index upon binding of hormone were used for kinetic measurements. The association and dissociation constants were calculated using software provided with the instrument. Karlsson et al., *J. Immunol. Methods,* 145: 229–240 (1991). The hGHbp was immobilized in discrete orientations on the sensor chip by fixing the hGHbp via a free thiol. This was accomplished by introducing a cysteine residue at one of two specific sites (S201C or S237C) using site-directed mutagenesis (Kunkel et al., supra). The thiol variants of the hGHbp were expressed in *E. coli* and purified to homogeneity. Fuh et al., *J. Biol. Chem.,* 265: 3111–3115 (1990). These proteins were coupled to the chip surface by activating the carboxyl-dextran matrix with N-ethyl-N'-(3-diethylaminopropyl)-carbodiimide (EDC) and reacting it with N-hydroxysuccinimide (NHS). The NHS-ester was reacted with 2-(2-pyridinyldithio)-ethaneamine (PEDA). Remaining unreacted NHS-ester groups were displaced by addition of ethanolamine. The hGHbp variants were reacted with the matrix (at 50 µg/ml in 50 mM sodium acetate, pH 4.5) until approximately 1000 RU's were coupled (1.0 ng/mm$^2$; see the BIAcore™ manual).

Association rates were measured from binding profiles obtained by injecting increasing concentrations of each hGH variant. Five serial dilutions (each 2-fold) were made starting at 200 or 1000 nM hormone depending on the affinity for the hGHbp. A maximum flow rate of 20 μl/min. was applied to minimize potential mass transport effects. High salt buffer (150 mM NaCl, 10 mM sodium phosphate, pH 7.4) was used to prevent long-range electrostatic effects and to mimic physiological ionic strength. Also included was 0.02% Tween 20 to reduce non-specific binding. The matrix was regenerated by washing for 20 seconds with 4.5 M $MgCl_2$. Control experiments showed this was sufficient to remove all the bound hormone, and the matrix could be re-used more than 50 times without significant change in the binding kinetics.

Dissociation rates were measured by saturating the biosensor with 5 μM hGH mutant and switching to buffer without hormone. Buffer flow rates and regeneration conditions were identical to those used to measure the association profiles. Potential rebinding effects were minimized by using only the initial 10 minutes of each dissociation profile for calculation of the dissociation constant. Both association and dissociation constants were determined using the Pharmacia Kinetics Evaluation software to solve the rate equations. Karlsson et al., supra.

The average standard deviation within triplicate determinations of association constants on the same biosensor chip was ±4% of the value reported. Values determined between different biosensor chips vary up to 60%. However, because a wild-type reference was always included, the standard errors for the relative values reported here are the same as determinations made on the same chip. The concentration of hGH and variants was determined by densitometry of Coomassie blue-stained proteins after SDS polyacrylamide gel electrophoresis. This method confirms the purity and integrity of the variant hormones as well as providing a protein concentration independent of the substitution with a precision of ±10%. Cunningham and Wells, supra. Thus, the average cumulative errors in relative association, dissociation, and affinity constants are about 17%, 14%, and 21%, respectively.

derivatized matrix on the BIAcore™ biosensor via a mixed disulfide bond. FIG. 1A. The S237C(hGHbp) mutation does not affect binding affinity to hGH and has been used to attach a single thiol-specific fluorescent probe to follow hGH-induced dimerization of the hGHbp in solution. Cunningham et al., 1991, supra. This attachment ensured uniform orientation of the hGHbp on the matrix unlike that obtained if random coupling through primary amine groups had been used. From the change in refractive index resonance units (RUs) that occurred during the coupling reaction, the amount of attached hGHbp was calculated from calibration curves supplied by Pharmacia (see the BIAcore™ biosensor manual).

When excess hGH was added to the (s237C)hGHbp-matrix, rapid association and extremely slow dissociation was observed. FIG. 1B. From the change in RU, a molar ratio of 0.4 hGH bound per immobilized hGHbp was calculated. See Table 1. This suggested that hGH dimerized the immobilized hGHbp as it did in solution. FIG. 1A. Dimerization on the matrix was further tested by measuring the binding to hGHbp of a non-dimerizing mutant of hGH, (G120R)hGH, which is blocked in its ability to bind Site 2. Fuh et al., 1992, supra. When a saturating level of (G120R)hGH was added, it was found that about twice as much hormone bound (FIG. 1B), with a calculated stoichiometry of 0.7 (G120R)hGH per immobilized hGHbp (Table 1).

Analysis of the on- and off-rate profiles showed that both wild-type and (G120R)hGH associate at similar rates (Table 1). However, the off-rate for the wild-type was too slow to calculate a reliable dissociation constant. These data are consistent with the proposed sequential binding mechanism; that is, both hormones bound in the same way to the first receptor and hence have nearly the same on-rates. However, the wild-type hormone bound to the second receptor and thus was extremely slow to dissociate.

TABLE 1

Kinetic constants for binding of wild-type or (G120R) hGH to (S237C) hGHbp or (S201C) hGHbp immobilized on the thiol-matrix of the BIAcore ™ biosensor. On-rate and off-rate profiles were measured at 25° C. and analyzed for hGH and (G120R) hGH; average standard errors for on-rate, off-rate, and affinities on the same biosensor chip are 17%, 14%, and 21% of the value reported. Stoichiometries of binding were calculated from data in FIGS. 1B and 2B according to the following formula:

$$\frac{RU_{(max)}\text{hormone}}{RU_{(attached)}\text{hGHbp}} \times \frac{MW_{bGHbp}}{MW_{hormone}}$$

| Hormone | Matrix | Stoichiometry (hormone:hGHbp) | On-rate ($s^{-1}M^{-1}$) | Off-rate ($s^{-1}$) | $k_d$ (nM) |
|---|---|---|---|---|---|
| Wild-type | (S237C) hGHbp | 0.40 | $4.0 \times 10^5$ | $<1.0 \times 10^{-5}$ | ND* |
| G120R | (S237C) hGHbp | 0.70 | $2.6 \times 10^5$ | $4.3 \times 10^{-4}$ | 1.6 |
| Wild-type | (S201C) hGHbp | 0.84 | $3.0 \times 10^5$ | $2.7 \times 10^{-4}$ | 0.9 |
| G120R | (S201C) hGHbp | 0.92 | $1.4 \times 10^5$ | $3.7 \times 10^{-4}$ | 2.7 |

*ND = not determined.

Results

Figure 2B:
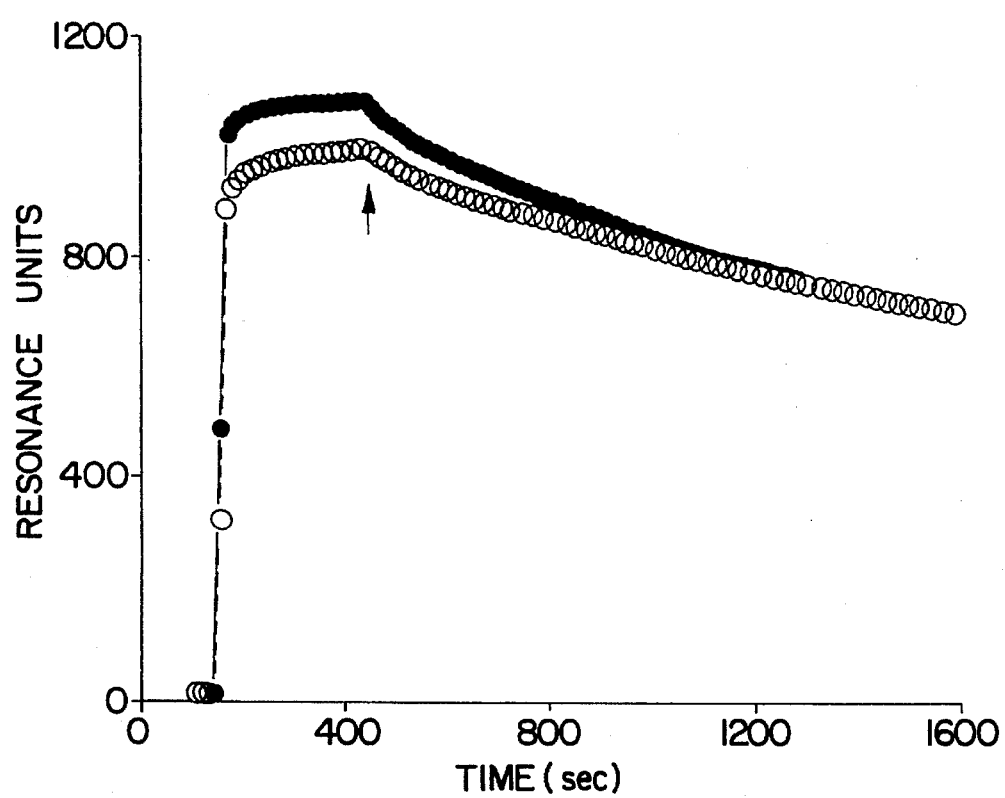

The binding of hGH to the hGHbp was studied by immobilizing a variant of the hGHbp, (S237C)hGHbp [Ser237 is converted to Cys in the hGHbp] to the thiol- It was desired to investigate in greater detail the binding of mutants in the Site 1 contact epitope alone without the complication of the hGHbp dimerizing on the matrix. According to the x-ray structure of the hGH(hGHbp)$_2$ complex (De Vos et al., supra), the two hGHbps contact each other at Ser201. Therefore, dimerization on the matrix was blocked by replacing Ser201 with Cys and attaching the S201C variant via its single thiol to the activated-thiol matrix. FIG. 2A. Indeed, when saturating levels of hGH were added (FIG. 2B), a maximum stoichiometry of 0.84 hGH per immobilized (S201C)hGHbp (Table 1) was calculated. The (G120R)hGH bound with a stoichiometry of 0.94 per (S201C)hGHbp. By proper placement of the thiol-coupling, it was possible to orient the hGHbp on the matrix to allow for either 1:1 complex formation or 1:2 complex formation. Thus, the solution binding properties of hGH for the hGHbp can be reproduced on the BIAcore™ biosensor. The (G120R)hGH had virtually the same kinetics as hGH on the (S201C)hGHbp-matrix and the same as that of (G120R)hGH on the (S237C)hGHbp-matrix (Table 1). Together these data indicate that the (S201C)hGHbp-matrix is a reliable means of testing variants of hGH for binding to Site 1 alone.

A buried side-chain on hGH was defined as one that contains side-chain atoms whose accessibility to solvent changes when bound to the hGHbp at Site 1. Solvent accessibilities were calculated by rolling a 1.4 angstrom radium probe (Lee and Richards, *J. Mol. Biol.*, 55: 379–400 [1971]) over the surface of hGH when free or bound to one hGHbp through Site 1. For these calculations the x-ray coordinate set was used for the hGH(hGHbp)$_2$ complex. De Vos et al., supra. By this criteria there are 30 side-chains, all larger than alanine, which are buried to some degree upon complexation. Table 2.

TABLE 2

Relative on-rates, off-rates and affinities for alanine substitutions at residues in hGH that are buried to varying degrees at the Site 1 interface. Rate measurements were made using the hGHbp (S201C) matrix at 25° C. as described in Table 1.

| Site 1 contact residue | Changes in accessible area upon binding[1] (Å$^2$) | Vdw contacts[2] (H-bonds, h; salt bridges, s) | off-rate | Changes in kinetics from wt[3] 1/on-rate | off/on | ΔΔG (kcal/mol) BIAcore™ (RIA)[4] |
|---|---|---|---|---|---|---|
| Wild-type | — | — | (1) | (1) | (1) | (0) |
| M14 | 0.5 (0.6) | 0 | 1.2 | 1 | 1 | +0.1 (+0.5) |
| H18 | 23 (63) | 24 (hN218) | 0.41 | 1.1 | 0.44 | −0.5 (−0.7) |
| H21 | 3.7 (27) | 11 | 1.3 | 1.0 | 1.3 | +0.2 (+0.3) |
| Q22 | −2 (5.8) | 1 | 0.62 | 1.1 | 0.69 | −0.2 |
| F25 | 44 (63) | 21 | 0.47 | 1.0 | 0.47 | −0.4 (−0.2) |
| D26 | 0 (0.1) | 0 | 0.79 | 0.89 | 0.7 | −0.2 (−0.3) |
| Q29 | 4.2 (4.4) | 0 | 0.38 | 0.97 | 0.37 | −0.6 |
| Y42 | 60 (88) | 30 | 1.2 | 1.2 | 1.4 | +0.2 |
| L45 | −1.6 (44) | 7 | 4.3 | 1.8 | 7.9 | +1.2 (+1.4) |
| Q46 | 53 (88) | 16 (hE120) | 0.9 | 1.4 | 1.2 | +0.1 (0) |
| P48 | 3.8 (5.1) | 4 | 1.2 | 1.7 | 2.0 | +0.4 |
| S51 | 0 (0) | 0 | 1.2 | 1.4 | 1.8 | +0.3 |
| E56 | 0.5 (0.9) | 0 | 2.1 | 0.97 | 2.0 | +0.4 (+0.8) |
| P61 | 0 (5.1) | 0 | 7.2 | 1.1 | 7.7 | +1.2 |
| S62 | 1.8 (14) | 1 (hS102) | 1.6 | 0.8 | 1.3 | +0.1 |
| N63 | 7.1 (17) | 2 | 1.2 | 1.4 | 1.7 | +0.3 (+0.7) |
| R64 | 57 (101) | 24 (sD164, sE44) | 7.9 | 2.1 | 16 | +1.6 (+1.8) |
| E65 | 3.3 (3.3) | 0 | 0.69 | 0.66 | 0.45 | −0.5 (−0.3) |
| Q68 | 6.4 (26) | 2 | 3.3 | 0.8 | 2.7 | +0.6 (+1.0) |
| Y164 | −5.7 (24) | 4 | 2.1 | 0.9 | 1.8 | +0.3 (+0.8) |
| R167 | 5.9 (32) | 8 (sE127) | 0.49 | 3.3 | 1.6 | +0.3 (−0.2) |
| K168 | 15 (60) | 12 (hW104mc) | 0.64 | 1.2 | 0.77 | −0.2 (+0.1) |
| D171 | 19 (50) | 16 (sR43) | 4.6 | 0.83 | 3.8 | +0.8 (+1.2) |
| K172 | −6.5 (27) | 15 | 20 | 1.5 | 30 | +2.0 (+1.6) |
| E174 | 17 (25) | 4 (hN218) | 0.33 | 0.61 | 0.21 | −0.9 (−0.9) |
| T175 | −2.1 (47) | 9 | 25 | 1.0 | 25 | +2.0 |

TABLE 2-continued

Relative on-rates, off-rates and affinities for alanine substitutions at residues in hGH that are buried to varying degrees at the Site 1 interface. Rate measurements were made using the hGHbp (S201C) matrix at 25° C. as described in Table 1.

| Site 1 contact residue | Changes in accessible area upon binding[1] (Å$^2$) | Vdw contacts[2] (H-bonds, h; salt bridges, s) | Changes in kinetics from wt[3] | | | ΔΔG (kcal/mol) BIAcore ™ (RIA)[4] |
|---|---|---|---|---|---|---|
| | | | off-rate | 1/on-rate | off/on | |
| F176 | −14 (5.8) | (hR43) 4 | 22 | 1.1 | 2 | +1.9 (+1.6) |
| R178 | 41 (70) | 8 (hI165mc, hM170mc) | 24 | 2.5 | 60 | +2.4 (+2.4) |
| I179 | −10 (26) | 9 | 2.9 | 1.3 | 3.9 | +0.8 (+0.6) |
| R183 | 1.2 (1.5) | 0 | 1.4 | 1.8 | 2.5 | +0.5 (+0.4) |
| E186 | 3.4 (5.6) | 0 | 0.97 | 1.0 | 0.98 | 0 (−0.1) |

[1]Accessible surface area to a 1.4 Å probe was calculated (Lee and Richards, supra) for each side-chain in the wild-type hormone and for wild-type missing atoms beyond the β-carbon (to mimic the alanine mutant) and for their corresponding complexes with the hGHbp using X-ray coordinates. De Vos et al., supra. The change in area buried attributed to the alanine mutation is the difference in accessible area of (free-bound)$_{wt}$-(free-bound)$_{Ala}$. The area only used was that buried beyond the β-carbon because this is the portion of the side-chain removed upon alanine substitution. Shown in parentheses is the area of each side-chain for atoms beyond the β-carbon in hGH that become inaccessible to solvent once the receptor binds.

[2]Total number of van der Waals contacts is the number of receptor atoms within 4.4 Å of any atom beyond the β-carbon of the contact side-chain based on inspection of the hGH (hGHbp)$_2$ complex. Over 80% of the contact distances are 3.8 to 4.2 Å. Groups making hydrogen bonds (h) or salt-bridges (s) are determined by donor-acceptor or complementary charge pairs within 3.3 Å of each other between hGH and the hGHbp. For example, hN218 next to H18 indicates a H-bond between H18 on hGH and N218 of the hGHbp. mc indicates an H-bond to a main-chain amide.

[3]The relative change in off-rate was calculated from $\frac{k_{off}wt}{k_{off}Ala\ mut}$ and for 1/on-rate by $\frac{k_{on}Ala\ mut}{k_{on}wt}$.

The change in $K_d$ from wild-type was calculated as:

$$\frac{K_d\ (Ala\ mut)}{K_d\ (wt)} = \frac{K_{off}/k_{on}\ (mut)}{k_{off}/k_{on}\ (wt)}.$$

[4]The ΔΔG values were calculated as $+RT\ln \frac{K_d\ (Ala\ mut)}{K_d\ (wt)}$ from BIAcore ™ biosensor data or in parentheses from radioimmunoassay data that was previously reported. Cunningham and Wells, supra; Cunningham and Wells, Proc. Nat. Acad. Sci. USA, 88: 3407–3411 (1991).

Figure 3:
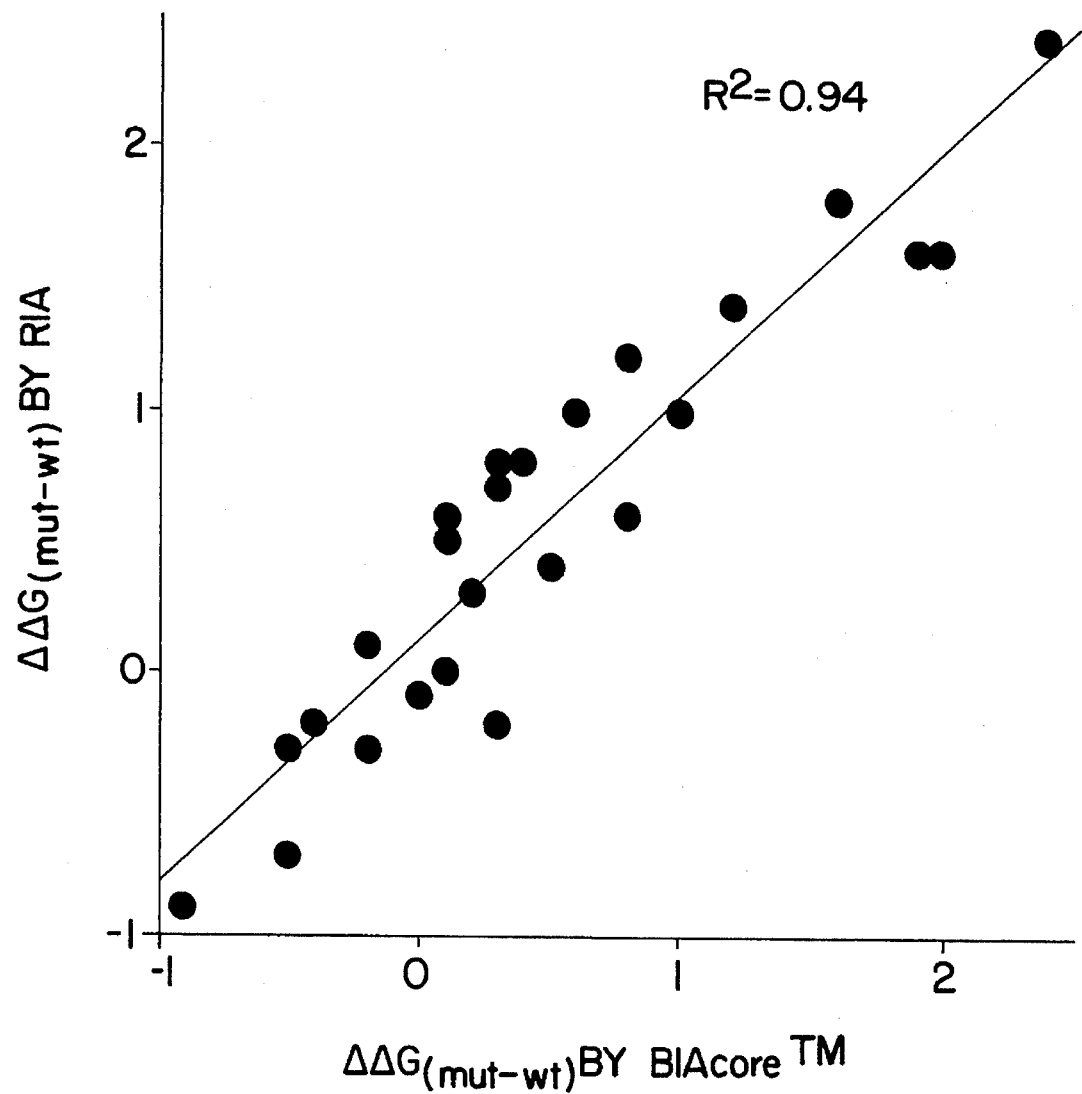
FIG. 3 shows the correlation between the change in the free energy of binding ($\Delta\Delta G_{(mut-wt)}$) calculated for alanine mutants of hGH relative to wild-type hGH when forming a 1:1 complex with the hGHbp from data obtained by RIA (y-axis) or BIAcore™ biosensor (x-axis). Values were taken from Table 2.

The (S201C)hGHbp-matrix was used to measure the affinities for alanine mutants at the 30 buried residues in the Site 1 interface (Table 2). Previously used was a radioimmunoprecipitation assay (RIA) to measure the binding constants for many of these mutants. Cunningham and Wells, 1989 and 1991, supra. A plot of the change in free energy relative to wild-type for the alanine mutants calculated by RIA data versus BIAcore™ biosensor data shows a tight correlation ($R^2=0.94$) with a slope near unity and an intercept close to zero. FIG. 3. Thus, the affinity data acquired on the biosensor matrix closely matches those measured in solution by the RIA. This indicates the matrix is not causing systematic binding artifacts. The average standard error in affinity constant is about 20% for using the BIAcore™ biosensor versus about 30% for the RIA. It is also possible that some dimerization of the hGHbp can occur in the RIA that would lead to systematic errors in affinities; this is prevented using the (S201C)hGHbp-matrix.

Of the 30 buried side-chains, only 7 (L45, P61, R64, K172, T175, F176, and R178) can account for about 85% of the total change in binding free energy resulting from the alanine substitutions. Another six (P48, E56, Q68, D171, I179, and R183) can essentially account for the remainder (Table 2). Eight other buried side-chains (M14, H21, Q46, S62, N63, Y164, R167, and E186) have essentially no effect on overall affinity (each causing less than 2-fold reduction in affinity). Three other buried side-chains (Q22, D26, and K168) have a small but significant effect on binding affinity. Five side-chains (H18, F25, Q29, E65, and E174) actually hinder binding because when they are converted to alanine, there are enhancements in affinity of 2 to 5-fold. The sum of the reductions in free energies caused by the alanine substitutions (−14.2 kcal/ml) is comparable to the total free energy of binding between hGH and the hGHbp (−12.3 kcal/mol) measured by the BIAcore™ sensor.

Thus, an hGH mutant with changes at H18, Q22, F25, D26, Q29, E65, K168, and E174 will have increased binding affinity for hGHbp. The variant with all alanins residues at these positions is calculated to have a binding affinity about 200-fold greater than that of wild-type hGH based on the additivity of individual amino acid changes. In conjunction with the data in Example II herein, it is expected that an Asp at position 18 and/or a Ser at position 174 in this combination mutant would also have a significantly greater binding affinity toward hGHbp than wild-type hGH.

Figure 4A:
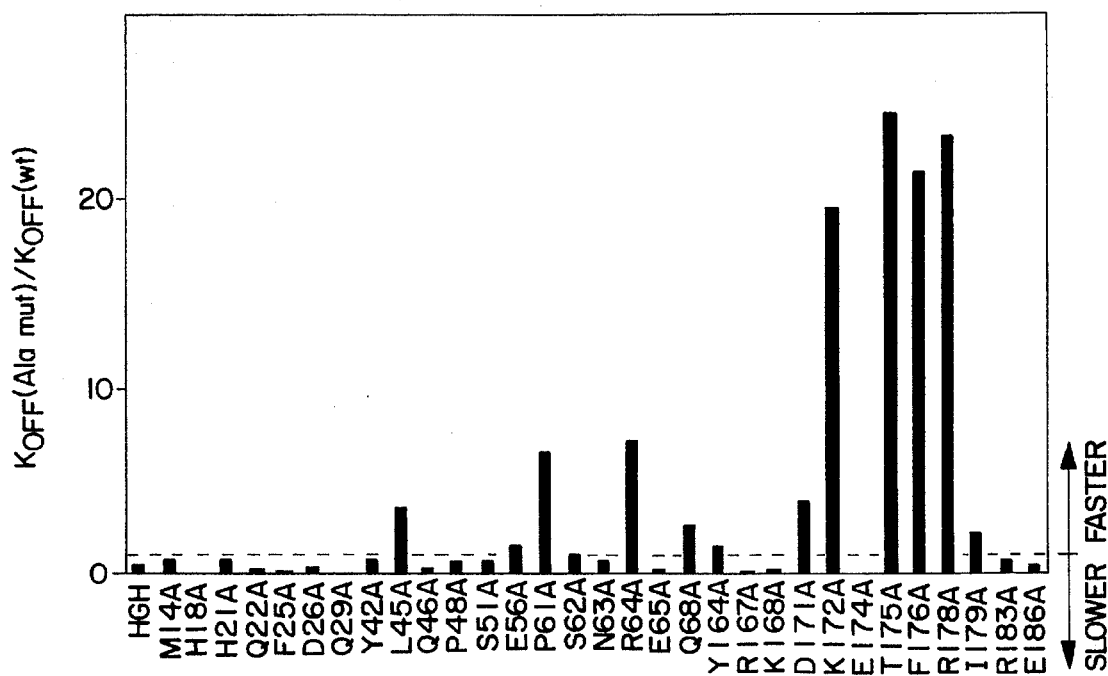
FIGS. 4A and 4B show the relative change in off-rate (FIG. 4A) or on-rate (FIG. 4B) for alanine mutants at contact residues. Data are taken from Table 2.
Figure 4B:
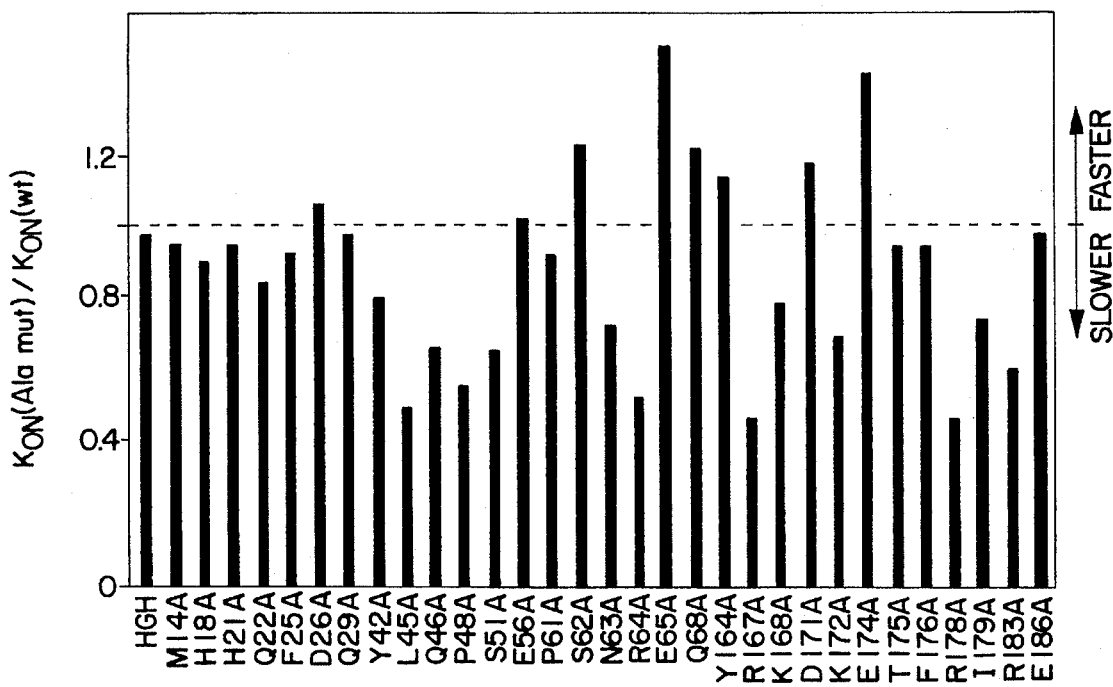

The off-rate effects are much larger than the on-rate effects (Table 2; FIG. 4). Thus, the same seven residues that most affect affinity account for most of the increase in off-rate (up to 25-fold). The conversion of three Arg side-chains (R64, R167, and R178) to Ala produced the greatest reductions in on-rate, but only about 2-fold. The conversion of two Glu side-chains (E65 and E174) to Ala caused the greatest increases in on-rate (nearly 2-fold improved). This suggests that electrostatic interactions are the most important side-chain determinants in guiding the hormone to the receptor.

The side-chains that most affect on-rate are not all the same as those that most affect off-rate. FIG. 4. For example, R167A causes the largest decrease in on-rate but leads to a compensating decrease in off-rate. Many of the alanine mutations at side-chains that dominate the affinity (P61A, K172A, T175A, and F176A) have virtually no effect on the association rate. The preferred combination mutant from these experiments, which has a 200-fold greater binding affinity for the GH receptor than wild-type hGH, resulting from the additivity of each mutation, has the sequence H18A,Q22A,F25A,D26A,Q29A,E65A,K168A,E174A.

Conclusion

The data indicate that only a small set of the buried side-chains at the interface are functionally crucial in binding. Without being limited to any one theory, it is believed that this is not an artifact of the method of analysis. First, the structure of the hGH.hGHbp complex has been solved and the residues buried in Site 1 are virtually identical to those seen in Site 1 for hGH in the hGH(hGHbp)$_2$ complex. De Vos et al., supra. Thus, the fact that the structural epitope is much smaller than the functional epitope is not because of contact differences in binding in the 1:1 versus the 1:2 complex (which is the coordinate set used to define the contact epitope).

Second, analysis of the functional importance of any side-chain by mutational study has the caveat that the mutant protein may exaggerate the effect by imposing a structural disturbance or an unusual steric, electrostatic, or hydrophobic interaction. Systematic replacements of side-chains with alanine are least disruptive to the structure. Wells, *Methods in Enzymol.*, 202: 390–411 (1991). The alanine mutation is the simplest to interpret because it removes atoms without introducing new ones that may create additional unfavorable or favorable interactions. The sum of all the disruptive effects caused by the alanine substitutions (−14.3 kcal/mol) does not dramatically exaggerate the total binding free energy (−12.3 kcal/mol). This suggests that the effects are localized to the individual binding determinants and do not grossly change the whole protein structure or the mode of binding. Given the large number of contact residues, it is also unlikely that single alanine substitutions would change the mode of binding in the complex, which is evidenced by the number of double alanine substitutions that have additive effects on binding, indicating that the sites act independently.

Also identified are some alanine mutations that affect affinity that are buried in the hormone and do not become further buried when the receptor binds. Cunningham and Wells, 1989, supra. For example, P5A, L6A, F10A, and V185A each disrupt affinity by 2- to 4-fold. Each of these side-chains makes contacts between helix 1 and helix 4 that dominate the Site 1 epitope but are not directly involved in binding. Similarly, F54 and I58 disrupt affinity and are buried in the loop region that positions the second mini-helix. This mini-helix contains R64 and other important binding determinants. Thus, some minor effects on binding can result from structural perturbations that are propagated from alanine mutations near but not at the structural epitope. However, the vast majority of residues tested away from the Site 1 structural epitope have no detectable effect on binding when converted to alanine. Cunningham and Wells, 1989, supra.

The alanine-scanning data show only seven of 30 side-chains buried at the interface account for about 85% of the binding energy. Virtually all of the rest can be accounted for by six other side-chains. It has been attempted to correlate a number of structural parameters that may explain why some residues are critical for binding and others are not. The residues are found important for binding cluster in a small region near the center of the structural epitope (mostly toward the end of helix 4). The functionally "null" contact residues tend to be near the periphery, in the center of helix 1 and the beginning of helix 4. This is a region that is critical for binding of hGH to the hPRL receptor (Cunningham and Wells, 1991, supra) and for forming a $(Zn^{+2}.hGH)_2$ storage complex. Cunningham et al., *Science*, 253: 545–548 (1990). Thus, while this area has little apparent role in binding to the hGH receptor, it does have other important functions.

Figures 5A, 5B:
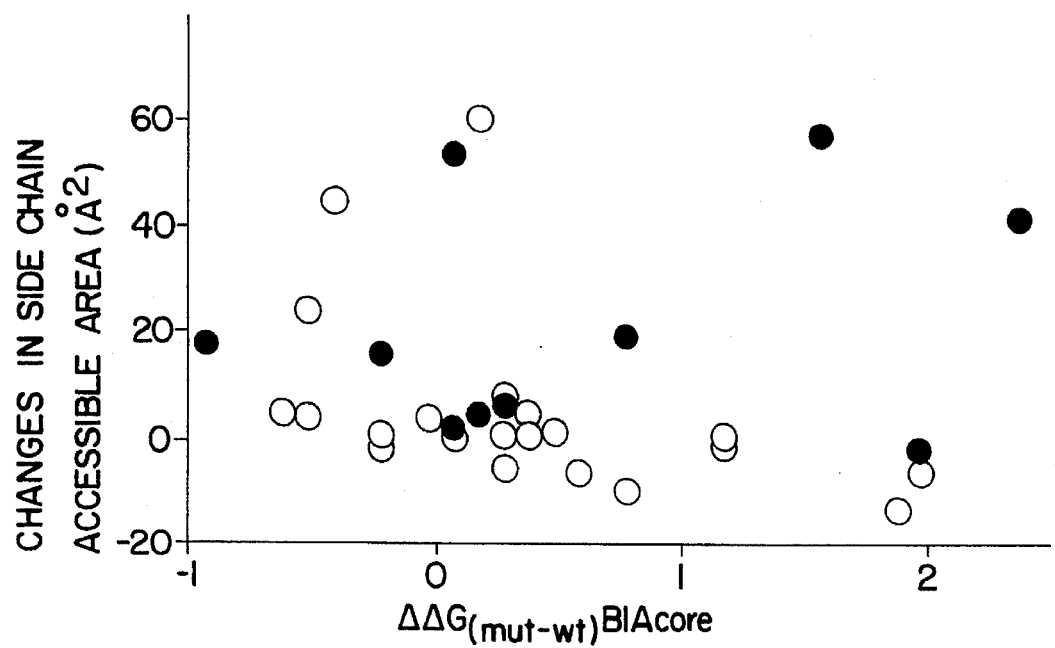
FIGS. 5A and 5B show the relationship between the change in binding affinity upon alanine substitution and the change in buried surface area (Å²) (FIG. 5A) or number of van der Waals contacts (FIG. 5B) for atoms in contact side-chains beyond the β-carbon. Closed circles are for residues buried at the interface that make hydrogen bonds or salt bridges with the receptor at Site 1, and open circles are for residues that do not. Data are plotted from Table 2.

Other systematic structural correlations are more difficult to make. Chothia and Janin, *Nature*, 256: 705–708 (1975) found that a change in buried surface area generally correlated with the free-energy of association between two proteins. The change in buried surface area that would occur upon complex formation for each of the alanine mutants was calculated from the difference in accessibility in the free and bound states between hGH and the alanine mutant. Table 2. However, a plot of the change in buried surface area upon binding versus the change in the free energy of binding when the side-chain is converted to alanine gives a very poor correlation. FIG. 5A. In some cases negative values for change in accessibility were obtained. This is because the missing side-chain in the alanine mutant creates a cavity at the interface, and hence more surface area would be covered upon complex formation. Also calculated was the change in side-chain accessibility that occurs upon binding for atoms beyond the beta-carbon that was the criterion for defining buried side-chains (see value in parentheses in column 2 of Table 2). Yet a plot of these values versus the change in free energy gives no better correlation. A plot of the number of van der Waals contacts made by atoms of hGH beyond the beta-carbon versus the change in affinity when the side-chain is converted to alanine (FIG. 5B) does not show a good correlation either. Neither correlation improves by considering separately the side-chains that are capable of electrostatic interactions.

Horton and Lewis, *Protein Science*, 1: 169–181 (1992) were able to predict affinities for 15 different protein-protein pairs using a semi-empirical method based on buried surface area and functional scaling of atomic solvation parameters (Eisenberg and McLachlan, *Nature*, 319: 199–203 [1986]) for the contact side-chains. Therefore, these scaled atomic solvation parameters were evaluated to see how well they can predict the free-energy changes resulting from the individual alanine substitutions. There was little correlation. Thus, while buried surface area, number of van der Waals contacts, and scaled atomic solvation calculations are useful correlates for general binding affinity, they are poor predictors of the role of individual side-chains in this epitope.

On average, the energetics for electrostatic interactions are considerably weaker than estimates made from mutagenesis of enzyme-substrate complexes. From mutational analysis of tyrosyl-tRNA synthetase, it was estimated that the free energy loss for disrupting a charged H-bond pair is 3.5–5 kcal/mol and for a neutral H-bond pair is 0.5–1.5 kcal/mol. Fersht et al., *Nature*, 314: 235–238 (1985). Seven side-chains from hGH form hydrogen bonds with the hGHbp (H18, Q46, S62, K168, E174, T175, and R178). Five of these are charged H-bonds (Q46, K168, E174, T175, R178), yet the change in binding free energy when they are converted to alanine is only +0.1, –0.2, –0.9, +2.0, and +2.0 kcal/mol, respectively, giving an average value of +0.6 kcal/mol. The change in affinity for mutating the two neutral H-bonding side-chains (H18 and S62) is only –0.5 and +0.1, respectively. Three other side-chains form salt-bridges with the hGHbp (R64, R167, and D171), yet these cause reductions of only +1.6, +0.3, and +0.8 kcal/mol, respectively. These values are less than ones estimated for two engineered salt bridges in subtilisin that range from +1.8 to +2.3 kcal/mol. Wells et al., *Proc. Natl. Acad, Sci. USA,* 84: 1219–1223 (1987). Thus, the strength of the contacts varies widely in the hGH-hGHbp interface and the interactions are considerably weaker when compared with those of small molecule binding sites.

From mutational studies of protein interiors it has been estimated that each buried methylene group contributes –1.0 to –1.5 kcal/mol to the overall free-energy of folding (for recent review see Shortle, *Quart. Rev. Biophys.,* 25: 205–250 (1992), and references therein). Converting a number of hydrophobic side-chains in hGH to alanine caused effects that were very much weaker than would be expected from these studies. For example, the largest effects seen for mutations at hydrophobic side-chains are for L45A, K172A (only the aliphatic portion makes contact with the receptor), F176A, and I179A, which cause reductions in affinity of +1.2, +2.0, +1.9, and +0.8 kcal/mol, respectively. Moreover, several other hydrophobic groups that are more highly or comparably buried upon complex formation (F25, Y42, Y164) have almost no effect when mutated to alanine.

In summary, a striking feature of the 1:2 hGH:receptor complex has been found, i.e., that only a small set of the side-chains from hGH that are buried in Site 1 affect binding affinity when converted to alanine. Thus, the functional epitope defined by alanine-scanning mutagenesis is considerably smaller than the structural epitope defined by buried residues or van der Waals contacts. Some residues that are near but not within the Site 1 epitope can modestly affect binding affinity when converted to alanine, presumably by indirect effects. Finally, most of the functionally important side-chains modulate off-rate, not on-rate, of the hormone to the receptor.

EXAMPLE II

Purpose

It was desired to determine to what degree affinity of the Site 1 of hGH could be enhanced. It was also desired to determine which side-chains of hGH should be mutated to enhance binding affinity—ones that modulate affinity as identified by alanine-scanning mutagenesis, ones identified by crystallography to make contact, or both. Finally, if mutations can substantially enhance affinity, it was desired to learn whether they do so by affecting the on-rate or the off-rate of the mutated hormone.

Summary

Very high affinity variants of hGH were produced by combining affinity-enhanced mutants of hGH that were sorted from five separate libraries in which a total of about $10^6$ protein variants were displayed monovalently on phagemid particles. Altogether 20 different residues in the Site 1 binding site were mutated. Although only small increases in affinity were contributed from each mutant side-chain, these produced additive increases in the free-energy of binding. By this approach, an hGH variant was produced having 15 substitutions that bound receptor about 400-fold tighter than wild-type hGH.

Materials and Methods a) General Procedures

Restriction enzymes, polynucleotide kinase, $T_7$ DNA polymerase, and $T_4$ DNA ligase were obtained from Gibco-BRL or New England Biolabs and used according to the manufacturer's directions. Randomized oligonucleotide cassettes were phosphorylated, annealed, and ligated into constructs as described in Lowman et al., supra, and Lowman and Wells, supra. Sequenase® brand enzyme was purchased from United States Biochemical and used according to the manufacturer's directions for single-stranded sequencing. Sanger et al., supra.

Some site-specific mutants of hGH were constructed by oligonucleotide-directed mutagenesis, using single-stranded template. Kunkel et al., *Methods Enzymol.,* 204: 125–139 (1991). The plasmid phGHam-g3, encoding wild-type hGH fused to the carboxy-terminal domain of M13 geneIII (Lowman et al., supra), was used to construct parental vectors for cassette mutagenesis. Monovalent hGH-displaying phagemid particles were prepared (Lowman and Wells, supra) by electro-transforming *E. coli* XL1-Blue cells (Stratagene), and adding M13K07 helper phage. Vieira and Messing, supra.

DNA molecules encoding the soluble hormones were expressed in *E. coli* (Chang et al., supra), ammonium-sulfate precipitated from osmotically shocked cell supernatants (Olson et al., *Nature,* 293: 408 [1981]), and quantitated by laser densitometry of Coomassie-stained SDS-PAGE gels. Cunningham et al., supra. Some variants were further purified by ion-exchange chromatography on a Mono-Q column (Pharmacia-LKB Biotechnology, Inc.).

(b) Preparation of hGH-phagemid libraries

For mutagenesis of Minihelix-1 (residues 41–46) of hGH, the existing AatII site in phGHam-g3 was destroyed using oligonucleotide #718 (5'-GCC ACC TGA TGT CTA AGA AAC-3') (SEQ. ID NO. 1). Unique SfiI and AatII sites were introduced into phGHam-g3 to create pH0779, using oligonucleotides #782 (5'-TTT GAA GAG GCC TAT ATG GC C AAG GAA CAG AAG-3') (SEQ. ID NO. 2) and #821 (5'-CAG AAC CCC CAT TGA CGT CCC TCT GTT TC-3') (SEQ. ID NO. 3), respectively. The latter oligonucleotide also introduced a +2 frameshift and a TGA stop codon after residue 49. A randomized cassette was constructed from the complementary oligonucleotides #822 (5'-TC CCG AAG GAG CAG NNS NNS TCG TTC NNS NNS AAC CCG CAG ACG T-3') (SEQ. ID NO. 4) and #823 (5'-CTG CGG GTT SNN SNN GAA CGA SNN SNN CTG CTC CTT CGG GAT AT-3') (SEQ. ID NO. 5). The parental DNA (pH0779) was digested with restriction enzymes SfiI and AatII, and the large fragment was purified and ligated with the cassette. The ligation products were electro-transformed into XL1-Blue cells for phagemid preparation in two aliquots, yielding 1×10⁶ independent transformants each, as described by Lowman and Wells, supra.

To construct the Loop-A (residues 54–64) library of hGH, the existing AatII site in phGHam-g3 was destroyed using oligonucleotide #718. Unique AatII and BstEII restriction sites were introduced in the hGH gene to construct pH0709, using oligonucleotides #719 (5'-AAC CCC CAG AC$\underline{G}$ TCC CTC TGT-3') (SEQ. ID NO. 6) and #720 (5'-GAA ACA CAA CAG $\underline{TAA}$ $\underline{AGG}$ $\underline{TAA}$ CCT AGA GCT GCT-3') (SEQ. ID NO. 7). The latter oligonucleotide also introduced a +1 frameshift and a TAA stop codon after residue 69. In addition, the unique EcoRI site was destroyed using oligonucleotide #536 (5'-CGT CTT CAA GA$\underline{G}$ TTC AAC TTC TCC-3') (SEQ. ID NO. 8), to permit restriction-selection against possible contaminating clones from previous libraries (Lowman and Wells, supra). A randomized cassette was constructed from the complementary oligonucleotides #803 (5'-pCC CTC TGT NNS TCA NNS TCT NNS CCG ACA CCC AGT AAT NNS GAG GAA ACA CAA CAG AAG A-3') (SEQ. ID NO. 9) and # 804 (5'-pGTT ACT CTT CTG TTG TGT TTC CTC SNN ATT ACT GGG TGT CGG SNN AGA SNN TGA SNN ACA GAG GGA CGT-3') (SEQ. ID NO. 10). The parental DNA (pH0709) was digested with restriction enzymes AatII and BstEII, and the large fragment was purified and ligated with the cassette. The ligation products were electro-transformed into XL1-Blue cells for phagemid preparation in two aliquots, yielding 1.6×10⁶ and 1.0×10⁶ independent transformants.

(c) Combinatorial hGH libraries from hGH-phagemid library pools

DNA from the Helix-1 and the Helix-4b pools (selected for 0, 2, or 4 rounds; Lowman et al., supra) was purified and digested with the restriction enzymes AccI and BstXI. The large fragment from each Helix-1 pool (randomly mutated at F10, M14, H18, and H21) was then purified and ligated with the small fragment from each Helix-4b pool (randomly mutated at R167, D171, T175, I179, in the E174S,F176Y background) to yield the three combinatorial libraries 707A (un-selected Helix-1 and Helix-4b pools), 707B (twice-selected Helix-1 pool with twice-selected Helix-4b pool), and 707C (4-times selected Helix-1 pool with 4-times selected Helix-4b pool). Duplicate ligations were also set up with one-tenth to one-half as much vector DNA and designated as 707D, 707E, and 707F, corresponding to the 0-, 2-, and 4-round starting libraries, respectively. All of these variant pools also contained the mutations E174S,F176Y obtained in earlier hGH-phagemid-binding selections. Lowman et al., supra. The ligation products pH0707A-F were processed and electro-transformed into XL1-Blue cells. The number of independent transformants obtained from each pool, based on colony-forming units (CFU), was as follows: 2.4×10⁶ from pH0707A, 1.8×10⁶ from pH0707B, 1.6×10⁶ from pH0707C, 8×10⁵ from pH0707D, 3×10⁵ from pH0707E, and 4×10⁵ from pH0707F. hGH-phagemid particles were prepared and selected for hGHbp-binding over 2 to 7 cycles as described by Lowman et al., supra.

Several variants of hGH were constructed by combining isolated variants from the Helix-1 and Helix-4b libraries. The parental variants were the three tightest-binding from each library: A=H10,G14,N18,N21; B=A10,W14,D18,N21; C=F10,S14,F18,L21; D=N167,S171,S174,Y176,T179; E=E167,S171,S174,Y176,I179; F=N167,N171,S174,Y176,T179. hGH-phagemid DNA was purified and digested with the restriction enzymes EcoRI and BstXI. The large fragment from each Helix-4b variant was then purified and ligated with the small fragment from each Helix-1 variant to yield combined variants with mutations in both Helix-1 and Helix-4b. These variants were designated as AD, AE, AF, BD, BE, BF, CD, CE, CF to indicate the respective pairwise combinations of Helix-1 (A, B, or C) and Helix-4b (D, E, or F) mutations.

A series of five oligonucleotides were used to revert several of the phage-derived mutations in the variant BD to the corresponding wild-type residue: #797 (5'-CTG CGT GCT $\underline{C}$AC CGT CTT $\underline{C}$AC CAG $\underline{T}$TG GCC TTT G-3') (SEQ. ID NO. 11) for D18H,N21H; #798 (5'-GTC AGC ACA T$\underline{T}$C CTG CGC ACC-3') (SEQ. ID NO. 12) for Y176F; #799 (5'-CTC TCG $\underline{C}$GG CTC $\underline{T}$TC GAC AAC GCG $\underline{A}$TG CTG CGT GCT-3') (SEQ. ID NO. 13) for A10F,W14M; #800 (5'-TAC TGC TTC A$\underline{GG}$ AAG GAC ATG $\underline{GA}$C AAG GTC AGC-3') (SEQ. ID NO. 14) for N167R,S171D; #801 (5'-CTG CGC A$\underline{T}$C GTG CAG TGC-3') (SEQ. ID NO. 15) for T179I; #875 (5'-CTC TCG AGG CTC $\underline{TT}$C GAC AAC GCG TGG-3') (SEQ. ID NO. 16) for A10F.

The hGH variant 852d was constructed using BD as template and the following oligonucleotides: #843 (5'-CAG ACC TCC CTC TGT $\underline{CCC}$ TCA GAG TCT ATT CCG-3') (SEQ. ID NO. 17) for adding F54P; #844 (5'-ACA CCC TCC AAC A$\underline{A}$G GAG GAA ACA CAA CAG-3') (SEQ. ID NO. 18) for R64K; #846 (5'-CCA AAG GAA CAG A$\underline{TT}$ $\underline{C}$AT TCA TTC $\underline{TGG}$ $\underline{TGG}$ AAC CCC CAG ACC TCC-3') (SEQ. ID NO. 19) for K41I,Y42H,L45W,Q46W. Variant 852b was constructed using the same oligonucleotides with template phGHam-g3.

(d) Radio-immunoprecipitation assays

The equilibrium binding affinity for hGHbp was determined by assaying hGH variants in competition with ¹²⁵I-labeled hGH, labeled variant BD, or labeled variant 852d, in binding buffer: 50 mM Tris, pH 7.5, 10 mM MgCl₂, 0.1% bovine serum albumin, 0.02% sodium azide. Lowman et al., *J. Biol. Chem.*, 266: 10982–10988 (1991). Immunoprecipitation of the hGH-hGHbp complex was carried out using a monoclonal antibody designated MAbS. Barnard et al., *Endocrinology*, 115: 1805–1813 (1984). Dissociation constants were obtained by Scatchard analysis. Cunningham and Wells, 1989, supra. Variants BD and 852d contain F176Y, which if iodinated could perturb the hormone-receptor interface. However, iodinated BD (cold) was indistinguishable from unlabeled BD in competing with ¹²⁵I-labeled BD for binding.

(e) Kinetics assays

Association and dissociation rate constants for hGH variants binding to immobilized hGHbp were obtained by measurement of surface plasmon resonance (SPR) using a Pharmacia BIAcore™ biosensor. In this system, hGHbp is covalently coupled to a dextran matrix attached to a biosensor chip. The hormone is maintained at constant concentration in a liquid phase passing over this surface at a constant flow rate. The instrument measures the mass of protein binding to the matrix in real time by sensing the change in SPR signal due to the change in refractive index near the biosensor surface. Löfås and Johnsson, *J. Chem. Soc. Chem. Commun.*, 21: 1526–1528 (1990).

A variant of hGHbp(S201C) was used as the immobilized species because binding of a second receptor on the matrix is blocked (see Example I). The hGHbp(S201C) was reduced and coupled to the biosensor chip via EDC/NHS activation of the dextran layer and 2-(2-pyridinyldithio)ethaneamine hydrochloride (PDEA) (activated thiol) chemistry to a level of 1000–2000 RU's, using 10 mM sodium acetate (pH 5.0); reagents and procedures were obtained from Pharmacia Biosensor. Binding and elution steps were carried out at a flow rate of 3–20 μL/min in PBS buffer (pH 7.4) containing 0.05% Tween-20.

The density of the hGHbp coupled to the matrix affects the absolute but not relative $k_{on}$ and $k_{off}$ values by up to two-fold for wild-type hGH. Thus, when different biosensor chips were used the kinetic parameters for the wild-type hGH were determined so that they could be normalized for comparing different mutants whose kinetic parameters may have been measured on different biosensor chips. The relative kinetic values so obtained were consistent over different flow-cells, and calculated affinity measurements correlated well with the results of the radioimmunoprecipitation assay. Dissociation rate constants were obtained by plotting $\ln(R_o/R_t)$ vs t; association rate constants were obtained by plotting [Slope of $(dR_t/dt)$ vs. $R_t$] against hormone concentration (Karlsson et al., supra), or by plotting $\ln(dR_t/dt)$ against hormone concentration using the BIAcore™ biosensor kinetics evaluation software (Pharmacia Biosensor). Equilibrium dissociation constants, $K_d$'s, were calculated as $k_{off}/k_{on}$. Standard deviations, a, for $\sigma_{on}$ for $k_{on}$ and $\sigma_{off}$ for $k_{off}$, were obtained from measurements with 2 or more series of 2-fold or 3-fold dilutions ($k_{on}$) or with 2 or more concentrated ($\geq 5$ μM) hormone samples ($k_{off}$). The resulting errors ($\epsilon[K]$) in calculated $K_d$'s were estimated according to the following formulas using the total derivative of $K=f(k_{on}, k_{off})$: (for a discussion, see Bevington, supra)

$$\epsilon[K]=[(\delta K/\delta k_{off})^2(d[k_{off}])^2+(\delta K/\delta k_{on})^2(d[k_{on}])^2]^{1/2} \quad (1)$$

$$\epsilon[K]=[(k_{on})^{-2}(\sigma_{off})^2+(k_{off})^2(k_{on})^{-4}(\sigma_{on})^2]^{1/2}. \quad (2)$$

Results (a) Residues in the hGH-receptor binding functional epitope

Figure 6A:
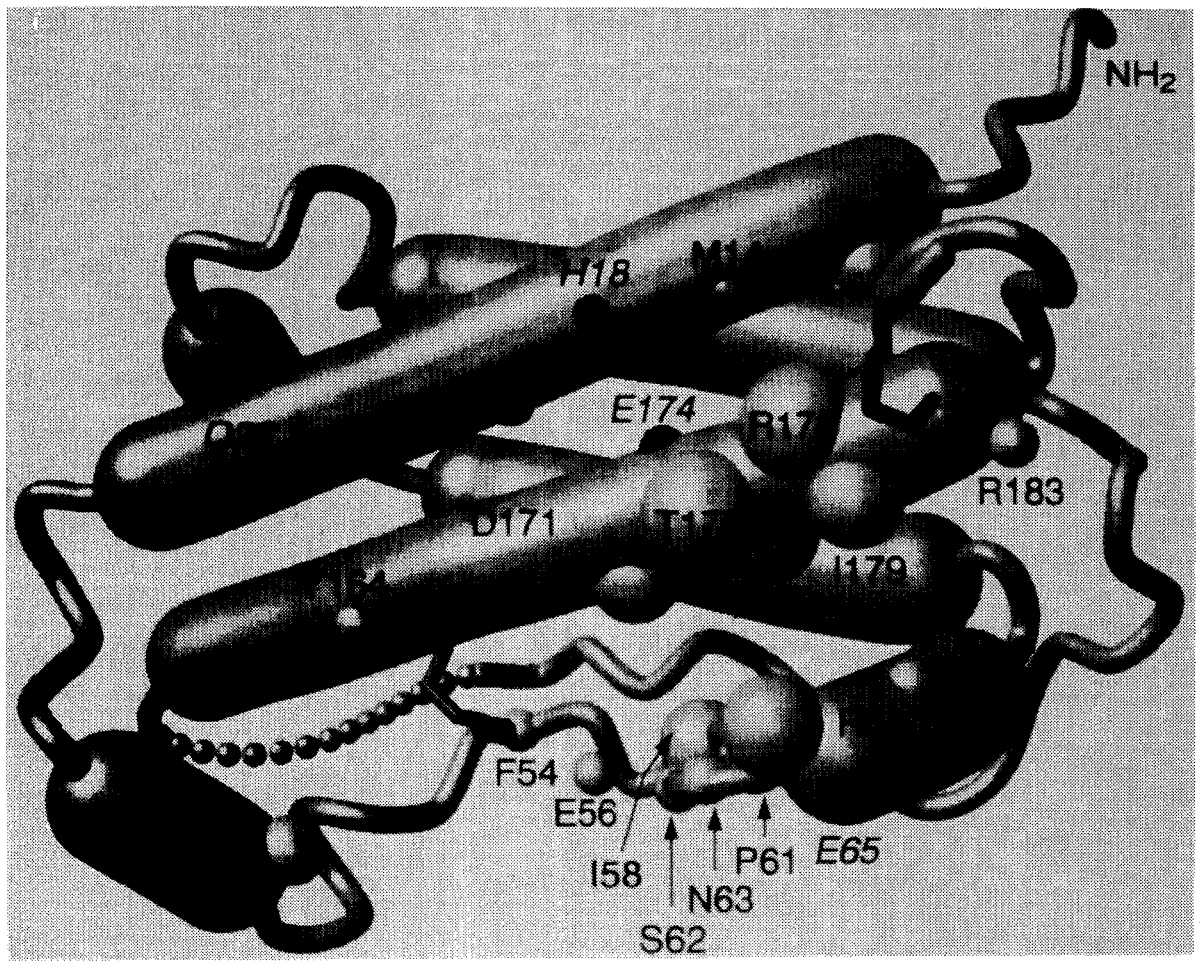
FIGS. 6A, 6B, and 6C show a comparison of receptor binding epitopes defined by alanine-scanning mutagenesis, x-ray crystal structure, or phage display, respectively.
Figure 6B:
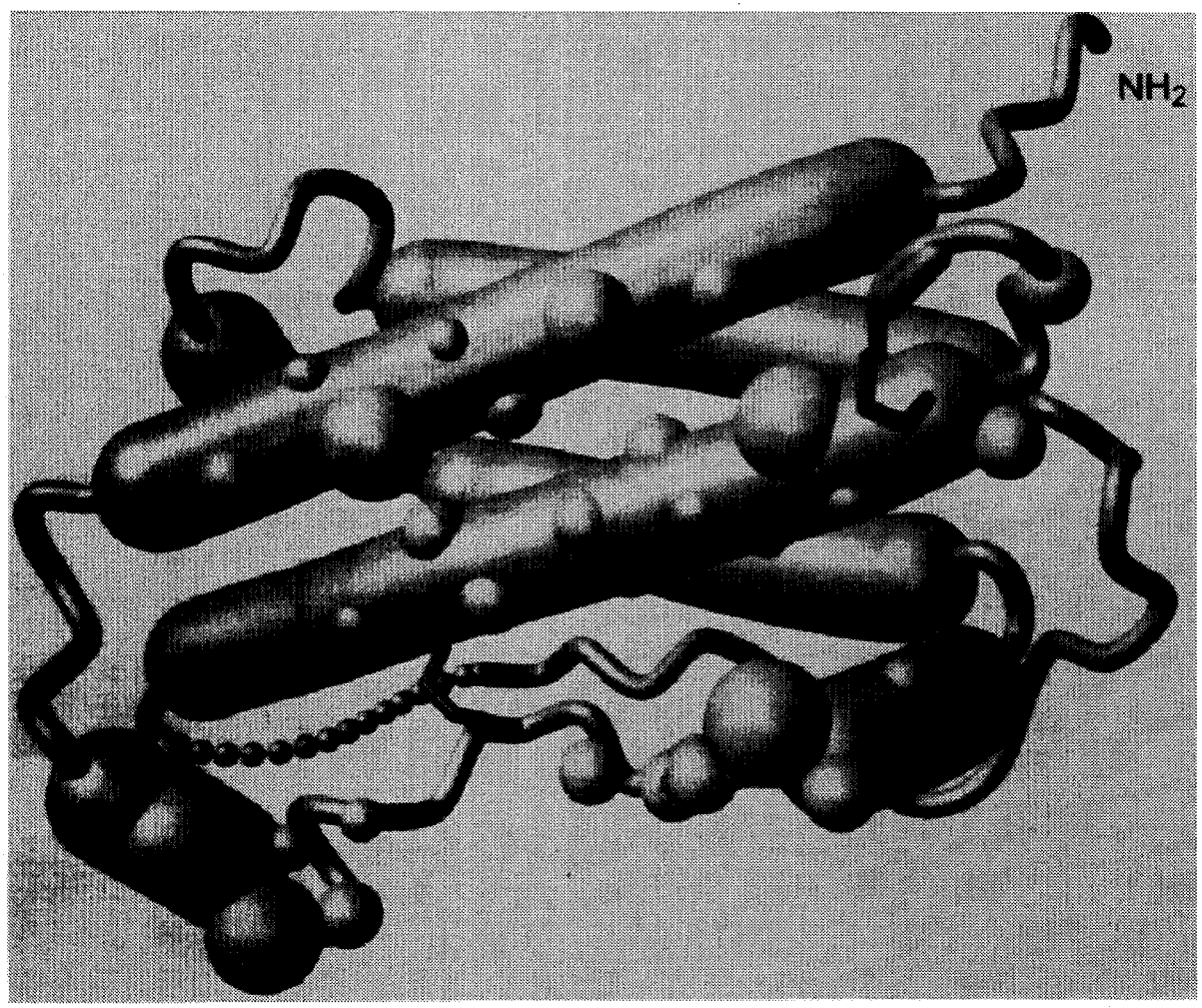

Structural analysis of the hGH(hGHbp)$_2$complex (de Vos et al., supra) identified over 30 side-chains in Site 1 of hGH that undergo some degree of burial when the first receptor binds (FIG. 6B). Although most of these were tested as alanine mutants prior to the structural elucidation (Cunningham and Wells, 1989, supra; 1991, supra), four residues (K41, Y42, L45 and Q46) in the first minihelix (Minihelix-1) were not evaluated. Therefore, these residues were converted singly to alanine and the effects on binding affinity were measured either by competitive displacement with [$^{125}$I]-hGH and immunoprecipitation (Cunningham and Wells, 1989, supra) or using the BIAcore™ biosensor from Pharmacia. Both methods gave comparable affinity measurements, as shown in Example I.

The side-chains of Y42 and Q46 became highly buried upon receptor binding, yet alanine replacements caused less than a two-fold reduction in affinity (Table 3). Leu 45 makes fewer contacts with the receptor than Y42 or Q46, yet the L45A mutant causes a 10-fold reduction in affinity. Lys41 makes a salt-bridge with Glu127 of the receptor. The DNA encoding the K41A mutant did not express well enough to obtain material for an affinity measurement; however, DNA encoding a more conservative variant, K41Q, did express sufficiently well. This variant had a 2.6-fold lower affinity than wild-type hGH. Thus, the Minihelix-1 region is clearly part of the functional epitope in hGH Site-1 (FIG. 6A). With these data and those of Example I, the effects have been measured for at least one replacement (mostly alanines) at residues whose side-chains become buried when the first receptor binds at Site 1.

TABLE 3

Receptor binding affinities of hGH alanine mutants in wild-type background, measured by BIAcore ™ (†) or by RIA (unmarked) and normalized relative to the RIA value for wild-type hGH as measured by Cunningham et al., 1989, supra. Alanine or glutamine mutations were made to test the contributions of side-chains in the Minihelix-1 region of wild-type hGH. For comparison with the structural epitope, the number of van der Waals contacts with receptor is also shown, derived from the crystal structure of the hGH (hGHbp)$_2$ complex.

| Variant | Number of van der Waals Contacts | $K_d$ (mut) / $K_d$ (pM) | $K_d$ (hGH) |
|---|---|---|---|
| hGH (wild-type) | — | 340 | 1 |
| K41A | — | NE | NE |
| †K41Q | 7 | 880 ± 84 | 2.6 |
| Y42A | 30 | 540 ± 80 | 1.6 |
| L45A | 7 | 3400 ± 330 | 10 |
| Q46A | 16 | 320 ± 20 | 0.9 |

(b) Design and analysis of random mutant libraries

Figure 7:
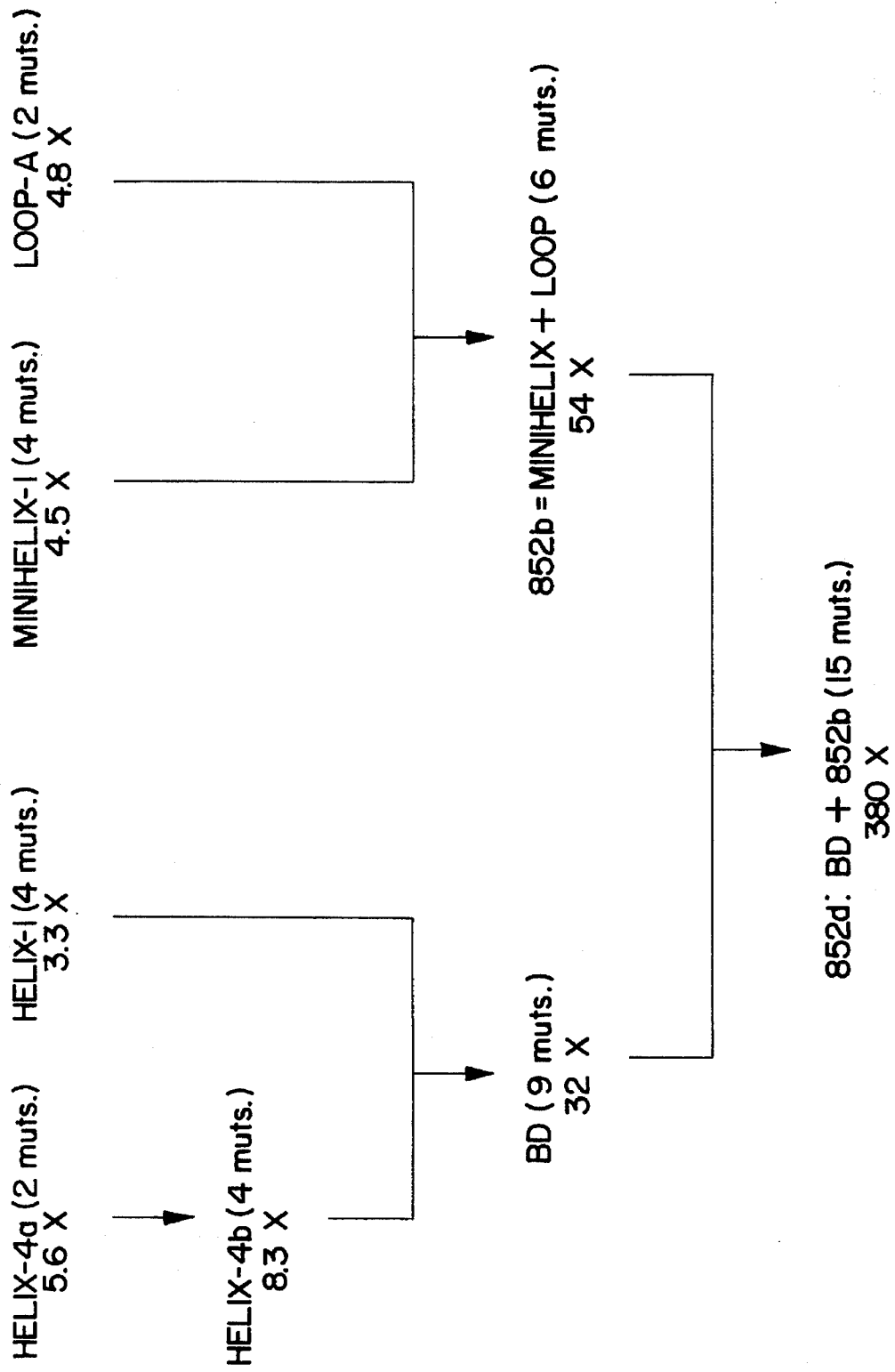
FIG. 7 shows the strategy for combining phage-derived mutations that enhance receptor binding affinity. The best selectants are shown with the fold increase in affinity over wild-type. The number of mutations from wild-type found in each of these variants is also shown (e.g., 4 muts.). Libraries randomized at four codons each in helix-1, helix-4, mini-helix-1, or the loop connecting helices 1 and 2, were sorted separately. Two mutations (E174S/F176Y) identified in Helix-4a were used as background for additional randomization and selection at other helix-4 sites (Helix-4b; Lowman et al., supra). The mutations identified in Helix-1 and Helix-4b were combined to yield the BD variant; mutations in Minihelix-1 and Loop-A were combined to yield variant 852b. Finally, mutations from these two variants were combined to yield variant 852d.

Five separate libraries were sorted in which four residues within the structural and/or functional Site 1 epitope were randomized (FIG. 7). Restricting each library to 4 random codons allowed sampling of most of the possible variants (~2×10$^5$ protein sequences generated from ~1×10$^6$ DNA sequences) within the limits of the library size (average of ~1×10$^7$ independent transformants).

Previously, a library (called Helix-4a) was produced in which residues K172, E174, F176 and R178 were randomized and displayed on monovalent phagemid particles. Lowman et al., *Biochemistry*, supra. After 3 cycles of binding selection, the tightest binding mutant (E174S,F176Y) had an affinity about 5-fold higher than wild-type hGH. These two mutants were fixed in a second library (called Helix-4b) in which R167, D171, T175, and I179 were randomly mutated in the E174S,F176Y background. After 6 rounds of selection a pentamutant (R167D,D171S,E174S,F176Y,I179T) was isolated that bound about 8-fold tighter than wild-type hGH. In a separate library (called Helix-1) residues F10, M14, H18 and H21 were randomly mutated. After 4 rounds of selection a tetramutant (F10A,M14W,H18D,H21N) was isolated that bound 3-fold tighter than wild-type hGH.

Here, the phage selection studies were expanded to the loop connecting helices 1 and 2. The four contact residues in Minihelix-1 (K41, Y42, L45 and Q46) were randomized and representative clones were sequenced after 2 to 7 rounds of binding selection (Table 4). Some residues were highly over-represented at given positions compared to what was expected from the frequency of those residues in the starting library. For example, about 35% of the clones contained a Q46W mutation. This was 7.6 standard deviation units above a random chance occurrence for Trp in the library. This is a good way to score the pool of selectants to establish a consensus sequence because it accounts for the expected codon bias and sampling statistics. By this criteria there was a mild preference for K41R, a slight preference for Y42R or Y42Q, a strong preference for L45W or L45 and a stronger preference for Q46W.

TABLE 4

Consensus residues identified after sorting hGH-phagemid libraries. The most frequently occurring residues from phage-displayed libraries are shown, based on fractional representation ($P_f$) among all sequenced clones after 2 to 7 rounds of binding selection. Expected frequencies ($P_e$) were calculated from the number of NNS codons for each amino acid theoretically in the starting library. Standard deviations ($\sigma_n$) were calculated as $\sigma_n = [P_e(1-P_e)/n]^{1/2}$. Only residues for which the fraction found exceeded the fraction expected by at least $2\sigma_n$ are shown (i.e., $[(P_f-P_e)/\sigma_n] \geq 2$). For the Minihelix-1 library, n = 17 sequences; Loop-A library, n = 26; Combinatorial library (Helix-1), n = 68; Combinatorial library (Helix-4b), n = 56.

| Residue | | $P_c$ | $\sigma_n$ | $P_f$ | $\frac{P_f - P_c}{\sigma_n}$ |
|---|---|---|---|---|---|
| Minihelix-1: | | | | | |
| K41 | R | .094 | .071 | .35 | 3.7 |
|  | F | .031 | .042 | .12 | 2.0 |
| Y42 | R | .094 | .071 | .24 | 2.0 |
|  | Q | .031 | .042 | .18 | 2.0 |
| L45 | W | .031 | .042 | .24 | 4.8 |
|  | L | .094 | .071 | .41 | 4.5 |
| Q46 | W | .031 | .042 | .35 | 7.6 |
|  | F | .031 | .042 | .12 | 2.0 |
|  | Y | .031 | .042 | .12 | 2.0 |
| Loop-A: | | | | | |
| F54 | P | .062 | .047 | .73 | 14.1 |
| E56 | D | .031 | .034 | .19 | 4.7 |
|  | W | .031 | .034 | .19 | 4.7 |
|  | Y | .031 | .034 | .12 | 2.5 |
| I58 | I | .031 | .034 | .31 | 8.1 |
|  | V | .062 | .047 | .23 | 3.5 |
| R64 | K | .031 | .034 | .81 | 22.8 |
| Combinatorial (Helix-1): | | | | | |
| F10 | A | .062 | .03 | .41 | 12.0 |
|  | F | .031 | .02 | .25 | 10.4 |
|  | H | .031 | .02 | .16 | 6.2 |
| M14 | W | .031 | .02 | .26 | 11.1 |
|  | S | .094 | .04 | .26 | 4.8 |
|  | Y | .031 | .02 | .09 | 2.7 |
|  | N | .031 | .02 | .09 | 2.7 |
|  | H | .031 | .02 | .07 | 2.0 |
| H18 | D | .031 | .02 | .43 | 18.8 |
|  | F | .031 | .02 | .12 | 4.1 |
|  | N | .031 | .02 | .10 | 3.4 |
| H21 | N | .031 | .02 | .46 | 20.2 |
|  | H | .031 | .02 | .13 | 4.8 |
| Combinatorial (Helix-4b): | | | | | |
| R167 | N | .031 | .02 | .63 | 25.6 |
|  | K | .031 | .02 | .13 | 4.1 |
| D171 | S | .094 | .04 | .64 | 14.1 |
|  | D | .031 | .02 | .14 | 4.8 |
|  | N | .031 | .02 | .13 | 4.1 |
| T175 | T | .062 | .03 | 1.0 | 29.1 |
| I179 | T | .062 | .03 | .66 | 18.6 |
|  | N | .031 | .02 | .13 | 4.1 |

A second library (called Loop-A) was constructed in which F54, E56, I58 and R64 were randomly mutated. Alanine replacements caused a 4- to 20-fold reduction in affinity depending on the side-chain (FIG. 6A). Despite the fact that R64 is the only one of these residues that makes direct contact with the receptor (FIG. 6B), all positions showed a moderate to very strong preference for a particular residue that was usually different from the wild-type. R64K was the most preferred (found in 81% of the clones); it is known that R64K alone causes a ~3-fold improvement in binding affinity. Cunningham et al., Science, 247: 1461–1465 (1990). After this the order of preference went F54P>I58T>E56D or E56W.

The binding affinities for many of these mutants were analyzed by expressing the free hormone in a non-suppressor host that terminates translation at the amber codon at the end of hGH and the start of the geneIII domain. Lowman et al., Biochemistry, supra. Virtually every clone tested, between 3 to 7 rounds of binding selection from the Minihelix-1 library, had affinities greater than wild-type hGH (Table 5). The best was K41I,Y42H,L45W,Q46W, which was 4.5-fold improved in affinity over wild-type hGH. This DNA sequence is expected to occur randomly at a frequency of one in a million clones, which demonstrates the power of the affinity selection. Similar results were obtained from the Loop-A library with the best isolates being F54P,R64K and F54P,E56D,I58T,R64K, which are about 5-fold improved over wild-type hGH.

TABLE 5

Binding data for individual hGH clones mutated in (A) the Minihelix-1 or (B) Loop-A. Affinity constants were measured by competition binding to hGHbp versus $^{125}$I-labeled hGH. Wild-type hGH affinity is from Cunningham and Wells, 1989, supra. The fold increase in affinity over hGH for binding hGHbp is shown as the ratio $K_d$ (hGH)/$K_d$ (Mutant). Some clones were not analyzed (ND). Identical affinities were assumed for equivalent variants (†). Clones with spurious mutations (E65V ‡; S57Y §; N47Y ¶; P48S @) are indicated.

A. Minihelix-1 library

| | Residue Position | | | | | |
|---|---|---|---|---|---|---|
| Clone | 41 | 42 | 45 | 46 | $K_d$ (pM) | $\frac{K_d (hGH)}{K_d (mut)}$ |
| hGH | K | Y | L | Q | 340 | 1 |
| 3 cycles | | | | | | |
| 833A.2 | V | S | L | W | 190 ± 26 | 1.8 |
| 833B.2 | L | R | L | W | 190 ± 23 | 1.8 |
| 833A.1 | F | R | L | Y | 160 ± 23 | 2.2 |
| 833B.1 | V | F | L | R | 150 ± 19 | 2.3 |
| 833A.4 | A | I | Q | W | ND | ND |
| 833B.4 | L | Y | V | R | ND | ND |
| 833B.3 | Y | W | G | Y | ND | ND |
| 833A.3 | F | L | V | L | ND | ND |
| 5 cycles | | | | | | |
| 835A.5 | G | T | W | T | 270 ± 80 | 1.3 |
| 835A.6 | I | H | W | W | 76 ± 29 | 4.5 |
| 835A.3 | R | R | L | F | ND | ND |
| 835A.7 | M | R | W | R | ND | ND¶ |
| 835A.4 | R | T | A | V | ND | ND@ |
| 7 cycles | | | | | | |
| 873B.5 | R | Q | L | W | 140 ± 20 | 2.4 |
| 873B.6 | R | Q | L | W | 140 ± 20 | 2.4† |
| 873A.5 | R | T | A | V | ND | ND@ |
| 873B.2 | R | S | W | F | ND | ND |
| consensus: | | | | | | |
| | R | R | W | W | | |
| | Q | L | | | | |

B. Loop-A library

| | Residue Position | | | | | |
|---|---|---|---|---|---|---|
| Clone | 54 | 56 | 58 | 64 | $K_d$ (pM) | $\frac{K_d (hGH)}{K_d (mut)}$ |
| hGH | F | E | I | R | 340 | 1 |
| 3 cycles | | | | | | |
| 783B.4 | P | D | T | R | 210 ± 110 | 1.6 |

TABLE 5-continued

Binding data for individual hGH
clones mutated in (A) the Minihelix-1 or
(B) Loop-A. Affinity constants were measured by competition
binding to hGHbp versus $^{125}$I-labeled hGH. Wild-type hGH
affinity is from Cunningham and Wells, 1989, supra. The fold increase in affinity over hGH for binding hGHbp is shown as the
ratio $K_d$ (hGH)/$K_d$ (Mutant). Some clones were not analyzed
(ND). Identical affinities were assumed for equivalent variants
($^\dagger$). Clones with spurious mutations (E65V ‡; S57Y §; N47Y ¶;
P48S @) are indicated.

| | | | | | |
|---|---|---|---|---|---|
| 783B.7 | P | Y | I | K | 170 ± 30 | 2.0 |
| 783B.2 | H | W | L | K | 83 ± 25 | 4.2 |
| 783A.4 | M | R | L | K | ND | ND‡ |
| 4 cycles | | | | | | |
| 786A.2 | G | W | V | R | 660 ± 140 | 0.50 |
| 786A.3 | F | W | V | R | 630 ± 120 | 0.53 |
| 786B.3 | S | H | L | K | 620 ± 120 | 0.56§ |
| 786B.6 | P | W | L | R | 520 ± 100 | 0.67 |
| 786A.6 | P | L | D | K | 460 ± 100 | 0.74 |
| 786B.5 | P | T | V | K | 250 ± 40 | 1.4 |
| 786B.2 | P | Y | I | K | 170 ± 30 | 2.0$^\dagger$ |
| 786A.5 | P | L | Q | K | 120 ± 30 | 2.8 |
| 786A.4 | P | D | T | K | 61 ± 8 | 5.6 |
| 786A.1 | P | T | P | K | ND | ND |
| 786A.7 | P | A | L | K | ND | ND |
| 786B.7 | P | C | I | K | ND | ND |
| 6 cycles | | | | | | |
| 816B.6 | R | D | I | R | 350 ± 250 | 1.0 |
| 816B.4 | P | T | V | K | 250 ± 40 | 1.4$^\dagger$ |
| 816B.1 | P | D | I | K | 180 ± 40 | 1.9 |
| 816B.2 | P | Y | I | K | 170 ± 30 | 2.0$^\dagger$ |
| 816A.4 | P | E | I | K | 73 ± 16 | 4.8 |
| 816A.6 | P | E | I | K | 73 ± 16 | 4.8$^\dagger$ |
| 816A.5 | P | D | T | K | 61 ± 8 | 5.6$^\dagger$ |
| 816A.1 | E | W | V | K | ND | ND |
| 816A.2 | P | M | V | K | ND | ND |
| 816A.3 | P | L | Q | K | ND | ND |
| consensus: | | | | | | |
| | P | D | I | K | | |
| | | W | | | | |

(c) Improving affinity using additivity principles

According to additivity principles, mutations in non-interacting parts of a protein should combine to produce simple additive changes in the free energy of binding (Wells, 1990, supra). Therefore, it was sought to improve hGH binding through Site-1 by combining the substitutions isolated from phage-display libraries (FIG. 7). The three tightest-binding variants of hGH from the Helix-1 library (A=F10H,M14G,H18N,H21N, B=F10A,M14W,H18D, H21N, and C=M14S,H18F,H21L) were joined to each of the three tightest binding variants found in the Helix-4b library (D=R167N,D171S,E174S,F176Y,I179T, E=R167E,D171S, E174S,F176Y, and F=R167N,D171N,E174S,F176Y,I179T). All constructs were obtained in yields approaching that of wild-type hGH except for those containing variant A. Variant A and recombinants AD, AE, AF migrated as dimers (MW~44 kDa) in non-reducing SDS-PAGE and as monomers (MW~22 kDa) when reduced. Although these proteins did not contain an additional Cys residue, disulfide exchange could occur if they first formed non-covalent dimers. In fact, hGH is known to form a weak dimeric complex involving residues in helices 1 and 4. Cunningham et al., *Science*, 253, 1991, supra. Nevertheless, because these proteins formed disulfide dimers they were not pursued further. Variant C is also produced predominantly in disulfide dimer form too; however, the CD, CE, CF recombinants did not form a significant amount of dimer.

All the recombinants analyzed showed cumulative enhancements in affinity over the parental components (Table 6). The BD variant had the greatest affinity, which was 30-fold tighter than wild-type hGH. The tightest-binding variant from the Minihelix-1 library (K41I,Y42H,L45W, Q46W) and one of the tightest from the Loop-A library (F54P,R64K) were combined to produce the hexamutant, hGH 852b, whose affinity was about 40-fold higher than wild-type hGH. This was put together with the BD recombinant to yield the hGH variant, 852d, which bound about 400-fold tighter than wild-type hGH. Assuming simple additivity, it was expected that this variant would bind about 600-fold tighter than hGH from the product of the improvements in affinity by the individual components; this calculated value is reasonably close to the result. The 852d variant retained as wild-type only five of the 20 residues randomized (E56, I58, K172, T175, R178).

TABLE 6

Equilibrium binding
constants of recombined hGH variants. Binding constants
were measured by competitive displacement of either $^{125}$I-labeled wild-type hGH, BD, or 852d, using hGHbp and Mab5
(Cunningham and Wells, 1989, supra). The fold improvement
in binding affinity is expressed as $K_d$ (hGH)/$K_d$ (variant). Some
affinities ($^\dagger$) are from Lowman et al., Biochemistry, supra.
Helix-1 variants are B = (F10A, M14W, H18D, H21N), and C =
(M14S, H18F, H21L). Helix-4 variants are D = (R167N, D171S,
E174S, F176Y, I179T), E = (R167E, D171S, E174S, F176Y), and
F = (R167N, D171N, E174S, F176Y, I179T). BD, BF, CD, CE,
CF represent combinations of these mutations. 852b = (K41I,
Y42H, L45W, Q46W, F54P, R64K), and 852d = BD + 852b.

| Variant name | $K_d$ (pM) | $\dfrac{K_d \text{(hGH)}}{K_d \text{(variant)}}$ |
|---|---|---|
| hGH | 340 ± 50 | 1 |
| B$^\dagger$ | 100 ± 30 | 3.4 |
| C$^\dagger$ | 680 ± 190 | 0.5 |
| D$^\dagger$ | 40 ± 20 | 8.5 |
| E$^\dagger$ | 40 ± 20 | 8.5 |
| F$^\dagger$ | 60 ± 30 | 5.7 |
| BD | 10 ± 3 | 34 |
| CD | 11 ± 3 | 31 |
| CE | 14 ± 8 | 24 |
| BF | 16 ± 5 | 21 |
| CF | 21 ± 11 | 16 |
| 852b | 7.9 ± 2.4 | 43 |
| 852d | 0.9 ± 0.3 | 380 |

(d) Combinatorial libraries of hGH

Despite the simple additivity found in combining mutants from libraries sorted independently, complex additivity has been observed for some neighboring substitutions (e.g., F176Y interacting with E174S). Lowman et al., *Biochemistry*, supra. Some side-chains mutated from helix 1 (F10, M14, H18, H21) can potentially contact those mutated in helix 4 (R167, D171, T175, and I179). Therefore, a combinatorial approach to sorting mutants derived from the Helix 1 and Helix-4b libraries (Huse et al., *Science*, 246: 1275–1281 [1989]; Clackson et al., *Nature*, 352: 624–628 [1991]) was investigated. Independent binding selections were carried out on the Helix-1 and Helix-4b libraries for 0, 2, or 4 cycles. DNA from the Helix-1 pool was ligated together with DNA from the Helix-4b library that was sorted for binding to the hGHbp for the same number of rounds. The three combinatorial libraries were then sorted an additional 2 to 7 cycles and 68 representative clones were sequenced (Table 7).

TABLE 7 hGH variants from hormone-phagemid binding selection of combinatorial libraries. All variants contain (E174S, F176Y), except for those with the wild-type Helix 4 sequence (–), which were non-recombinants. Libraries 707A, 707B and 707E, or 707C were sorted for 2 to 7 cycles for binding to hGHbp (see text). The numbers listed under P indicate the fractional occurrence among the sequenced clones. The numbers listed under # designate each independent isolate (e.g., pH0714A.1 is the first sequence). Some affinities are from Lowman et al., Biochemistry, supra; equivalent variants are assumed to have identical affinities ([†]). Several variants appeared as > 10% disulfide dimers ([‡]). One clone contained an amber (TAG = Gln in SupE strains) codon ([§]), one contained a spurious mutation, E174N ([¶]), and one ([@]) contained two spurious mutations (L15R, K168R). Some variants were not expressed (NE) or not analyzed (ND).

| | | Helix 1 | | | | Helix 4b | | | | | |
|---|---|---|---|---|---|---|---|---|---|---|---|
| P | # | F10 | M14 | H18 | H21 | R167 | D171 | T175 | I179 | $K_d$ (pM) | $\dfrac{K_d(\text{hGH})}{K_d(\text{mut})}$ |
| (A) Combinatorial of unselected libraries: After 4 cycles (pH0714A; 5 sequences): | | | | | | | | | | | |
| 0.60 | 1 | H | G | N | N | N | S | T | N | ND | |
| 0.40 | 4 | A | N | D | A | N | N | T | N | 50 ± 40 | 6.8[‡@] |
| (B) Combinatorial of 2x-selected libraries: After 2 cycles (pH0712B; 7 sequences): | | | | | | | | | | | |
| 0.14 | 1 | F | S | F | G | H | S | T | T | ND | |
| 0.14 | 2 | H | Q | T | S | A | D | T | T | ND | |
| 0.14 | 4 | H | G | N | N | N | A | T | T | ND | |
| 0.14 | 5 | F | S | F | L | S | D | T | T | ND | |
| 0.14 | 6 | A | S | T | N | — | — | — | — | ND | |
| 0.14 | 7 | Q | Y | N | N | H | S | T | T | 74 ± 30 | 4.6 |
| 0.14 | 8 | W | G | S | S | — | — | — | — | ND | |
| After 2 cycles (pH0712E; 8 sequences): | | | | | | | | | | | |
| 0.13 | 1 | F | L | S | S | K | N | T | V | ND | |
| 0.13 | 2 | W | N | N | S | H | S | T | T | 160 ± 70 | 2.1 |
| 0.13 | 3 | A | N | A | S | N | S | T | T | ND | |
| 0.13 | 4 | P | S | D | N | — | — | — | — | ND | |
| 0.13 | 5 | H | G | N | N | N | N | T | T | ND | |
| 0.13 | 6 | F | S | T | G | — | — | — | — | ND | |
| 0.13 | 7 | M | T | S | N | Q | S | T | T | ND | |
| 0.13 | 8 | F | S | F | L | T | S | T | T | ND | |
| After 4 cycles (pH0714B; 6 sequences): | | | | | | | | | | | |
| 0.17 | 1 | A | W | D | N | — | — | — | — | 100 ± 30 | 3.3[†] |
| 0.17 | 2 | A | W | D | N | H | S | T | N | ND | |
| 0.17 | 3 | M | Q | M | N | N | S | T | T | NE[§] | |
| 0.17 | 4 | H | Y | D | H | R | D | T | T | ND | |
| 0.17 | 5 | L | N | S | H | — | — | — | — | 820 ± 200 | 0.4[†] |
| 0.17 | 6 | L | N | S | H | T | S | T | T | 34 ± 19 | |
| After 6 cycles (pH0716B; 8 sequences): | | | | | | | | | | | |
| 0.38 | 2 | A | W | D | N | — | — | — | — | 100 ± 30 | 3.3[†] |
| 0.13 | 4 | A | W | D | N | N | S | T | S | ND | |
| 0.13 | 7 | A | W | D | N | K | D | T | T | ND | |
| 0.13 | 1 | A | T | S | N | N | S | T | T | ND | |
| 0.13 | 3 | M | A | D | N | N | S | T | T | 68 ± 46 | 5.0[†‡] |
| 0.13 | 5 | H | Y | D | H | N | S | T | T | ND | |
| (pH0716E; 8 sequences): | | | | | | | | | | | |
| 0.38 | 1 | A | H | A | S | N | S | T | T | ND | |
| 0.25 | 7 | F | S | L | A | N | S | T | I | ND | |
| 0.13 | 3 | H | Y | D | H | Y | S | T | S | ND | |
| 0.13 | 4 | V | L | D | H | N | S | T | T | ND | |
| 0.13 | 6 | A | W | D | N | N | N | T | I | ND[¶] | |
| After 7 cycles (pH0717B; 12 sequences): | | | | | | | | | | | |
| 0.33 | 1 | A | W | D | N | N | A | T | T | 12 ± 6 | 28 |
| 0.17 | 6 | A | W | D | N | — | — | — | — | 100 ± 30 | 3.3[†] |
| 0.08 | 11 | A | W | D | N | N | S | T | N | ND | |
| 0.08 | 13 | A | W | D | N | R | N | T | T | ND | |
| 0.08 | 14 | A | W | D | N | K | S | T | S | ND | |
| 0.08 | 2 | F | S | T | G | — | — | — | — | ND | |

TABLE 7-continued hGH variants from hormone-phagemid binding selection of combinatorial libraries. All variants contain (E174S, F176Y), except for those with the wild-type Helix 4 sequence (−), which were non-recombinants. Libraries 707A, 707B and 707E, or 707C were sorted for 2 to 7 cycles for binding to hGHbp (see text). The numbers listed under P indicate the fractional occurrence among the sequenced clones. The numbers listed under # designate each independent isolate (e.g., pH0714A.1 is the first sequence). Some affinities are from Lowman et al., Biochemistry, supra; equivalent variants are assumed to have identical affinities (†). Several variants appeared as > 10% disulfide dimers (‡). One clone contained an amber (TAG = Gln in SupE strains) codon (§), one contained a spurious mutation, E174N (¶), and one (@) contained two spurious mutations (L15R, K168R). Some variants were not expressed (NE) or not analyzed (ND).

|  |  | Helix 1 | | | Helix 4b | | | | | $K_d$ | $\frac{K_d(\text{hGH})}{K_d(\text{mut})}$ |
|---|---|---|---|---|---|---|---|---|---|---|---|
| P | # | F10 | M14 | H18 | H21 | R167 | D171 | T175 | I179 | (pM) |  |
| 0.08 | 7 | I | Q | E | H | N | S | T | T | 16 ± 10 | 21 |
| 0.08 | 15 | H | Y | D | H | N | S | T | T | ND |  |
|  |  |  |  |  | (pH0717E; 8 sequences): | | | | | | |
| 0.50 | 1 | F | S | L | A | N | S | T | V | 32 ± 5 | 11 |
| 0.25 | 13 | A | H | A | S | N | S | T | T | ND |  |
| 0.13 | 14 | A | W | D | N | A | N | T | T | ND |  |
| 0.13 | 11 | H | Y | D | H | Y | S | T | S | ND |  |
|  |  |  |  |  | Combinatorial of 4x-selected libraries: | | | | | | |
|  |  |  |  |  | After 4 cycles (pH0714C; 6 sequences): | | | | | | |
| 0.67 | 2 | F | S | F | L | K | D | T | T | 150 ± 70 | 2.3‡ |
| 0.17 | 1 | F | S | F | L | N | S | T | T | 11 ± 3 | 31† |
| 0.17 | 5 | M | A | D | N | N | S | T | T | 68 ± 46 | 5.0†‡ |

Overall, the highest affinity variants isolated from any of these three combinatorial sorts resembled those previously isolated by independent sorting of the Helix-1 and Helix-4b libraries. Lowman et al., *Biochemistry*, supra. For example, the highest affinity mutants isolated previously from the Helix-1 library were F10A,M14W,H18D,H21N (Helix-1.B) and F10H,M14G,H18N,H21N (Helix-1.A); these bound about 3.3-fold and 2.4-fold tighter than wild-type hGH, respectively. The Helix 1.A sequence was recovered in 60% of the clones from Combinatorial Library A, and in 13% of the clones isolated in early rounds of sorting from Combinatorial Library B. The Helix-1.B sequence predominated in later rounds of sorting the Combinatorial Library B. Most of these were independent clones (not siblings or contaminants), because they had different DNA sequences and usually differed in the mutants selected in helix 4.

Similar results were obtained with selectants in helix 4. When the Helix-4b library was independently sorted, a number of sequences were obtained containing R167N, D171S or N, T175 (conserved), and I179T. Lowman et al., *Biochemistry*, supra. These were the same residues that tended to be selected in Combinatorial Libraries A, B and C. In fact, one of the best mutants previously isolated (R167N, D171S,T175,I179T) was commonly isolated by combinatorial sorting and predominated especially in the later rounds.

Some sequences sorted by combinatorial means were very different from ones selected from the two independent libraries; but this could arise for statistical reasons. For example, the Helix-1 and Helix-4b libraries contain about $10^6$ different DNA sequences, and if combined (without pre-selection) would contain $10^{12}$ possible combinations. Transformation efficiencies limit the sampling size to $\leq 10^7$ independent clones. Thus, the selection of the same sequences is remarkable given the high diversity of sequences possible in these libraries and the mild improvements in affinity being selected for.

The affinities for a number of these isolates were measured (Table 7). All had improved binding affinity (2- to 29-fold) compared to wild-type hGH. Most were improved over E174S,F176Y, which was present in all the starting clones, and independently caused a 5.6-fold increase in affinity over wild-type hGH. Lowman et al., *Biochemistry*, supra. The highest affinity variants were generally isolated from later rounds of sorting and were highly abundant in those pools. For example, the highest affinity mutant tested was clone 717B.1, which was isolated after seven rounds of sorting of Combinatorial Library B. This isolate represented a third of the clones in that pool. Remarkably, this clone is identical to the BD variant (Table 6), except that instead of D171S it contained the conservative substitution, D171A. Not surprisingly, the 717B.1 and BD variants bound with comparable affinities (12 pM and 10 pM, respectively). These data suggest that combinatorial and additive strategies yield comparable solutions for successful optimization of affinity.

(e) Testing the importance of individual side-chains in affinity maturation

The contribution of some of the phage-improved residues to the binding affinity was evaluated by introducing them into wild-type hGH, or by converting them back to the wild-type residue in the affinity-matured BD variant (Table 8). The K41I,Y42H,L45W,Q46W variant bound 4.5-fold tighter than wild-type hGH. Each of the single mutants in hGH caused 1.7- to 2.5-fold reductions in affinity. This indicates that the combination of mutations at this site is critical for the affinity improvements. These residues lie on adjacent positions on one face of the minihelix-1.

TABLE 8

Testing the contributions of individual side-chains identified by phage display. Receptor binding affinities of variants were measured by BIAcore ™ ([†]) or by RIA (unmarked) and normalized to the RIA value for hGH as determined by Cunningham and Wells, 1989, supra. Point mutations were made to test the contributions of individual side-chains found after phage sorting. The fold decrease in affinity is expressed as $K_d$ (revertant) /$K_d$ (parent), where parent is the background used for mutagenesis.

Point mutants in wild-type background:

| | $K_d$ (pM) | $\frac{K_d \text{(mut)}}{K_d \text{(hGH)}}$ |
|---|---|---|
| hGH (wild-type) | 340 ± 50 | 1 |
| [†]K41I | 580 ± 140 | 1.7 |
| [†]Y42H | 860 ± 50 | 2.5 |
| [†]L45W | 722 ± 60 | 2.1 |
| [†]Q46W | 780 ± 100 | 2.3 |

Revertants in BD background:

| | $K_d$ (pM) | $\frac{K_d \text{(mut)}}{K_d \text{(BD)}}$ |
|---|---|---|
| BD | 10 ± 3 | 1 |
| D18H, N21H | 12 ± 9 | 1.1 |
| A10F, W14M | 13 ± 5 | 1.2 |
| [†]A10F | 13 ± 4 | 1.3 |
| N167R, S171D | 17 ± 8 | 1.6 |
| T179I | 18 ± 9 | 1.7 |
| Y176F | 49 ± 21 | 4.6 |

Affinity improvements caused by substitutions in the BD variant were tested by mutating them back to the wild-type residue either individually or in pairs (when the residues were adjacent) (Table 8). This showed that seven of the nine substitutions contribute only very subtle improvements in binding (1.1 to 1.7-fold). Even the most dominant effect, F176Y, imparts only a 4.6-fold improvement in binding. Nonetheless, the product of these effects in the octamutant, F10A,M14W,H18D,H21N,R167N,D171S,F176Y,I179T, predicted a 16-fold improvement in affinity versus wild-type hGH. This compares to the 34-fold enhancement measured for the BD variant that contains in addition E174S.

(f) Effects of affinity maturation on the kinetics of binding

In Example I, the BIAcore™ biosensor device was used to measure the kinetics of binding for alanine mutants produced at residues in hGH that become buried at Site 1 upon receptor binding. For a better understanding of the molecular basis for affinity improvements selected here, the BIAcore™ biosensor was used to measure their kinetics of binding to the hGHbp (Table 9). In general, as the affinity from wild-type hGH was increased, the off-rate decreased with little change in on-rate. In fact, in going from wild-type to the highest affinity mutant, 852d, there was a >60-fold decrease in the off-rate and only a 4-fold increase in the on-rate. (The off-rate was too slow to measure accurately, but if it was calculated from the $K_d$ measured by RIA and the on-rate, the off-rate would be 100-fold slower than wild-type hGH.) The hGH binding site had previously been recruited into a homolog of hGH, human placental lactogen (hPL). This differs in sequence by 15% from hGH and binds ~2000-fold weaker. Lowman et al., *J. Biol. Chem.*, supra. The recruited hPL variant has kinetic parameters for binding that are similar to hGH (Table 9). Like the affinity-matured hGH variant, this mutant shows much larger improvements in off-rate (~100-fold) compared to on-rate (~10-fold) relative to wild-type hPL. The fact that off-rate is most affected among the phage selectants suggests that the sorting was performed under conditions approaching equilibrium.

TABLE 9

Binding kinetics of hGH variants. BIAcore ™ biosensor measurements were carried out with immobilized hGHbp (S201C) in PBS buffer + 0.05% Tween-20. The BIAcore ™ biosensor $K_d$ is calculated from $k_{off}/k_{on}$, except for hPL, for which $k_{on}$ and $K_d$ were measured and $k_{off}$ was calculated ([†]). The ratio of $K_d$'s indicates the fold increase in binding affinity vs. wt-hGH according to the BIAcore ™ biosensor data. Mutant combinations in hGH are designated by Roman numerals. The hPL (0274) contains V4I, D56E, M64R, E174A, M179I.

| Mutant | $k_{on}/10^4$ $M^{-1}s^{-1}$ | $k_{off}/10^{-5}$ $s^{-1}$ | $K_d$ (nM) | $\frac{K_d \text{(hGH)}}{K_d \text{(mut)}}$ |
|---|---|---|---|---|
| hPL | 3.2 | 6000[†] | 1800 | 0.0006 |
| hPL (0274) | 43 | 49 | 1.1 | 0.79 |
| hGH (822a1) {10Y, 14E, 18R, 21G} | 40 | 53 | 1.3 | 0.93 |
| hGH | 24 | 34 | 1.4 | 1 |
| I. hGH (835a6) {41I, 42H, 45W, 46W} | 13 | 6.9 | 0.52 | 2.7 |
| II. hGH (816a4) {54P, 64K} | 21 | 6.6 | 0.31 | 4.5 |
| III. hGH (852b) {I + II} | 36 | 5.1 | 0.14 | 10 |
| IV. hGH (BD) | 20 | 3.0 | 0.15 | 9.3 |
| hGH (852d) {III + IV} | 98 | ≤0.6 | ≤0.006 | ≥230 |

Conclusion

Regions of hGH were randomly mutated that were thought to be important either because they were in contact with the receptor or because when converted to alanine they affected binding affinity. Thus, an average random mutant from these libraries should be dramatically reduced in binding affinity from wild-type hGH. Yet after only a few rounds of selection, isolates bound with similar and often higher affinity than wild-type hGH. The clones isolated usually exhibited consensus sequences that were different from the wild-type (Table 4).

Very small improvements in affinity led to rapid and almost exclusive convergence in these libraries. For example, the R64K mutant separately binds only ~3-times tighter than wild-type hGH (Cunningham et al., 1990, supra). Yet after Just three cycles of binding selection R64K dominated the library (Table 5). Similarly, I179T contributed only a 1.7-fold improvement in affinity (Table 8). However, when sorted separately in the Helix-4b library of Lowman and Wells, supra, or combinatorially with mutants in Helix-1 (Tables 4 and 7) it was found that I179T was almost exclusively selected. Strong selection for these subtle improvements in affinity emphasizes the power of this technique for rescuing the highest affinity variants in the pool.

Not all variants will be displayed on the phage (see Wells and Lowman, *Current Opinion in Struct. Biol.*, 2: 597–604 [1992]). This is because mutants that are misfolded or unstable may be either digested by proteases, aggregated, or blocked in secretion or assembly on phage. Although there does not appear to be a strong bias against particular DNA sequences, there is a clear selection against Cys-containing mutants, which selection has been previously noted for hGH mutants (Lowman and Wells, supra). The number of codons simultaneously mutated was deliberately limited to four (~$10^6$ DNA sequences) so that there would be a good chance of having each represented in the starting pool of phagemids (~$10^7$ independent transformants).

Less than half of the side-chains that become buried at Site 1 by the first receptor significantly affect binding affinity when converted to alanine [Example I, FIG. 1A]. The minihelix-1 contact residues provide a good example of this (Table 3). The Y42 and Q46 side-chains make more van der Waals contacts and undergo more burial alone than K41 and L45 combined. Yet, Y42A and Q46A have almost no effect upon binding compared to the mutations at K41 and L45.

Figure 8A:
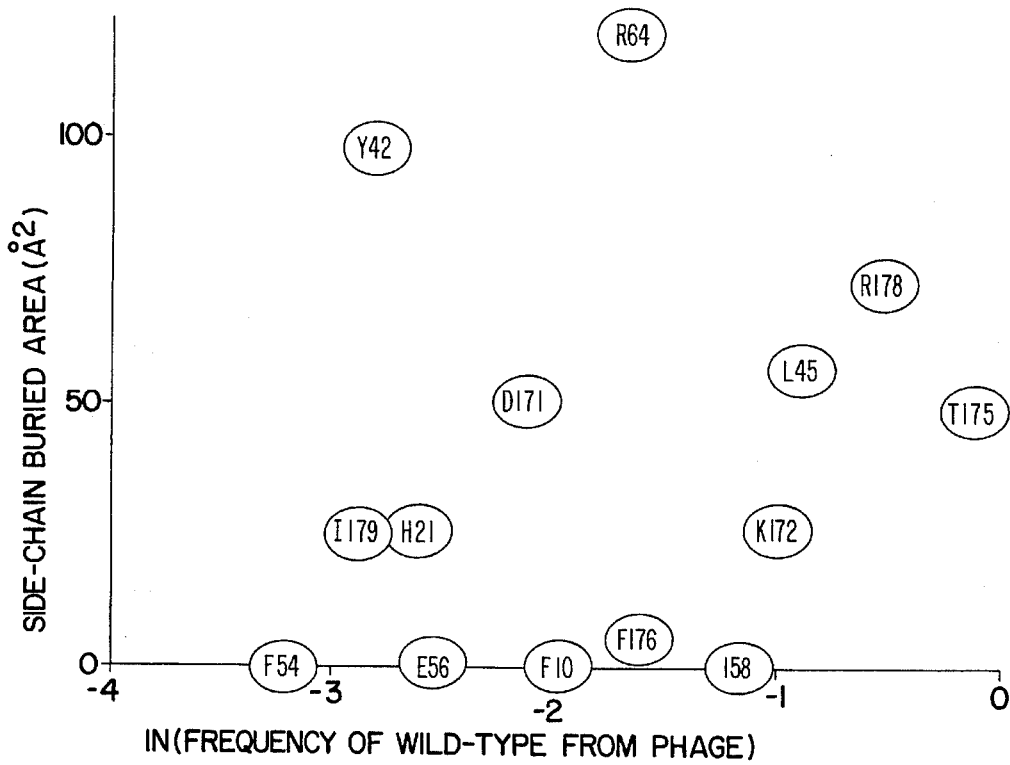
FIGS. 8A, 8B, and 8C depict the relationship among the hGH structural epitope, phage-derived epitope, and evolutionary variants, respectively. The natural logarithm of the frequency with which the wild-type hGH residues appeared in hGH-phagemid pools (Lowman et al., supra) sorted for receptor binding is shown on the x-axis. Data from the Combinatorial libraries were not included. The log scale was chosen for comparison with buried surface areas. Residues M14, H18, K41, Q46, R167, and E174 do not appear on this graph, because no wild-type residues were found among any of the selected libraries.

These studies suggest that functionality is not easily assessed by the extent to which a side-chain makes contact with the receptor. Another way to evaluate this is to correlate the conservation of wild-type residues after binding selection with the extent to which they are buried by the receptor. As shown in FIG. 8A, overall there is essentially no correlation ($R^2=0.022$) with the conservation of wild-type residues from phagemid libraries. This is also evident by comparing FIG. 6B and FIG. 6C. However, the three most conserved side-chains (T175, R178, L45) all have substantial contact with receptor.

Figure 6C:
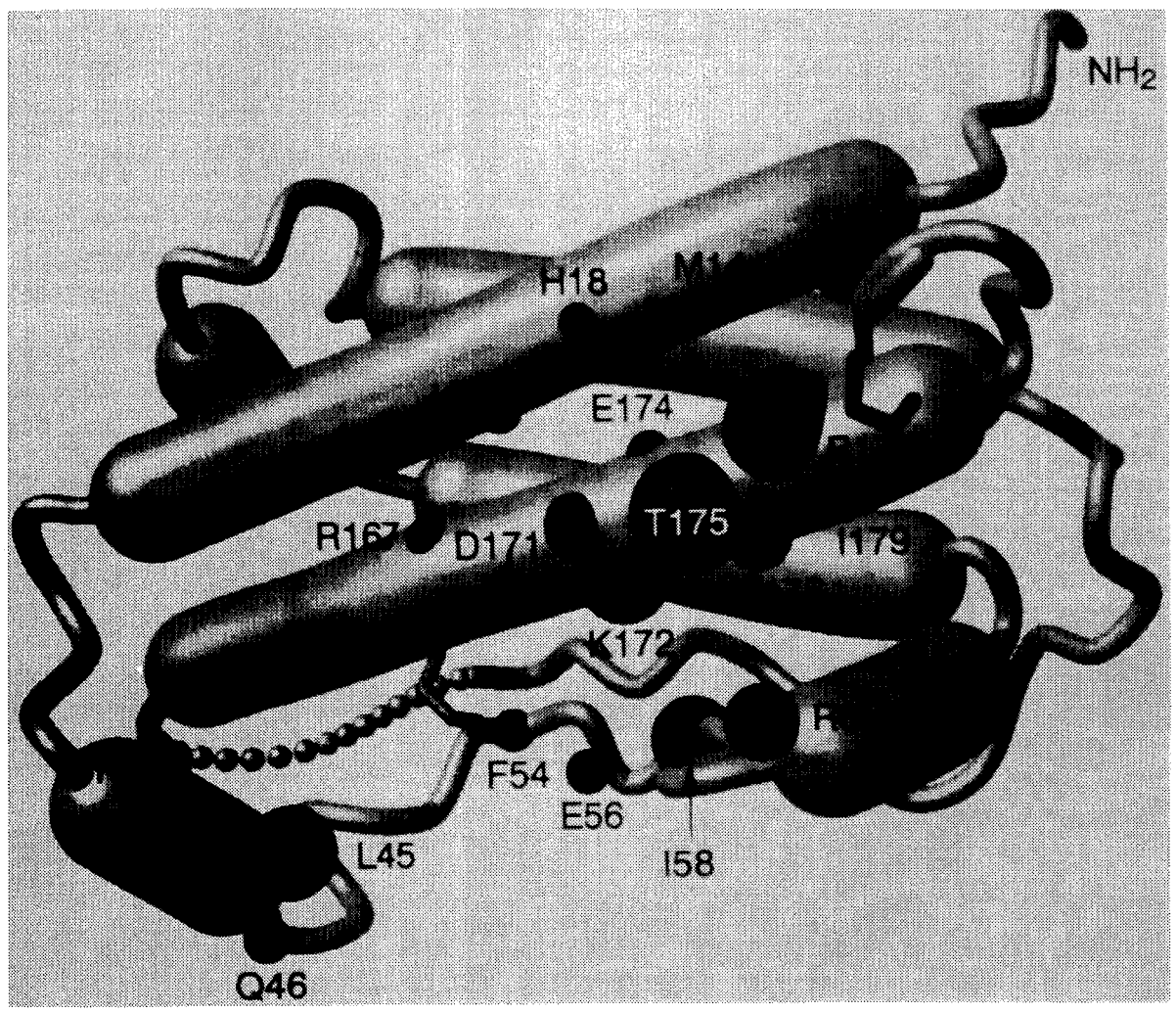
Figure 8B:
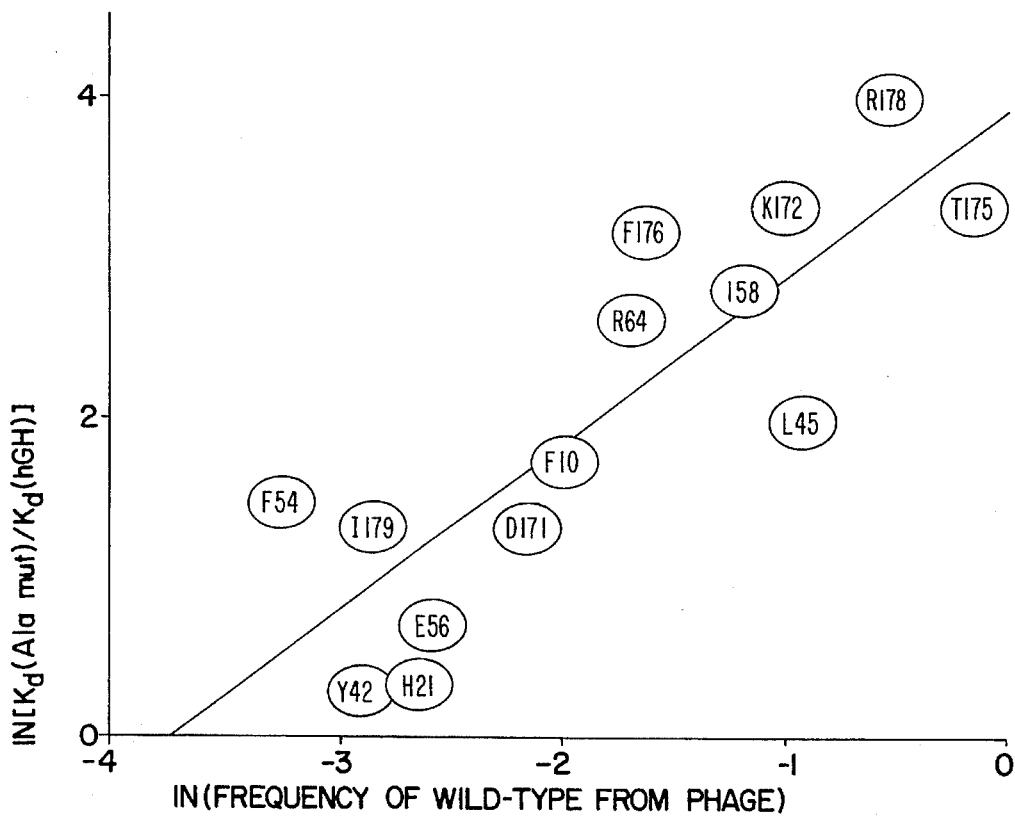

There is a reasonable correlation ($R^2=0.71$) between the reduction in affinity as assessed by alanine-scanning mutagenesis and side-chain conservation following phage sorting (FIG. 8B; compare FIG. 6A and FIG. 6C). A roughly linear correspondence is seen (y=3.9+1.0 x). If data from the Combinatorial libraries are included, R167 is added, and the correlation falls to 0.65. The trend for functional importance versus conservation argues for considering functional information for choosing residues to randomize over considerations of structure (FIG. 8A).

Figure 8C:
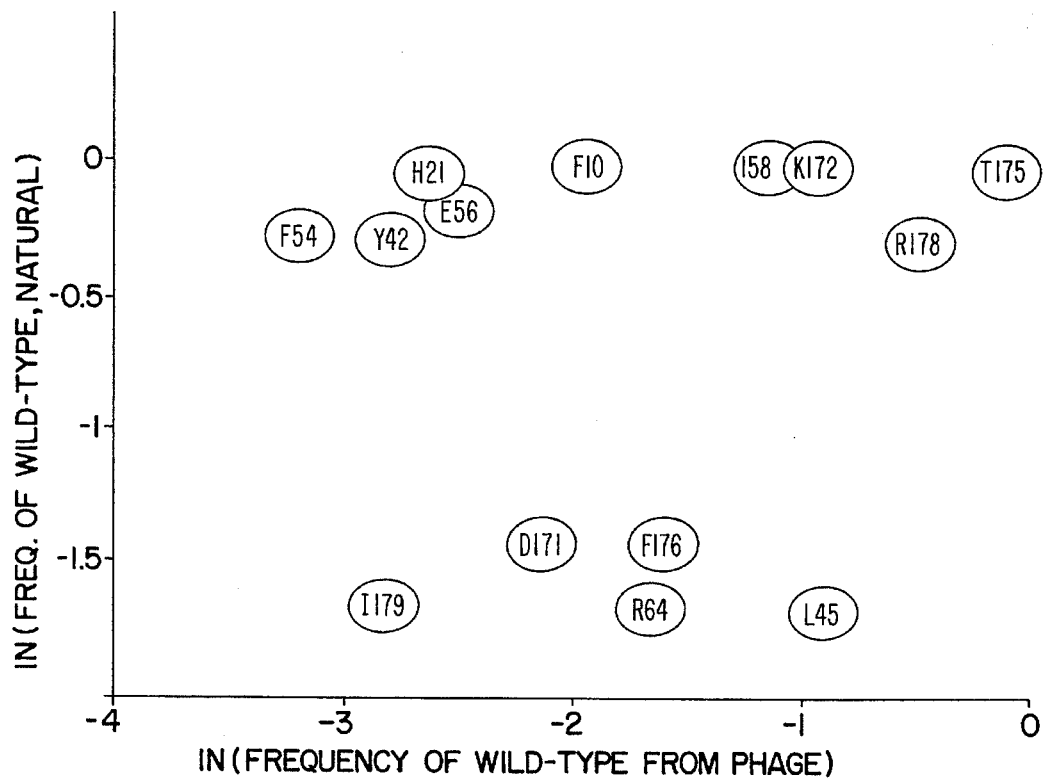
Figure 9:
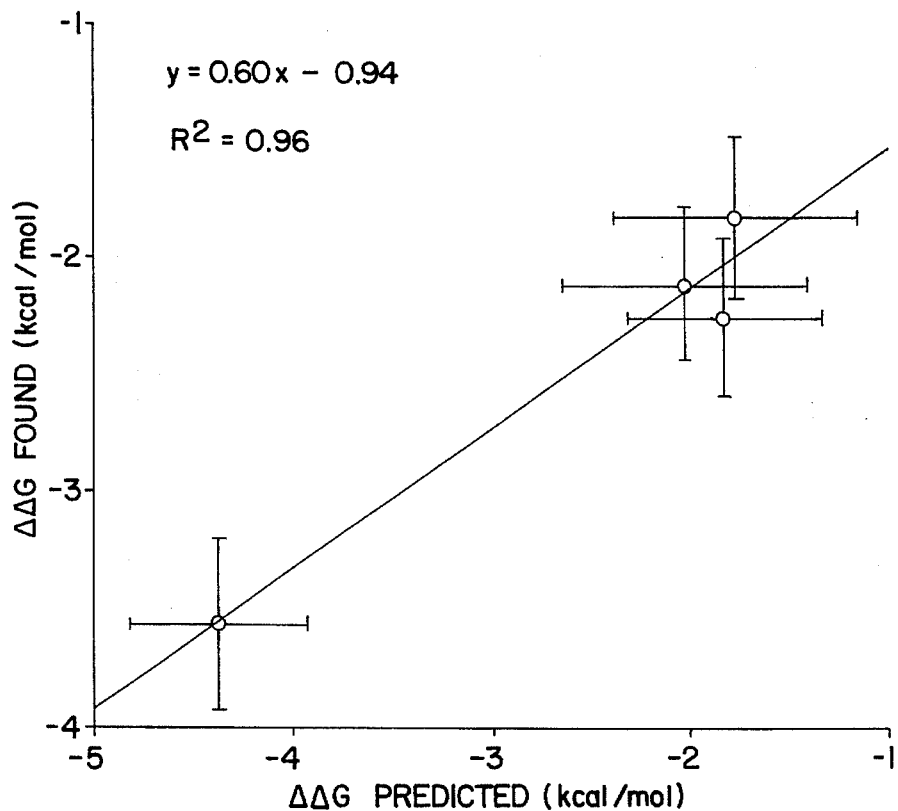
FIG. 9 discloses the additivity of phage-derived mutations. The change (ΔΔG) in free energy of binding versus that of wild-type hGH was compared with the sum of ΔΔG for component mutations. The points shown correspond to the combinations of (1) variant BD vs. [B plus D]; (2) variant 852b vs. [minihelix-1 plus loop-A]; (3) variant BF vs. [B plus F]; and (4) variant 852d vrs. [BD plus 852b]. Error bars were estimated from standard deviations using a propagation of errors calculation. Bevington, *Data Reduction and Error Analysis for the Physical Sciences*, pp. 56–65 (McGraw-Hill, New York, 1969). The line shown is y=–0.94+0.60x; $R^2$=0.96.

These data indicate that functionality determined by alanine-scanning mutagenesis is similar to that determined by sequence conservation after binding selection. However, there is no correlation ($R^2=0.005$) between the frequency of conservation of given residues among natural variant growth hormones and conservation following binding selection from phage-display libraries (FIG. 8C). In nature the functional constraints on growth hormone are not fixed as they are by the in vitro binding selection.

Many of the selected residues at functionally important and highly buried sites, either at the interface or in the hormone itself, tend to be retained as the wild-type residue or a close homolog. For example, all five of the residues that are most conserved as the wild-type after extensive phage sorting (E56, I58, K172, T175, and R178) are completely buried in the complex; converting them to alanine caused 4- to 60-fold reductions in affinity (Cunningham and Wells, 1989, supra). When substitutions were tolerated at these positions they were typically similar to the wild-type residue. For example, the highest affinity selectants contained either Asp or Glu at position 56, beta-branched residues at position 58, Lys or Arg at 172, Thr or Ser at 175, and Lys or Arg at 178 (Table 5; Lowman et al., Biochemistry, supra).

There is another group of functionally important residues that become highly buried upon receptor binding (K41, L45, R64, D171 and I179). When these were randomized, improved substitutes were found that tended to be similar in character to the wild-type residue. For example, K41 was often replaced with Arg; L45 was substituted with large hydrophobic side-chains; R64 was most frequently substituted by Lys; D171 was optimally replaced by Asn and sometimes Ser; I179 was usually substituted by d-branched residues (Tables 4, 5, and 7; Lowman et al., Biochemistry, supra). Thus, improvements can be made at functionally important residues buried at the interface-they tend to be toward an isosteric side-chain or one of similar chemical character.

Two of the residues that were randomized (H18 and E174) had enhanced binding affinity when converted to alanine and were completely buried in the complex. These almost always sorted to something smaller than the wild-type residue. For example, the preferred substitution for H18 was Asp or Asn, and for E174 was Ala, Ser or Thr. Lowman et al., Biochemistry, supra. The packing at these positions, called hindrance determinants, is energetically unfavorable.

Another class of residues (H21, Y42, Q46 and R167) are highly buried at the interface but have little or no effect on binding affinity when converted to alanine. These residues rarely sort back to the wild-type residue. For example, H21 tended to sort to Asn; Y42 often came back as Arg or Gln; Q46 preferred Trp, and R167 often sorted to Asn (Tables 4, 5, and 7; Lowman et al., Biochemistry, supra). Despite the consensus found at these buried residues the affinity enhancements made from them were very small (Table 8). Thus, it appeared more difficult to obtain improvements in affinity from contact residues that were functionally inert.

The last group of residues (F10, M14, and F54) are virtually buried in the folded hormone and affect binding affinity by 2- to 4-fold when converted to alanine, presumably by indirect structural effects. Surprisingly, radical substitutions were tolerated here that show consensus sorting (Tables 4, 5, and 7; Lowman et al., Biochemistry, supra). For example, F54P was almost the sole solution in the Loop-A library. Phe 54 is 84% buried in the hormone and 10 Å away from making contact with the receptor. It is estimated that the F54P mutant enhances affinity by a factor of about 1.6-fold based on the fact that the double mutant (F54P, R64K) is improved in binding by 4.8 fold (Table 5), and the R64K mutant alone enhances binding by a factor of ~3 (Cunningham et al., 1991, supra). Residues 10 and 14 tend to co-vary, which is not surprising given their adjacent positions along helix 1. In general, the sum of the volumes of these two side-chains in the selectants tended to be the same or smaller than F10 plus M14. This is consistent with their tightly packed arrangement.

Although it is possible to rationalize the general features of these mutants by combining the functional and structural data, there are always unusual mutants that come through the sorting. For example, I179 was almost always conservatively replaced by a β-branched side-chain (especially Ile or Thr), but I179S also appeared (Table 7). Similarly, L45 was almost always replaced by a large side-chain (Leu or Trp), but L45A was also found (Table 5). Provided they are able to fold, such variants may be expected to persist through many rounds of selection at a background level, even though they may fail to improve or may even weaken binding affinity.

These studies suggest guidelines for affinity maturation of binding interfaces using monovalent phage display. A starting point toward efficient optimization of affinity is a complete alanine scan of the relevant interface. One cannot easily search more than 5 or 6 codons exhaustively (Lowman and Wells, supra); therefore, the library needs to be focused on residues where one can hope to improve affinity. It is also possible to limit the codon choices (see, e.g., Arkin and Youvan, Bio/Technology, 10: 297–300 [1992]), but this makes assumptions about what may or may not be useful substitutions. This is more reasonable to do if one has detailed knowledge of the structural interface a priori.

The residues where the most obvious improvements in affinity occurred were those that were shown by alanine-scanning mutagenesis to most affect binding. For example, the largest improvements in affinity came from R64K, E174S, and F176Y. E174A was known to enhance affinity, but R64A and F176A caused large reductions in affinity. Thus, despite the fact that the most highly conserved residues in the phage sorting were those that were most important by alanine-scanning mutagenesis, there were still improved variants to be found.

The functional data may be more important for targeting residues for optimization than the structural data. For example, several residues that are not in contact with the receptor (F10, M14, and F54), but affected binding when converted to alanine, produced affinity enhancements when randomly mutated. Moreover, some residues in contact with the receptor, but of little functional significance by alanine-scanning mutagenesis (Y42, Q46), failed to improve affinity when phage mutations were examined as point mutations (Table 8).

Ideally, one should randomize residues that can contact each other in the same mutagenesis step so that they are allowed to co-vary. Co-variance was seen in the Helix-1, Minihelix-1, and Helix 4a libraries when residues were close enough to interact. Sorting libraries by combinatorial means is especially useful in situations where mutations may lead to complex additive effects. For example, if side-chain replacements cause large conformational changes, as they may in flexible loops in antibodies, combinatorial sorting would allow for improvements by searching randomly for the best combinations of mutant heavy and light chains. Muse et al., supra; Clackson et al., supra; Collet et al., *Proc. Natl. Acad. Sci. USA*, 89: 10026–10030 (1992).

Nonetheless, improvements in hGH tended to occur by simple additive effects both between libraries and within libraries and even when the side-chains can interact. Practically, this means that one can randomize many residues independently and combine them in the end to obtain high-affinity variants. Fundamentally, it suggests that the interactions between side-chains, even neighboring ones, often have little effect, or can be compensated for without significant effect, on the free energy of binding receptor.

What is claimed is:

1. A human growth hormone variant having at least one amino acid substitution selected from the group consisting of the lysine at position 41 and the leucine at position 45 of native human growth hormone, numbered from the mature N-terminus of native human growth hormone.

2. The variant of claim 1 wherein the variant has at least one amino acid substitution selected from the group consisting of K41I, K41R, and L45W.

3. A human growth hormone variant having at least two amino acid residues replaced with different amino acid residues, wherein the variant has a set of amino acid substitutions selected from the group consisting of F54P, E56D, I58T,R64K; F54P,E56W,I58T,R64K; and F54P, R64K, numbered from the mature N-terminus of 191-amino acid human growth hormone.

4. A composition comprising a human growth hormone variant having at least one amino acid substitution selected from the group consisting of the lysine at position 41 and the leucine at position 45 of native human growth hormone, numbered from the mature N-terminus of native human growth hormone and a pharmaceutically acceptable carrier.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

GCCACCTGAT GTCTAAGAAA C          21

( 2 ) INFORMATION FOR SEQ ID NO:2:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

TTTGAAGAGG CCTATATGGC CAAGGAACAG AAG          33

( 2 ) INFORMATION FOR SEQ ID NO:3:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

CAGAACCCCC ATTGACGTCC CTCTGTTTC          29

( 2 ) INFORMATION FOR SEQ ID NO:4:

( i ) SEQUENCE CHARACTERISTICS:
        ( A ) LENGTH: 45 bases
        ( B ) TYPE: nucleic acid (C) STRANDEDNESS: single
(D) TOPOLOGY: linear (xi) SEQUENCE DESCRIPTION: SEQ ID NO:4:

TCCCGAAGGA GCAGNNSNNS TCGTTCNNSN NSAACCCGCA GACGT  45

(2) INFORMATION FOR SEQ ID NO:5:

(i) SEQUENCE CHARACTERISTICS:
(A) LENGTH: 44 bases
(B) TYPE: nucleic acid
(C) STRANDEDNESS: single
(D) TOPOLOGY: linear (xi) SEQUENCE DESCRIPTION: SEQ ID NO:5:

CTGCGGGTTS NNSNNGAACG ASNNSNNCTG CTCCTTCGGG ATAT  44

(2) INFORMATION FOR SEQ ID NO:6:

(i) SEQUENCE CHARACTERISTICS:
(A) LENGTH: 21 bases
(B) TYPE: nucleic acid
(C) STRANDEDNESS: single
(D) TOPOLOGY: linear (xi) SEQUENCE DESCRIPTION: SEQ ID NO:6:

AACCCCAGA CGTCCCTCTG T  21

(2) INFORMATION FOR SEQ ID NO:7:

(i) SEQUENCE CHARACTERISTICS:
(A) LENGTH: 33 bases
(B) TYPE: nucleic acid
(C) STRANDEDNESS: single
(D) TOPOLOGY: linear (xi) SEQUENCE DESCRIPTION: SEQ ID NO:7:

GAAACACAAC AGTAAAGGTA ACCTAGAGCT GCT  33

(2) INFORMATION FOR SEQ ID NO:8:

(i) SEQUENCE CHARACTERISTICS:
(A) LENGTH: 24 bases
(B) TYPE: nucleic acid
(C) STRANDEDNESS: single
(D) TOPOLOGY: linear (xi) SEQUENCE DESCRIPTION: SEQ ID NO:8:

CGTCTTCAAG AGTTCAACTT CTCC  24

(2) INFORMATION FOR SEQ ID NO:9:

(i) SEQUENCE CHARACTERISTICS:
(A) LENGTH: 60 bases
(B) TYPE: nucleic acid
(C) STRANDEDNESS: single
(D) TOPOLOGY: linear (xi) SEQUENCE DESCRIPTION: SEQ ID NO:9:

CCCTCTGTNN STCANNSTCT NNSCCGACAC CCAGTAATNN SGAGGAAACA  50

CAACAGAAGA  60

(2) INFORMATION FOR SEQ ID NO:10:

(i) SEQUENCE CHARACTERISTICS:
(A) LENGTH: 69 bases
(B) TYPE: nucleic acid ( C ) STRANDEDNESS: single
( D ) TOPOLOGY: linear ( x i ) SEQUENCE DESCRIPTION: SEQ ID NO:10:

GTTACTCTTC TGTTGTGTTT CCTCSNNATT ACTGGGTGTC GGSNNAGASN    50

NTGASNNACA GAGGGACGT    69

( 2 ) INFORMATION FOR SEQ ID NO:11:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( x i ) SEQUENCE DESCRIPTION: SEQ ID NO:11:

CTGCGTGCTC ACCGTCTTCA CCAGTTGGCC TTTG    34

( 2 ) INFORMATION FOR SEQ ID NO:12:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:12:

GTCAGCACAT TCCTGCGCAC C    21

( 2 ) INFORMATION FOR SEQ ID NO:13:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( x i ) SEQUENCE DESCRIPTION: SEQ ID NO:13:

CTCTCGCGGC TCTTCGACAA CGCGATGCTG CGTGCT    36

( 2 ) INFORMATION FOR SEQ ID NO:14:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( x i ) SEQUENCE DESCRIPTION: SEQ ID NO:14:

TACTGCTTCA GGAAGGACAT GGACAAGGTC AGC    33

( 2 ) INFORMATION FOR SEQ ID NO:15:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:15:

CTGCGCATCG TGCAGTGC    18

( 2 ) INFORMATION FOR SEQ ID NO:16:

( i ) SEQUENCE CHARACTERISTICS:
        ( A ) LENGTH: 27 bases
        ( B ) TYPE: nucleic acid (C) STRANDEDNESS: single
(D) TOPOLOGY: linear ( x i ) SEQUENCE DESCRIPTION: SEQ ID NO:16:

CTCTCGAGGC TCTTCGACAA CGCGTGG 27

( 2 ) INFORMATION FOR SEQ ID NO:17:

( i ) SEQUENCE CHARACTERISTICS:
(A) LENGTH: 33 bases
(B) TYPE: nucleic acid
(C) STRANDEDNESS: single
(D) TOPOLOGY: linear ( x i ) SEQUENCE DESCRIPTION: SEQ ID NO:17:

CAGACCTCCC TCTGTCCCTC AGAGTCTATT CCG 33

( 2 ) INFORMATION FOR SEQ ID NO:18:

( i ) SEQUENCE CHARACTERISTICS:
(A) LENGTH: 30 bases
(B) TYPE: nucleic acid
(C) STRANDEDNESS: single
(D) TOPOLOGY: linear ( x i ) SEQUENCE DESCRIPTION: SEQ ID NO:18:

ACACCCTCCA ACAAGGAGGA AACACAACAG 30

( 2 ) INFORMATION FOR SEQ ID NO:19:

( i ) SEQUENCE CHARACTERISTICS:
(A) LENGTH: 45 bases
(B) TYPE: nucleic acid
(C) STRANDEDNESS: single
(D) TOPOLOGY: linear ( x i ) SEQUENCE DESCRIPTION: SEQ ID NO:19:

CCAAAGGAAC AGATTCATTC ATTCTGGTGG AACCCCAGA CCTCC 45